US006287858B1

(12) United States Patent
D'Andrea et al.

(10) Patent No.: US 6,287,858 B1
(45) Date of Patent: Sep. 11, 2001

(54) DEUBIQUITINATING ENZYMES THAT REGULATE CELL GROWTH

(75) Inventors: Alan D. D'Andrea, Winchester, MA (US); Yuan Zhu, Blue Bell, PA (US)

(73) Assignee: Dana Farber Cancer Institute, Boston, MA (US)

( * ) Notice: Subject to any disclaimer, the term of this patent is extended or adjusted under 35 U.S.C. 154(b) by 0 days.

(21) Appl. No.: 09/019,095

(22) Filed: Feb. 5, 1998

Related U.S. Application Data

(63) Continuation of application No. PCT/US96/12884, filed on Aug. 7, 1996.
(60) Provisional application No. 60/019,787, filed on Jun. 14, 1996, and provisional application No. 60/002,066, filed on Aug. 9, 1995.

(51) Int. Cl.$^7$ .......................... C12N 15/85; C12N 15/00; C12N 15/11; C12N 9/00; C07H 21/04
(52) U.S. Cl. ............................ 435/375; 435/6; 435/69.1; 435/183; 435/226; 435/320.1; 435/325; 435/355; 435/366; 536/23.1; 536/23.2; 536/23.5
(58) Field of Search .............................. 435/6, 69.1, 91.1, 435/440, 183, 2.2, 219, 226, 325, 354, 355, 375, 366, 320.1; 514/44; 536/23.1, 23.2, 23.5, 24.3, 24.37, 24.33

(56) References Cited

U.S. PATENT DOCUMENTS

| | | | |
|---|---|---|---|
| 5,132,213 | 7/1992 | Bachmair et al. | 435/69.7 |
| 5,212,058 | 5/1993 | Baker et al. | 435/252.33 |
| 5,391,490 | 2/1995 | Varshavsky et al. | 435/224 |
| 5,565,352 | * 10/1996 | Hochstrasser et al. | 435/240.1 |

FOREIGN PATENT DOCUMENTS

WO 91/17245
A1  11/1991  (WO).
WO 92/20804
A1  11/1992  (WO).
WO 93/09235
A2  5/1993  (WO).

OTHER PUBLICATIONS

Anderson, W.F. Nature, vol. 392, Suppl., pp. 25–30 (Apr. 1998).*
Kogi, M., Genbank, Accession No. D38378, Jul. 26, 1994.*
Gupta, Kalpana, et al., "Unp, a mouse gene related to the tre oncogene," *Oncogene*, 8: 2307–2310 (1993).
Onno, Myriam, et al., "Human TRE17 Oncogene Is Generated from a Family of Homologous Polymorphic Sequences by Single–Base Changes," *DNA and Cell Biology*, 12 Number2: 107–118 (1993).
Baker, Rohan T., et al., "Ubiquitin–specific Proteases of Saccharomyces cerevisiae," *J. Biol. Chem.*, 267.No. 32: 23364–23375 (1992).

Gupta, Kalpana, et al., "The Unp proto–oncogene encodes a nuclear protein," *Oncogene*, 9: 1729–1731 (1994).
Nakamura, Tatsuya, et al., "A novel transcriptional unit of the tre oncogene widely expressed in human cancer cells," *Oncogene*, 7: 733–741 (1992).
Tugendreich, Stuart, et al., "CDC27Hs Colocalizes with CDC16Hs to the Centrosome and Mitotic Spindle and Is Essential for the Metaphase to Anaphase Transition," *Cell*, 81:261–268 (Apr. 21, 1995).
King, Randall W., et al., "A 20S Complex Containing CDC27 and CDC16 Catalyzes the Mitosis–Specific Conjugation of Ubiquitin to Cyclin B," *Cell*, 81:279–288 (Apr. 21, 1995).
Murray, Andrew, "Cyclin Ubiquitination: The Destructive End of Mitosis," *Cell*, 81:149–152 (Apr. 21, 1995).
Seufert, Wolfgang, et al., "Role of a ubiquitin–conjugating enzyme in degradation of S– and M–phase cyclins," *Nature*, 373: 78–81 (Jan. 5, 1995).
Papa, Feroz R., and Hochstrasser, Mark, "The yeast DOA4 gene encodes a deubiquitinating enzyme related to a product of the human tre–2 oncogene," *Nature*, 366:313–319 (Nov. 1993).
Scheffner, Martin, et al., "Protein ubiquitination involving an E1–E2–E3 enzyme ubiquitin thioester cascade," *Nature*, 373:81–83 (Jan. 1995).
Irniger, Stefan, et al., "Genes Involved in Sister Chromatid Separation Are Needed for B–Type Cyclin Proteolysis in Budding Yeast," *Cell*, 81:269–277 (Apr. 21, 1995).
Ciechanover, Aaron, "The Ubiquitin–Proteasome Proteolytic Pathway," *Cell*, 79:13–21 (Oct. 7, 1994).
Peters, Jan–Michael, "Proteasomes: protein degradation machines of the cell," *Trends Biochem, Sci*. 19: 377–382 (1994).
Darnell Jr., James E., et al., "Jak–STAT Pathways and Transcriptional Activation in Response to IFNs and Other Extracellular Signaling Proteins," *Science*, 264 No. 5164:1415–1421 (1994).
King, Randall W., et al., "Mitosis in Transition," *Cell*, 79:563–571 (Nov. 18, 1994).

(List continued on next page.)

*Primary Examiner*—George C. Elliott
*Assistant Examiner*—Mark L. Shibuya
(74) *Attorney, Agent, or Firm*—Hamilton, Brook, Smith & Reynolds, P.C.

(57) ABSTRACT

The present invention relates to ubiquitin-specific thiol proteases or deubiquitinating enzymes, referred to as DUB (DeUBiquitinating) enzymes, of eukaryotic origin which are members of a superfamily of deubiquitinating enzymes and which comprise a new subfamily of deubiquitinating enzymes which are similar in size and amino acid sequence to one another. DUB enzymes of the present invention are of eukaryotic origin, such as vertebrate origin, including mammalian (e.g., murine, human) origin, as well as yeast origin. All DUB enzymes of the present invention are inducible by at least one cytokine.

31 Claims, 30 Drawing Sheets

OTHER PUBLICATIONS

Sudakin, Valery, et al., "The Cyclosome, a Large Complex Containing Cyclin–Selective Ubiquitin Ligase Activity, Targets Cyclins for Destruction at the End of Mitosis," *Molecular Biol. of the Cell,* 185–198 (Feb. 1995)

Zhu, Y., et al., "A Hematopoietic–Specific, Interleukin–3 (IL–3)– Inducible, Immediate–Early Gene Encoding a Deubiquitinating Enzyme," 36th Annual Meeting, The American Society of Hematology, (Dec. 2–6, 1994) Abstract No. 872 (Nov. 15, 1994).

Jonnalagadda, Sobhanaditya, et al., "Multiple (α–NH–ubiquitin) Protein Endoproteases in Cells," *J. of Biol. Chemistry,* 264 No. 18: 10637–10642 (1989).

Budarf, M., et al., "Assignment of the Erythropoietin Receptor (EPOR) Gene to Mouse Chromosome 9 and Human Chromosome 19," *Genomics*8: 575–578 (1990).

Mayer, Alan N., and Wilkinson, Keith D., "Detection, Resolution, and Nomenclature of Multiple Ubiquitin Carboxyl–Terminal Esterases from Bovine Calf Thymus," *Biochemistry*28: 166–172 (1989).

Hershko, Avram, and Ciechanover, Aaron, "The Ubiquitin System for Protein Degradation," *Annu. Rev. Biochem.,* 61:761–807 (1992).

Webb, G.C., et al., "Localization of the Human UBA52 Ubiquitin Fusion Gene to Chromosome Band 19p13.1–p12," *Genomics,* 19:567–569 (1994).

Webb, G.C. et al., "Localization of the Human UbB Polyubiquitin Gene to Chromosome Band 17p11.1–17p12," *Am. J. Hum. Genet.,* 46:308–315 (1990).

Tobias, John W., and Varshavsky, Alexander, "Cloning and Functional Analysis of the Ubiquitin–specific Protease Gene UBP1 of *Saccharomyces cerevisiae,*" *J. Biol. Chemistry,* 266 No. 18:12021–12028 (1991).

Candido, E. Peter M., "The Yeast DOA4 Gene Encodes a Deubiquitinating Enzyme Related to a Product of the Human tre–2–Oncogene," *Chemtracts—Biochem. and Molecular Biology,* 5:77–81 (1994).

Little, Melissa H., et al., "Loss of alleles on the short arm of chromosome 11 in a hepatoblastoma from a child with Beckwith–Wiedemann syndrome," *Human Genetics,* 79:186–189 (1988).

Carroll, Martin, et al., "Erythropoietin–induced cellular differentiation requires prolongation of the $G_1$ phase of the cell cycle," *Proc. Natl. Acad. Sci USA,* 92: 2869–2873 (Mar. 1995).

Fujimura, Toshikatsu, et al., "Two Additional Cases of Acute Myeloid Leukemia with t(7;11)) (p15;p15) Having Low Neutrophil Alkaline Phosphatase Scores," *Cancer Genet. Cytogenet.,* 68: 143–146 (1993).

Dexter, T.M., and Spooncer, E., "Growth and Differentiation in the Hemopoietic System," *Ann. Rev. Cell Biol.,* 3:423–41 (1987).

Falquet, Laurent, et al., "A human de–ubiquitinating enzyme with both isopeptidase and peptidase activities in vitro," *FEBS Letters*359: 73–77 (1995).

Xiao, W., et al., "UBP5 Encodes a Putative Yeast Ubiquitin–specific Protease that is Related to the Human Tre–2 Oncogene Product," *Yeast,* 10(11):1497–1502 (1994).

Hochstrasser, M., "Ubiquitin, proteasomes, and the regulation of intracellular protein degradation," *Curr. Opin. Cell Biol.,* 7(2):215–223 (Apr. 1995).

Richardson, P.M., et al., "Molecular–cloning of a cDNA with a novel domain present in the tre-2 oncogene and the yeast–cell cycle regulators BUB2 and cdc16," *Oncogene,* 11:1139–1148 (1995).

Hochstrasser, M., et al., "The DOA pathway: Studies on the Functions and Mechanisms of Ubiquitin–dependent Protein Degradation in the Yeast *Saccharomyces Cerevisiae,*" *Cold Spring Harb Symp Quant Biol.,* 60:503–513 (1995).

Santoli, D., et al., "Synergistic and antagonistic effects of recombinant human interleukin (IL) 3, IL–1 alpha, granulocyte and macrophage colony–stimulating factors (G–CSF and M–CSF) on the growth of GM–CSF–dependent Leukemic cell lines," *J. Immunol.,* 139(10):P3348–3354 (Nov. 15, 1987).

Zhu, Yuan, et al., "DUB–1, a deubiquitinating enzyme with growth–suppressing acctivity," *Proc. Natl. Acad. Sci. U.S.A.,* 93(8):3275–3279 (1996).

\* cited by examiner

```
-183  GAATTCGGCA CGAGGAAAAA CTTCCTTCTG CTCCCTTAGA AGACTCCAGC TAGTTATTTG
-123  AAGAGGTCTT TGTAGACACG GTGGTTGCTC TTTCCTCCCA AGAAGAGATT CTCTAGAAGG
-63   GAAAAACTTC CTTCTGCTCC CTTAGAAGAC TACAGCAAGT TCTTTGAAGA GGTCTTTGGA

-3   GAC ATG GTG GTT GCT CTT TCC TTC CCA GAA GCA GAT CCA GCC CTA TCA
          Met Val Val Ala Leu Ser Phe Pro Glu Ala Asp Pro Ala Leu Ser
           1               5                  10                  15

46   TCT CCT GAT GCC CCA GAG CTG CAT CAG CTG GAT GAA GCT CAG GTG GAG
      Ser Pro Asp Ala Pro Glu Leu His Gln Leu Asp Glu Ala Gln Val Glu
                  20                  25                  30

94   GAG CTA ACT GTC AAT GGA AAG CAC AGT CTG AGT TGG GAG AGT CCC CAA
      Glu Leu Thr Val Asn Gly Lys His Ser Leu Ser Trp Glu Ser Pro Gln
              35                  40                  45

142   GGA CCA GGA TGC GGG CTC CAG AAC ACA GGC AAC AGC TGC TAC CTG AAT
      Gly Pro Gly Cys Gly Leu Gln Asn Thr Gly Asn Ser Cys Tyr Leu Asn
          50                  55                  60

190   GCA GCC CTG CAG TGC TTG ACA CAC ACA CCA CCT CTA GCT GAC TAC ATG
      Ala Ala Leu Gln Cys Leu Thr His Thr Pro Pro Leu Ala Asp Tyr Met
      65                  70                  75

238   CTG TCC CAG GAG CAC AGT CAA ACC TGT TGT CCA GAA GGC TGT AAG
      Leu Ser Gln Glu His Ser Gln Thr Cys Cys Ser Pro Glu Gly Cys Lys
      80                  85                  90                  95

286   TTG TGT GCT ATG GAA GCC CTT GTG ACC CAG AGT CTC CTG CAC TCT CAC
      Leu Cys Ala Met Glu Ala Leu Val Thr Gln Ser Leu Leu His Ser His
                 100                 105                 110
```

FIG. 1A

```
334   TCG GGG GAT GTC ATG AAG CCC TCC CAT ATT TTG ACC TCT GCC TTC CAC
      Ser Gly Asp Val Met Lys Pro Ser His Ile Leu Thr Ser Ala Phe His
                  115             120             125

382   AAG CAC CAG GAA GAT GCC CAG GAG TTT CTC ATG TTC ACC TTG GAA
      Lys His Gln Glu Asp Ala His Glu Phe Leu Met Phe Thr Leu Glu
          130             135             140

430   ACA ATG CAT GAA TCC TGC CTT CAA GTG CAC AGA CAA TCA AAA CCC ACC
      Thr Met His Glu Ser Cys Leu Gln Val His Arg Gln Ser Lys Pro Thr
              145             150             155

478   TCT GAG GAC AGC TCA CCC ATT CAT GAC ATA TTT GGA GGC TGG TGG AGG
      Ser Glu Asp Ser Ser Pro Ile His Asp Ile Phe Gly Gly Trp Trp Arg
      160             165             170             175

526   TCT CAG ATC AAG TGT CTC TGC CAG GGT ACC TCA GAT ACC TAT GAT
      Ser Gln Ile Lys Cys Leu Cys Gln Gly Thr Ser Asp Thr Tyr Asp
                  180             185             190

574   CGC TTC CTG GAC ATC CCC CTG GAT ATC AGC TCA GCT CAG AGT GTA AAG
      Arg Phe Leu Asp Ile Pro Leu Asp Ile Ser Ser Ala Gln Ser Val Lys
                      195             200             205

622   CAA GCC TTG TGG GAT ACA GAG AAG TCA GAA GAG CTA TGT GGA GAT AAT
      Gln Ala Leu Trp Asp Thr Glu Lys Ser Glu Glu Leu Cys Gly Asp Asn
          210             215             220

670   GCC TAC TAC TGT GGT AAG TGT AGA CAG AAG ATG CCA GCT TCT AAG ACC
      Ala Tyr Tyr Cys Gly Lys Cys Arg Gln Lys Met Pro Ala Ser Lys Thr
              225             230             235
```

FIG. 1B

```
 718  CTG CAT GTT CAT ATT GCT CCA AAG GTA CTC ATG GTA GTG TTA AAT CGC
      Leu His Val His Ile Ala Pro Lys Val Leu Met Val Val Leu Asn Arg
      240                 245                 250                 255

766  TTC TCA GCC TTC ACG GGT AAC AAG TTA GAC AGA AAA GTA AGT TAC CCG
      Phe Ser Ala Phe Thr Gly Asn Lys Leu Asp Arg Lys Val Ser Tyr Pro
                      260                 265                 270

814  GAG TTC CTT GAC AAG CCA CTG TAC CTG TCT GAG CCT ACT GGA GGA CCT
      Glu Phe Leu Asp Lys Pro Leu Tyr Leu Ser Glu Pro Thr Gly Gly Pro
              275                 280                 285

862  TTG CCT TAT GCC CTC TAT GCC GTC CTG GTC CAT GAT GGT GCG ACT TCT
      Leu Pro Tyr Ala Leu Tyr Ala Val Leu Val His Asp Gly Ala Thr Ser
          290                 295                 300

910  CAC AGT GGA CAT TAC TTC TGT GTC AAA GCT GGT CAT GGG AAG TGG
      His Ser Gly His Tyr Phe Cys Val Lys Ala Gly His Gly Lys Trp
      305                 310                 315

958  TAC AAG ATG GAT GAT ACT AAA GTC ACC AGG TGT GAT GTG ACT TCT GTC
      Tyr Lys Met Asp Asp Thr Lys Val Thr Arg Cys Asp Val Thr Ser Val
      320                 325                 330                 335

1006  CTG AAT GAG AAT GCC ATT GAC ATG CCA GAG AGA ATA AAT GAG GCC AAC CTC
      Leu Asn Glu Asn Ala Ile Asp Met Pro Glu Arg Ile Asn Glu Ala Asn Leu
                      340                 345                 350

1054  AAA CAG GTC AGT ATT GAC ATG CCA GAG AGA ATA AAT GAG GTT CTT
      Lys Gln Val Ser Ile Asp Met Pro Glu Arg Ile Asn Glu Val Leu
              355                 360                 365

1102  GAC CCT GAA TAC CAG CTG AAG TCA CGG AGA AAA AAG CAT AAG AAG
      Asp Pro Glu Tyr Gln Leu Lys Ser Arg Arg Lys Lys His Lys Lys
          370                 375                 380
```

```
1150  AAA AGC CCT TTC ACA GAA GAT TTA GGA GAG CCC TGC GAA AAC AGG GAT
      Lys Ser Pro Phe Thr Glu Asp Leu Gly Glu Pro Cys Glu Asn Arg Asp
      385                 390                 395

1198  AAG AGA GCA ATT AAA GAA GAG ACC TCC TTA GGA AAG GGG AAA GTG CTT CAG
      Lys Arg Ala Ile Lys Glu Glu Thr Ser Leu Gly Lys Gly Lys Val Leu Gln
      400                 405                 410                 415

1246  GAA GTG AAC CAC AAG AAA GCT GGG CAG AAA CAC GGG AAT ACC AAA CTC
      Glu Val Asn His Lys Lys Ala Gly Gln Lys His Gly Asn Thr Lys Leu
                      420                 425                 430

1294  ATG CCT CAG AAA CAG AAC CAC CAG AAA GCT GGG CAG AAC CTC AGG AAT
      Met Pro Gln Lys Gln Asn His Gln Lys Ala Gly Gln Asn Leu Arg Asn
                      435                 440                 445

1342  ACT GAA GTT GAA CTT GAT CTG CCT GAT GCA ATT GTG ATT CAC CAG
      Thr Glu Val Glu Leu Asp Leu Pro Asp Ala Ile Val Ile His Gln
                      450                 455                 460

1390  CCC AGA TCC ACT GCA AAC TGG GGC AGG GAT TCT CCA GAC AAG GAG AAT
      Pro Arg Ser Thr Ala Asn Trp Gly Arg Asp Ser Pro Asp Lys Glu Asn
      465                 470                 475

1438  CAA CCC TTG CAC AAT GCT GAC AGG CTC ACC TCT CAG GGC CCT GTG
      Gln Pro Leu His Asn Ala Asp Arg Leu Thr Ser Gln Gly Pro Val
      480                 485                 490                 495

1486  AAC ACT TGG CAG CTC TGT AGA CAG GAA GGG AGA CGA AGA TCG AAG
      Asn Thr Trp Gln Leu Cys Arg Gln Glu Gly Arg Arg Arg Ser Lys
                      500                 505                 510

1534  GGG CAG AAC AAG AAG CAA AAG CAG GGG CAG AGG CTT CTG CTT GTT TGC
      Gly Gln Asn Lys Lys Gln Lys Gln Gly Gln Arg Leu Leu Leu Val Cys
                      515                 520                 525
```

```
1579  TAGTGATCAC CCACCCACTC ACACAGGCTC CTGTGGACAC ACTGTTGACC CAAGGTGCCT
1639  GGAACAAGAG GTTTGGATCT CTGTTTCAGG CAGGGACAAT GCCTCACCCT TCACGTGGGG
1699  TCCACCTATC CTCTGGGCCC TTGCCTGTTT TTGCTGACTG ACTCTCTGAT TGTTTGAATG
1759  TGGAAAAAAA GTGCCCAGGA TGTTGGTACA GGTTAAAGAC AAGAAGCTGG ACACCCGGAG
1819  GAGGTCTGAA TAGCCCTCTC TGCAACTCAT GGAATCTGAG CAGCATAGAG ACTAAATCAC
1879  CACACTGGAG CTTTCTTTTC TTTTCTTTTC TTTTCTTTTC TTTTCTTTTC TTTCTTTTC
1939  TCTTCTCTTC TCTTCTCTTC TCTTCTCTTC TCTTCTCTTC TCTTCTCTTC TCTTCTCTTC
1999  TCTCCTCTCC TCTCCTCTCC TCTCCTCTCC TCTCCTCTCC TCTCCTTTCC TTTCCTTTCC
2059  TTTCCTTTTT TTTTAAATTT ATTTTTTGTT ATTAGATATT TTCTTTATTT ACATTTCAAA
2119  TGCTATCCCA AAAGTTCCCT ATACCCTCCC CCAACTCTGC CACCCTACCC ACCCACTCCC
2179  ACTTCTTGGC TCTGGCATTT CCCTGTACTG GGGCATATAA AGTTTGCAAT ACCAAAGGGC
2239  CTCTCTTCCC AATGATGGCC AACTAGGTCA CCTTCTGCTA CATATGCAGC TAGAGACCCT
2299  AAGAAAACAC ACTGGAACTC TTGAGGTTTG GAGTTTTCGC TCAGGCAAAC AAGTTGCTTT
2359  TCAACTGCCC TTTCTAACCT CTTACCCAGA AAATGTGTAG TTCACCCTGT AGAGATAGAT
2419  GCTCTTATTC TTAGTGTGTG ATCAACAGTT CTTTGGTCAA ATAAATTCTG TTACTTCACA
2479  AAAAAAAAAA AAA   2491
```

FIG. 1E

Cys domain

| | | | | | | | | | | | | | | | |
|---|---|---|---|---|---|---|---|---|---|---|---|---|---|---|---|
| tre-2 | 216 | G | L | S | N | L | N | T | C | F | M | N | S | S | I | Q | C | V | 233 |
| Unp | 135 | G | L | G | N | L | N | T | C | F | M | N | S | S | L | Q | C | L | 152 |
| Doa4 | 563 | G | L | E | N | L | G | S | C | Y | M | N | A | A | H | Q | C | I | 580 |
| H-Dub | 52 | G | L | Q | N | T | G | N | C | Y | L | N | A | L | L | Q | C | L | 69 |

His domain

| | | | | | | | | | | | | | | | | | | | |
|---|---|---|---|---|---|---|---|---|---|---|---|---|---|---|---|---|---|---|---|
| tre-2 | 995 | Y | N | L | Y | A | I | S | C | H | S | G | H | Y | I | T | Y | A | K | NP-NC | K | WY | CY | N | D | SSCEEL-HPDE | I | DTDS | AYILFY | 1049 |
| Unp | 696 | Y | D | L | I | A | V | S | N | H | Y | G | A | M | G | V | T | A | Y | A | K | NRLNG | K | WY | YF | D | D | SSVSLA-SEDQ | I | VTKA | AYVLFY | 751 |
| Doa4 | 864 | Y | E | L | Y | G | V | A | C | H | F | G | T | L | Y | G | T | A | Y | V | K | KGLKK | G | WI | YF | D | D | TKYKPVKNKAD | A | INSN | AYVLFY | 920 |
| H-Dub | 290 | Y | A | L | Y | A | V | L | V | H | D | G | A | T | SHS | FC | Q | V | K | AG-HG | K | WY | KM | D | D | TKVTRC-DVTS | V | LNEN | AYVLFY | 345 |

Myc homology

| | | | | | | | | | | | | | | | | |
|---|---|---|---|---|---|---|---|---|---|---|---|---|---|---|---|---|---|
| Myc | 313 | P | S | T | R | K | D | Y | P | A | K | R | A | K | L | D | S | G | R | V | L | K | Q | I | S | N | N | R | 340 |
| H-Dub | 394 | P | C | E | N | R | D | K | R | A | I | K | E | T | S | L | G | K | G | K | V | L | Q | E | V | N | H | K | K | 421 |

FIG. 2

```
-1541   ACTAGTAAGG ATATAACAGG AAATAATGAC TAAGACTGTG GTATGAAGGT AATTCACTGA
-1481   TAGTAGAAAT GGAAAAAAAA GTATCAGGTT TCACTGCTTC ATAAGGAGAT ACAACAGTGA
-1421   CTAAGACCGG TTTTTCTAAA CATGTGTGGT TATTGTTTTG AGTGTCTGTG TGTGTGTTTG
-1361   ATTCTTTTCT TTTCTTTTCT TTTCTTTTCT TTTCTTTTCT TTTCTTTTCT TGAGGTAATG
-1301   AAAGCCAATG GTCATGAGTT GAAGCGATAA TAGGGTGATT GATAACAAGC TCAAGGTCAG
-1241   TATGGCGAAG GAGCCATATT GTCTCAAAAA CATACAAGAA GGGAGGATTT GCCTGCTTTG
-1181   GTCCACCTAG AGTGAGTCTT ATTACTGAAG TAAGGCTGAA TGAGCATAAT GGAGCTAATT
-1121   GGGTGATTGA ATCATCTACT CAGCAGTTAC AACTTTAGAG GCAATGGCAC TATAAAAATG
-1061   TTTTTTGTTT TGTTTGTTT TTCCCAGATA GGGTTTTGCT GTGTAGCCCT GGCTGTCTTG
-1001   GACCTCACTC TGTAGACCAG GGTAGCCTCC AACTGAGAAA CTGCCCTGCA TCTGCCTCCC
-941    AAGTGCTGGG ATCACAAGGT TGCATAACAA ATGCTTTGCA AAATTTGTA CAAGTAATTA
-881    GAGAGTTAGT TGTGGGTAAA ACACATCAAA ATGCTTTGCA TTCTTGAGTG CTGATAATAC
-821    ACTAAAGAAG CAGAGTATAG ATTCAAGGTC ATTTTTTTT TTTTTTTTA GAGAATCAAC
-761    AGTCTACTTA CTGGACTAGA TGTCTTCATA GACCATATGA CTTTGACTGG AAATGTGTCT
-701    TCTACAGAGA AAGTGGAGAG AGAGAGAGAA AAAGAAGGAA GGAAGGAAGG AAGGAAGGAA
-641    GGAAGGACGG AAGGAAGGAA GAGAAGGAGA TAGAGAGAGA GAGAGACAGA GAAAGAGAGA
```

FIG. 4A

-581  GAGAGAGAGA TAAAGAAAGA AAGGAAGGAA GGAAGGAAGG AAGGACGGAC GGAAGGAAGG
-521  AAGAGAGAGA GATAGAGAGA GAGAAAGAGA GAGAGATAAA GAAAGGAAGG
-461  AAGGAAGGAA GGAAGGAAGG AAGGAAGGAA GGAAGGAAGG AAGGAAGAAA GAAAGGGCAA
-401  AAGGGAAGGA AAACCAGGCC TAGGCTGTTT ATACTGGTTC TGTGTGGTTA GCAAGTAAT
-341  GGGAACTCTT GTATGGCATG TATAGTCATC TATTTGACAT AATTTTGTAA CTTTATTCCA
-281  AATAAAACCC AAACTTAAGA CACCTAGGAA ATTGGAGCTA AATTCAGGGA AATGCACTCC
-221  AAAGAGATGA CATTTCTGAG CTGTCCTGCA GAAACCACAC CCAACTTGTG AGAGGCTTGT
-161  CTGGGATTGG CTGTCCTGGG AAGACTGTAG GCGTGGTCAC AAGACTGGAG TTTAAAAGAC
-101  TGAGCATTTG TCCTCACTTG CACAGATTCT CTAGAAGGGA AAAACTTCCT TCTGCTCCCT
-41   TAGAAGACTA CAGCAAGTTC TTTGAAGAGG TCTTTGGAGA CATGGTGGTT GCTCTTTCC...EXON 1...
                                                  M   V   V   A   L   S

FIG. 4B

```
PALSSPDAPELHQDEAQVVEELTVNGKHSLSWESPQGPGCGLQNTGNSCYLNAALQCLTH          DUB-1
PALSSPDAPELHQ EAQVVE LT.NGK SLSWESP.GPGCGLQNTGNSCYLNAALQCLTH          Consensus
PALSSPDAPELHQFEAQVVEVLTTNGKFSLSWESP.GPGCGLQNTGNSCYLNAALQCLTH          DUB-3

TPPLADYMLSQEHSQTCCSPEGCKLCAMEALVTQSLLHSHGDVMKPSHILTSAFHKHQQ
TPPLADYMLSQEHSQTCCSPEGCK:CAME. VTQSL S GDVMKPS:ILTSAFHKHQQ
TPPLADYMLSQEHSQTCCSPEGCKMCAMEECVTQSL.LSL-GDVMKPSQILTSAFHKHQQ

EDAHEFLMFTLETMHESCLQVHRQSKPTSEDSSPIHDIFGGWWRSQIKCLLCQGTSDTYD
EDAHEFLMFTLETMHESCLQVHRQS.PT::D:SPIHDIFGGWWRSQIKCL   .GTS:T:D
EDAHEFLMFTLETMHESCLQVHRQSDPTPQDTSPIHDIFGGWWRSQIKCLX-AGTSHTFD

RFLDIPLDISSAQSVKQALWDTEKSEELCGDNAYYCGKCRQKMPASKTLHVHIAPKVLMV
.FLD:PLDISSAQSV:QALWDT.KSEEL G:NAYYCG:CRQKMPASKTLHVHIAPKVL::
PFLDVPLDISSAQSVNQALWDTGKSEELLGENAYYCGRCRQKMPASKTLHVHIAPKVLLL

VLNRFSAFTGNKLDRKVSYPEFLDLKPYLSEPTGGPLPYALYAVLVHDGATSHSGHYFCC
VL:RFSAFTGNKLDRKVSYPEFLDLKPYLSEPTGGPLPYALYAVLVHDGATS:SGHYFCC
VLKRFSAFTGNKLDRKVSYPEFLDLKPYLSEPTGGPLPYALYAVLVHDGATSNSGHYFCC

VKAGHGKWYKMDDTKVTRCDVTSVLNENAYVLEYVQQANLKQVSIDMPEGRINEVLDPEY
VKAGHGKWYKMDDTKVTRCDVTSVLNENAYVLFYVQQA:LKQVSIDMPEGR::EVLDP.Y
VKAGHGKWYKMDDTKVTRCDVTSVLNENAYVLFYVQQADLKQVSIDMPEGRVHEVLDPKY

QLKKSRRKKHKKKSPFTEDLGEPCENRDKRAIKETSLGKGKVLQEVNHKKAGQKHGNTKL
QLKKSRRKKHK.:.. : GE    ::D R : .L.G.. EVNH.KAG .HGNTKL
QLKKSRRKKHKMQCHCSFGAGEGTREKDGRREQRNLLREGSA-SEVNHEKAGSEHGNTKL

MPQKQNHQKAGQNLRNTEVELDLPADAIVIHQPRSTANWGRD-SPDKENQP-LHNADRLL
:PQ.QNHQ:AGQNLRNTEVELDLP.D.IVIHQPRSTANWG : S: KENQP  N:DR:L
VPQEQNHQRAGQNLRNTEVELDLPVDVIVIHQPRSTANWGXGCSSIKENQPWXTNGDRFL

TSQGPVNTWQLCRQEGRRRSKKGQNKNKQG
TSQG :::  QLC.Q.GR RSKKG:NK KQG
TSQGLMSPGQLCSQGGR.RSKKGKNKYKQG
```

FIG. 8

```
CYS Domain
       G  L  Q  N  T  G  N  S  C  Y  L  N  A  A  L  Q  C  L              Majority
  1    G  L  Q  N  T  G  N  S  C  Y  L  N  A  A  L  Q  C  L              DUB-1
  1    G  L  Q  N  T  G  N  S  C  Y  L  N  A  A  L  Q  C  L              DUB-3
  1    G  L  Q  N  T  G  N  S  C  Y  L  N  A  A  L  Q  C  L              DUB-2

HIS Domain
       Y  A  L  Y  A  V  L  V  H  D  G  A  T  S  G  H  Y  F  C  C  V  K  A  G  H  G  K  W  Y  K  M  D  D  T  K  V  T  R    Majority
  1    Y  A  L  Y  A  V  L  V  H  D  G  A  T  S  G  H  Y·F  C  C  V  K  A  G  H  G  K  W  Y  K  M  D  D  T  K  V  T  R    DUB-1
  1    Y  A  L  Y  A  V  L  V  H  D  G  A  T  S  N  H  Y  F  C  C  V  K  A  G  H  G  K  W  Y  K  M  D  D  T  K  V  T  R    DUB-3
                                                                                                                            T14 cys   DUB-1
                                                                                                                            9-2 cys   DUB-3
                                                                                                                            cl. 4 cys DUB-2
121    C  D  V  T  S  V  L  N  E  N  A  Y  V  L  F  Y                                                                       DUB-1
121    C  D  V  T  S  V  L  N  E  N  A  Y  V  L  F  Y                                                                       DUB-3

C-Terminal Domain
       K  L  X  P  Q  E  Q  N  H  Q  K  A  G  Q  N  L  R  N  T  E  V  E  L  D  L  P  A  D  A  I            Majority
  1    K  L  M  P  Q  K  Q  N  H  Q  K  A  G  Q  N  L  R  N  T  E  V  E  L  D  L  P  A  D  A  I            T14 (IL3) 1471 Protein
  1    K  L  P  P  Q  E  E  N  H  Q  K  A  G  Q  N  L  R  N  T  E  G  E  L  D  L  P  A  D  A  H            Cl. 4 1471 Protein
  1    K  L  V  P  Q  E  Q  N  H  Q  R  A  G  Q  N  S  R  N  T  E  V  E  L  D  L  P  V  D  A  I            9-2 1471 Protein V  I  H  Q  P  R  S  T  A  N  W  G  R  D  A  P  D  K  E  N  Q  P  W  H  N  A  D  R  L  L            Majority
 31    V  I  H  Q  P  R  S  T  A  N  W  G  R  D  A  P  D  K  E  N  Q  P  L  H  N  A  D  R  L  L            T14 (IL3) 1471 Protein
 31    V  I  H  Q  L  R  S  T  E  N  W  G  R  D  S  P  D  K  E  N  Q  P  W  H  N  A  D  R  L  L            Cl. 4 1471 Protein
 31    V  I  H  Q  P  R  S  T  A  N  W  G  T  D  A  P  D  K  E  N  Q  Q  W  H  N  G  D  R  L  L            9-2 1471 Protein T  S  Q  G  P  V  N  T  G  Q  L  C  R  Q  E  G  R  R  S  K  K  G  X  N  K  N  K  Q  G               Majority
 61    T  S  Q  G  P  V  N  T  G  Q  L  C  R  Q  E  G  R  R  S  K  K  G  Q  N  K  N  K  Q  G               T14 (IL3) 1471 Protein
 61    T  T  Q  G  P  V  N  T  G  Q  L  C  R  Q  E  G  R  R  S  K  K  G  K  N  K  N  K  Q  G               Cl. 4 1471 Protein
 61    T  S  Q  G  L  M  S  P  G  Q  L  C  S  Q  G  G  R  -  R  S  K  K  G  K  N  K  N  K  Q               9-2 1471 Protein Q  R  L  L  L  V  C                                                                                 Majority
 91    Q  R  L  L  L  V  C  -  -                                                                           T14 (IL3) 1471 Protein
 91    Q  R  L  L  L  V  C  .  .                                                                           Cl. 4 1471 Protein
 90    G  Q  R  L  L  L  V  C  .                                                                           9-2 1471 Protein
```

FIG. 9

```
CCAGCACTATCATCTCCTGATGCCCCAGAGCTGCATCAGTTTGAAGCTCAGGTGGTGGAGGTGCTAACTA
GGTCGTGATAGTAGAGGACTACGGGGTCTCGACGTAGTCAAACTTCGAGTCCACCACCTCCACGATTGAT   70
  P  A  L  S  S  P  D  A  P  E  L  H  Q  F  E  A  Q  V  V  E  V  L  T

CCAATGGAAAGTTCAGTCTGAGTTGGGAGAGTCCCTAAGGACCAGGATGCGGGCTCCAGAACACAGGCAA
GGTTACCTTTCAAGTCAGACTCAACCCTCTCAGGGATTCCTGGTCCTACGCCCGAGGTCTTGTGTCCGTT  140
  T  N  G  K  F  S  L  S  W  E  S  P  .  G  P  G  C  G  L  Q  N  T  G  N

CAGCTGCTACCTGAACGCAGCCCTGCAGTGCTTGACACACACACCACCTCTAGCTGACTACATGCTGTCC
GTCGACGATGGACTTGCGTCGGGACGTCACGAACTGTGTGTGGTGGAGATCGACTGATGTACGACAGG   210
    S  C  Y  L  N  A  A  L  Q  C  L  T  H  T  P  P  L  A  D  Y  M  L  S

CAGGAGCACAGTCAAACCTGTTGTTCCCCAGAAGGTTGTAAGATGTGTGCTATGGAAGAATGTGTGACCC
GTCCTCGTGTCAGTTTGGACAACAAGGGGTCTTCCAACATTCTACACACGATACCTTCTTACACACTGGG  280
  Q  E  H  S  Q  T  C  C  S  P  E  G  C  K  M  C  A  M  E  E  C  V  T

AGAGTCTTTGACTCTCACTGGGGGATGTCATGAAGCCCTCCCAGATTTTGACCTCTGCCTTCCACAAGCA
TCTCAGAAACTGAGAGTGACCCCCTACAGTACTTCGGGAGGGTCTAAAACTGGAGACGGAAGGTGTTCGT  350
  Q  S  L  .  L  S  L  G  D  V  M  K  P  S  Q  I  L  T  S  A  F  H  K  H

CCAGCAGGAAGATGCCCATGAGTTTCTCATGTTCACCTTGGAAACAATGCATGAATCCTGCCTTCAAGTG
GGTCGTCCTTCTACGGGTACTCAAAGAGTACAAGTGGAACCTTTGTTACGTACTTAGGACGGAAGTTCAC  420
  Q  Q  E  D  A  H  E  F  L  M  F  T  L  E  T  M  H  E  S  C  L  Q  V

CACAGACAATCAGATCCCACCCCTCAGGATACGTCACCCATTCATGACATATTTGGAGGCTGGTGGAGGT
GTGTCTGTTAGTCTAGGGTGGGGAGTCCTATGCAGTGGGTAAGTACTGTATAAACCTCCGACCACCTCCA  490
  H  R  Q  S  D  P  T  P  Q  D  T  S  P  I  H  D  I  F  G  G  W  W  R

CTCAGATCAAGTGTCTCNATGCAGGCACCTCACATACCTTCGATCCCTTCCTGGATGTCCCCCTGGATAT
GAGTCTAGTTCACAGAGNTACGTCCGTGGAGTGTATGGAAGCTAGGGAAGGACCTACAGGGGGACCTATA  560
  S  Q  I  K  C  L  ?  A  G  T  S  H  T  F  D  P  F  L  D  V  P  L  D  I
```

FIG. 10A

```
CAGCTCAGCTCAGAGTGTAAATCAAGCCTTGTGGGATACAGGCAAGTCAGAAGAGCTACTTGGAGAGAAT
                                                                      630
GTCGAGTCGAGTCTCACATTTAGTTCGGAACACCCTATGTCCCTTCAGTCTTCTCGATGAACCTCTCTTA
  S  S  A  Q  S  V  N  Q  A  L  V  D  T  G  K  S  E  E  L  L  G  E  N

GCCTACTACTGTGGTAGGTGTAGACAGAAGATGCCAGCTTCTAAGACCCTGCATGTTCATATTGCTCCAA
                                                                      700
CGGATGATGACACCATCCACATCTGTCTTCTACGGTCGAAGATTCTGGGACGTACAAGTATAACGAGGTT
  A  Y  Y  C  G  R  C  R  Q  K  M  P  A  S  K  T  L  H  V  H  I  A  P

AGGTACTCCTGCTAGTGTTAAAGCGCTTCTCAGCCTTCACGGGTAACAAGTTAGACAGAAAAGTAAGCTA
                                                                      770
TCCATGAGGACGATCACAATTTCGCGAAGAGTCGGAAGTGCCCATTGTTCAATCTGTCTTTTCATTCGAT
  K  V  L  L  L  V  L  K  R  F  S  A  F  T  G  N  K  L  D  R  K  V  S  Y

CCCGGAGTTCCTTGACCTGAAGCCATACCTGTCTGAGCCTACTGGAGGACCTTTGCCTTATGCCCTCTAT
                                                                      840
GGGCCTCAAGGAACTGGACTTCGGTATGGACAGACTCGGATGACCTCCTGGAAACGGAATACGGGAGATA
   P  E  F  L  D  L  K  P  Y  L  S  E  P  T  G  G  P  L  P  Y  A  L  Y

GCCGTCCTGGTCCATGATGGTGCCGACTTCTAACAGTGGACATTACTTCTGTTGTGTCAAAGCTGGTCATG
                                                                      910
CGGCAGGACCAGGTACTACCACGCTGAAGATTGTCACCTGTAATGAAGACAACACAGTTTCGACCAGTAC
  A  Y  L  V  H  D  G  A  T  S  N  S  G  H  Y  F  C  C  V  K  A  G  H

GGAAGTGGTACAAGATGGATGATACTAAGGTCACCAGGTGTGATGTGACTTCTGTCCTGAATGAGAATGC
                                                                      980
CCTTCACCATGTTCTACCTACTATGATTCCAGTGGTCCACACTACACTGAAGACAGGACTTACTCTTACG
   G  K  W  Y  K  M  D  D  T  K  V  T  R  C  D  V  T  S  V  L  N  E  N  A

CTATGTGCTCTTCTATGTGCAGCAGGCCGACCTCAAACAGGTCAGTATTGACATGCCAGAGGGCAGAGTA
                                                                      1050
GATACACGAGAAGATACACGTCGTCCGGCTGGAGTTTGTCCAGTCATAACTGTACGGTCTCCCGTCTCAT
   Y  V  L  F  Y  V  Q  Q  A  D  L  K  Q  V  S  I  D  M  P  E  G  R  V

CATGAGGTTCTTGACCCTAAATACCAGCTGAAGAAATCCCGGAGAAAAAAGCATAAGATGCAATGCCATT
                                                                      1120
GTACTCCAAGAACTGGGATTTATGGTCGACTTCTTTAGGGCCTCTTTTTTTCGTATTCTACGTTACGGTAA
   H  E  V  L  D  P  K  Y  Q  L  K  K  S  R  R  K  K  H  K  M  Q  C  H
```

FIG. 10B

```
GCTCATTTGGTGCGGGAGAAGGCACTCGCGAAAAAGATGGAAGAAGAGAGCAAAGAAACCTCCTTAGGGA
CGAGTAAACCACGCCCTCTTCCGTGAGCGCTTTTTCTACCTTCTTCTCTCGTTTCTTTGGAGGAATCCCT   1190
 C  S  F  G  A  G  E  G  T  R  E  K  D  G  R  R  E  Q  R  N  L  L  R  E

GGGAAGTGCCTCAGAAGTGAACCACGAGAAAGCTGGGTCAGAACATGGGAATACCAAACTCGTGCCTCAG
CCCTTCACGGAGTCTTCACTTGGTGCTCTTTCGACCCAGTCTTGTACCCTTATGGTTTGAGCACGGAGTC   1260
 G  S  A  S  E  V  N  H  E  K  A  G  S  E  H  G  N  T  K  L  V  P  Q

GAACAGAACCACCAGAGAGCTGGGCAGAACCTCAGGAATACTGAAGTTGAACTTGATCTGCCTGTTGATG
CTTGTCTTGGTGGTCTCTCGACCCGTCTTGGAGTCCTTATGACTTCAACTTGAACTAGACGGACAACTAC   1330
 E  Q  N  H  Q  R  A  G  Q  N  L  R  N  T  E  V  E  L  D  L  P  V  D

TCATTGTGATTCACCAGCCCAGATCCACAGCAAACTGGGGCNACGGATGCTCCAGTATCAAAGAGAATCA
AGTAACACTAAGTGGTCGGGTCTAGGTGTCGTTTGACCCCGNTGCCTACGAGGTCATAGTTTCTCTTAGT   1400
 V  I  V  I  H  Q  P  R  S  T  A  N  W  G  ?  G  C  S  S  I  K  E  N  Q

ACCCTGGNTCACNAATGGTGACAGGTTCCTCACCTCTCAGGGCCTCATGAGCCCTGGGCAGCTCTGTAGT
TGGGACCNAGTGNTTACCACTGTCCAAGGAGTGGAGAGTCCCGGAGTACTCGGGACCCGTCGAGACATCA   1470
 P  W  ?  T  N  G  D  R  F  L  T  S  Q  G  L  M  S  P  G  Q  L  C  S

CAGGGTGGGAGATGAAGATCGAAGAAGGGGAAGAACAAGTACAAGCAAGGGCA
GTCCCACCCTCTACTTCTAGCTTCTTCCCCTTCTTGTTCATGTTCGTTCCCGT   1523
 Q  G  G  R  .  R  S  K  K  G  K  N  K  Y  K  Q  G  H
```

FIG. 10C

```
                                                                      DUB-1
                                                                      Consensus
                                                                      D38378

SFPEADPALSSPDAPELHQDEAQVVEELTVNGKHSLSWESPQGPGCGLQNTGNSCYLNAA
S:PE .P LS. .   :L :D A.V. :L: . .K :LS  .P.: K :LS  GLQN GN:CY:NA:
SLPEKSP-LSCETRVDLCDDLAPVARQLAPREKLPLSSRRPAAVGAGLQNMGNTCYVNAS

LQCLTHTPPLADYMLSQEHSQTCCSPEGCKLCAMEALVTQSLLHSHSGDVMKPSHILTSA
L: LT.TPPLA:YMLS:EHSQTC ...GC.LC:M:A :T::L H ::G:V::PS: L:::
LEWLTYTPPLANYMLSREHSQTCHRHKGCMLCTMQAHITRAL-H-NPGHVIQPSQALAAG

FHKHQQEDAHEFLMFTLETMHESCLQVHRQSKPTSEDSSPIHDIFGGWRSQIKCLLCQG
FH: :QEDAHEFLMFT:::M...:CL. H:Q . . S.D:: IH:IFGG.WRSQIKCL C:G
FHRGKQEDAHEFLMFTVDAMKKACLPGHKQVDHHSKDTTLIHQIFGGYWRSQIKCLHCHG

TSDTYDRFLDIPLDISSAQSVKQALWDTEKSEELCGDNAYYCGKCRQKMPASKTLHVHIA
.SDT:D. :LDI:LDI  :AQSV:QAL :  K:EEL G:NAY.CG C Q: PASKTL :H. :
ISDTFDPYLDIALDIQAAQSVQQALEQLVKPEELNGENAYHCGVCLQRAPASKTLTLHTS

PKVLMVLNRFSAFTGNKLDRKVSYPEFLDLKPYLSEPTGGPLPYALYAVLVHDGATSHS
:KVL::VL:RFS. TGNK:. ::V YPE LD::PY:S...GPL Y.LYAVLVH.G :.H:
AKVLILVLKRFSDVTGNKIAKNVQYPECLDMQPYMSQQNTGPLVYVLYAVLVHAGWSCHN

GHYFCCVKAGHGKWYKMDDTKVTRCDVTSVLNENAYVLFYVQQANLKQVSIDMPEGRINE
GHYF..VKA :G:WYKMDD:.VT ...:TSVL:::AYVLFY:Q::: .: S .:: GR
GHYFSYVKAQEGQWYKMDDAEVTASSITSVLSQQAYVLFYIQKSEWERHSESVSRGREPR

VLDPEYQLKKSRRKKHKKKSPFTEDLGEPCENRDKRAIKETSLGKGKVLQEVNHKKAGQK
.L::E   :::: .  K:. P  :: E  E: .RA. :E::L:. K LQE
ALGAEDTDRRATQGELKRDHPCLQA- PELDEHLVERATQESTLDHWKFLQE--------

HGNTKLMPQKQNHQKAGQNLRNTEVELDLPADAIVIHQPRSTANWGRDSPDKENQPLHNA
         QN. K:. N:R:   VE .LP:D.:VIHQ::  . .: P:::: L: :
--------QNKTKPEFNVRK--VEGTLPPDVLVIHQSKYKCGMKNHHPEQQSSLLNLS

DRLLTSQGPVNTWQLCRQEGRRRSKKGQNKNKQGQRLLLVC
. T Q.::NT L .  GR R..KG  KNK:::R LLVC
STTPTHQESMNTGTLASLRGRARRSKG--KNKHSKRALLVC
```

FIG. 11

AACAAGCAGAAGCCCTCTGCCCTTGCTTGTTCTTGTTCTTC 40
CCCTTCTTCGATCTTACATCTCCGACCCTGACTACAGAGC 80
TGCCCAGGGCTCATGAGGCCTGAGAGGTAGGAGCCTGTCA 120
CCATTGTGCCAGGGTTGATTTCT 143

FIG. 12

GAAGCCTCTGCCCTTGCTTGGTCTTGTTCTTCCCCTTCTT 40
CGATCTTCGTCTCCCACCCTGACAACAGAGCTGCCCAGGG 80
CTCGTGAGGCCTGAGAGTCGAGGAGCCTGTCAGCATTGTG 120
CCGGGTTGATTCTCCTTGTCTGGAGCATCCCTGTCCCAGT 160
TTGCAGTGGATCTGGGCTGGTGAATCACAATTGCATCAGC 200
AGGCAGATCAAGTTCACCTTCGGATCCC 228

FIG. 13

```
GCTTTGCAGA AACCACACCC AAATTGGGAG AAGCTTGTCT GGGATTGGCT GTCCTTGGAA    60

GACTGTAGGC GTGGTCACAA GACTGGAGTA TAAAAGACTG AGCATTTGTC CTCACTTGCA   120

GAGATTCTCT GGAGGGAAAG ACTTCCTTCT GCTCCCTTAG AAGACTACAG CAAGTTATTT   180

GAAGAGGTCT TTGGAGAC ATG GTG GTT TCT CTT TCC TTC CCA GAG CAA GAT    231
                    Met Val Val Ser Leu Ser Phe Pro Glu Gln Asp
                     1                   5                    10

CCA GCC CTA TCT CCT GGT GCC CAA CAG CTG CAT CAG CTG AAG CCA GAT GCT  279
Pro Ala Leu Ser Pro Gly Ala Gln Gln Leu His Gln Leu Lys Pro Asp Ala
                15                  20                  25

CAG GTA GTG GAG CTA ACT GCC AAT GAC AAG CCC AGT CTG AGT TGG          327
Gln Val Val Glu Leu Thr Ala Asn Asp Lys Pro Ser Leu Ser Trp
        30                  35                  40

GAA TGT CCC CAA GGA CCA GGA CCA GGA CTT CAG AAC ACA GGC AAC AGC      375
Glu Cys Pro Gln Gly Pro Gly Gly Leu Gln Asn Thr Gly Asn Ser
        45                  50                  55

TGC TAC CTG AAT GCA GCC CTG CAG TGC TTG ACA CAC ACA CCT CTA          423
Cys Tyr Leu Asn Ala Ala Leu Gln Cys Leu Thr His Thr Pro Leu
        60                  65                  70              75
```

FIG. 14A

```
GCT GAC TAC ATG CTG TCC CAG GAG TAC AGT CAA ACC TGT TCC CCA                              471
Ala Asp Tyr Met Leu Ser Gln Glu Tyr Ser Gln Thr Cys Ser Pro
            80                          85                  90

GAA GGC TGT AAG ATG TGT GCT ATG GAA GCC CAT GTA ACC CAG AGT CTC                          519
Glu Gly Cys Lys Met Cys Ala Met Glu Ala His Val Thr Gln Ser Leu
            95                         100                     105

CTG CAC TCT CAC TCG GGG GAT GTC ATG AAG CCC TCC CAG ATT TTG ACC                          567
Leu His Ser His Ser Gly Asp Val Met Lys Pro Ser Gln Ile Leu Thr
            110                         115                     120

TCT GCC TTC CAC AAG CAC CAG CAG GAA GAT GCC CAT GAG TTT CTC ATG                          615
Ser Ala Phe His Lys His Gln Gln Glu Asp Ala His Glu Phe Leu Met
            125                         130                     135

TTC ACC TTG GAA ACA ATG CAT GAA TCC TGC CTT CAA GTG CAC AGA CAA                          663
Phe Thr Leu Glu Thr Met His Glu Ser Cys Leu Gln Val His Arg Gln
            140                         145                     150             155

TCA GAA GAC CCC ACC TCT GAG GAC AGC TCA CCC ATT CAT GAC ATA TTT GGA                      711
Ser Glu Asp Pro Thr Ser Glu Asp Ser Ser Pro Ile His Asp Ile Phe Gly
            160                         165                     170
```

FIG. 14B

```
GGC TTG TGG AGG TCT CAG ATC AAG TGT CTC CAT TGC CAG GGT ACC TCA              759
Gly Leu Trp Arg Ser Gln Ile Lys Cys Leu His Cys Gln Gly Thr Ser
        175                         180                    185

GAT ACA TAT GAT CGC TTC CTG GAT GTC CCC CTG GAT ATC AGC TCA GCT              807
Asp Thr Tyr Asp Arg Phe Leu Asp Val Pro Leu Asp Ile Ser Ser Ala
        190                         195                    200

CAG AGT GTA AAT CAA GCC TTG TGG GAT ACA GAG AAG TCA GAA GAG CTA              855
Gln Ser Val Asn Gln Ala Leu Trp Asp Thr Glu Lys Ser Glu Glu Leu
        205                         210                    215

CGT GGA GAG AAT GCC TAC TAC TGT GGT AGG TGT AGA CAG AAG ATG CCA              903
Arg Gly Glu Asn Ala Tyr Tyr Cys Gly Arg Cys Arg Gln Lys Met Pro
220                         225                    230                235

GCT TCC AAG ACC CTG ACC CTG CAT ATT CAT AGT GCC CCA AAG GTA CTC CTG CTA      951
Ala Ser Lys Thr Leu Thr Leu His Ile His Ser Ala Pro Lys Val Leu Leu Leu
        240                         245                    250

GTG TTA AAG CGC TTC TCG GCC TTC ATG GGT AAC AAG TTG GAC AGA AAA              999
Val Leu Lys Arg Phe Ser Ala Phe Met Gly Asn Lys Leu Asp Arg Lys
        255                         260                    265

GTA AGC TAC CCA GAG TTC CTT GAC CTG AAG CCA TAC CTG TCC CAG CCT             1047
Val Ser Tyr Pro Glu Phe Leu Asp Leu Lys Pro Tyr Leu Ser Gln Pro
        270                         275                    280
```

FIG. 14C

```
ACT GGA GGA CCT TTG CCT TAT GCC CTC TAT GCT GTC CTG GTC CAT GAA    1095
Thr Gly Gly Pro Leu Pro Tyr Ala Leu Tyr Ala Val Leu Val His Glu
285                 290                 295

GGT GCG ACT TGT CAC AGT GGA CAT TAC TTC TCT TAT GTC AAA GCC AGA    1143
Gly Ala Thr Cys His Ser Gly His Tyr Phe Ser Tyr Val Lys Ala Arg
    300                 305                 310             315

CAT GGG GCA TGG TAC TAT AAG ATG GAT GAT ACT AAG GTC ACC AGC TGC GAT    1191
His Gly Ala Trp Tyr Tyr Lys Met Asp Asp Thr Lys Val Thr Ser Cys Asp
        320                 325                 330

GTG ACT TCT GTC CTG AAT GAG AAT GCC TAT GTG CTC TTC TAT GTG CAG    1239
Val Thr Ser Val Leu Asn Glu Asn Ala Tyr Val Leu Phe Tyr Val Gln
            335                 340                 345

CAG ACT GAC CTC AAA CTC AAA CAG GTC AGT ATT GAC ATG CCA GAG GGC AGA GTA    1287
Gln Thr Asp Leu Lys Leu Lys Gln Val Ser Ile Asp Met Pro Glu Gly Arg Val
                350                 355                 360

CAT GAG GTT CTC GAC CCT GAA TAC CAG CTG AAG CTG AAA AAA TCC CGG AGA AAA    1335
His Glu Val Leu Asp Pro Glu Tyr Gln Leu Lys Leu Lys Ser Arg Arg Lys
            365                 370                 375

AAG CAT AAG AAA AGC CCT TGC ACA GAA GAT GCG GGA GAG CCC TGC    1383
Lys His Lys Lys Ser Pro Cys Thr Glu Asp Ala Gly Glu Pro Cys
380                 385                 390                 395
```

FIG. 14D

```
AAA AAC AGG GAG AAG AGA GCA ACC AAA GAA ACC TCC TTA GGG GAG GGG    1431
Lys Asn Arg Glu Lys Arg Ala Thr Lys Glu Thr Ser Leu Gly Glu Gly
            400                 405                 410

AAA GTG CNT CAG GAA AAG AAC CAC AAG AAA GCT GGG CAG AAA CAT GAG    1479
Lys Val Xaa Gln Glu Lys Asn His Lys Lys Ala Gly Gln Lys His Glu
        415                 420                 425

AAT ACC AAA CTT GTG CCT CAG GAA AAC CAC CAG AAC CAC CAG AAA CTT GGG CAG    1527
Asn Thr Lys Leu Val Pro Gln Glu Asn His Gln Asn His Gln Lys Leu Gly Gln
            430                 435                 440

AAA CAC AGG ATC AAT GAA ATC TTG CCT CAG GAA CAG GAA CAG AAA CAC CAG AAA    1575
Lys His Arg Ile Asn Glu Ile Leu Pro Gln Glu Gln Glu Gln Lys His Gln Lys
        445                 450                 455

GCT GGG CAG AGC CTC AGG AAC ACG GAA GGT GAA CTT GAT CTG CCT GCT    1623
Ala Gly Gln Ser Leu Arg Asn Thr Glu Gly Glu Leu Asp Leu Pro Ala
    460                 465                 470              475

GAT GCA ATT GTG ATT GTG ATC CAC CTG CTC AGA TCC ACA GAA AAC TGG GGC AGG    1671
Asp Ala Ile Val Ile His Leu Leu Arg Ser Thr Glu Asn Trp Gly Arg
            480                 485                 490

GAT GCT CCA GAC AAG GAG AAT CAA CCC TGG CAC AAT GCT GAC AGG CTC    1719
Asp Ala Pro Asp Lys Glu Asn Gln Pro Trp His Asn Ala Asp Arg Leu
        495                 500                 505

CTC ACC TCT CAG GAC CCT GTG AAC ACT GGG CAG CTC TGT AGA CAG GAA    1767
Leu Thr Ser Gln Asp Pro Val Asn Thr Gly Gln Leu Cys Arg Gln Glu
    510                 515                 520
```

FIG. 14E

```
GGA AGA CGA AGA TCA AAG AAG GGG AAG AAC AAG CAA GGG CAG          1815
Gly Arg Arg Arg Ser Lys Lys Gly Lys Asn Lys Gln Gly Gln
        525                 530                 535

AGG CTT CTG CTT GTT TGC TAGTGTTCAC TCACCCACTC ACACAGGCTC         1863
Arg Leu Leu Leu Val Cys
        540         545

CTGTGGACAC                                                       1873
```

FIG. 14F

```
                                                                                                    DUB-1
  1 MVVALSFPEADPALSSPDAPELHQDEAQVVEELTVNGKHSLSWESPQGPGCGLQNTGNSCYLNAALQCLTHTPPLADYMLSQEHSQTCCS
    |||||||||||:||||||||:||||||||||||:||||||:||||||||||||||||||||||||||||||||||||||||||::|||||   DUB-2
  1 MVVSLSFPEQDPALSSPGAQQLHQDEAQVVVELTANDKPSLSWECPQGPGCGLQNTGNSCYLNAALQCLTHTPPLADYMLSQEYSQTCCS

91 PEGCKLCAMEALVTQSLLHSHSGDVMKPSHILTSAFHKHQQEDAHEFLMFTLETMHESCLQVHRQSKPTSEDSSPIHDIFGGWRSQIKC
    ||||:||||||:||||||||||||||||:|||||||||||||||||||||||||||||||||||:||||||||||||||||::||||
 91 PEGCKMCAMEAHVTQSLLHSHSGDVMKPSQILTSAFHKHQQEDAHEFLMFTLETMHESCLQVHRQSEPTSEDSSPIHDIFGGLWRSQIKC

181 LLCQGTSDTYDRFLDIPLDISSAQSVKQALWDTEKSEELCGDNAYYCGKCRQKMPASKTLHVHIAPKVLMVVLNRFSAFTGNKLDRKVSY
    ||||||||||||||||:|||:||||||:||||||||||| ||||||||:||||||||||||||:||||:|||:|||:|||||||||||||
181 LHCQGTSDTYDRFLDVPLDISSAQSVNQALWDTEKSEELRGENAYYCGRCRQKMPASKTLHIHSAPKVLLLVLKRFSAFMGNKLDRKVSY

271 PEFLDLKPYLSEPTGGPLPYALYAVLVHDGATSHSGHYFCCVKAGHGKWYKMDDTKVTRCDVTSVLNENAYVLFYVQQANLKQVSIDMPE
    ||||||||||||:||||||||||||||||:|||||||||||||||||||||||||||:|||||||||||||||||||:|||||||||||
271 PEFLDLKPYLSQPTGGPLPYALYAVLVHEGATCHSGHYFSYVKARHGAWYKMDDTKVTSCDVTSVLNENAYVLFYVQQTDLKQVSIDMPE

361 GRINEVLDPEYQLKKSRRKKHKKKSPFTEDLGEPCENRDKRAIKETSLGKGKVLQEVNHKKAGQKHGNTKL............
    ||::|||||||||||||||:|||||:|||:|||:|||:|::||||||||||||::|:::||||:
361 GRVHEVLDPEYQLKKSRRKKHKKKSPCTEDAGEPCKNREKRATKETSLGEGKVXQEKNHKKAGQKHENTKLVPQEQNHQKLGQKHRINEI

432 MPQKQNHQKAGQNLRNTEVELDLPADAIVIHQPRSTANWGRDSPDKENQPLHNADRLLTSQGPVNTWQLCRQEGRRRSKKGQNKNKQGQR
    :|||:||||||||||||||:||:||||||||||||:|||||||||||||||||||||||||||||||||||||||||||||||||||||
451 LPQEQNHQKAGQSLRNTEGELDLPADAIVIHLLRSTENWGRDAPDKENQPWHNADRLLTSQDPVNTGQLCRQEGRRRSKKGKNKNKQGQR

522 LLLVC.
    |||||
541 LLLVC.
```

DEUBIQUITINATING ENZYMES THAT REGULATE CELL GROWTH

RELATED APPLICATIONS

This application is a continuation of International Application No. PCT/US96/12884, which designated the United States, filed on Aug. 7, 1996, which claims the benefit of U.S. Provisional Application Serial No. 60/002,066, filed Aug. 9, 1995 and U.S. Provisional Application Serial No. 60/019,787, filed Jun. 14, 1996, the teachings of all of which are incorporated herein in their entirety.

GOVERNMENT SUPPORT

Work described herein was funded in part by the National Institutes of Health (Award RO1 DK43889-01). The United States Government has rights in the invention.

BACKGROUND OF THE INVENTION

Recently, a large superfamily of genes encoding deubiquitinating enzymes, called ubps, has been identified. Ubps are ubiquitin-specific thiol proteases. Deubiquitinating enzymes have multiple roles within the cell, including stabilization of some ubiquitin (Ub) conjugated substrates, degradation of other Ub-conjugated substrates and recycling of the cell's free monomeric Ub pool. Some deubiquitinating enzymes remove Ub from cellular target proteins and thereby prevent proteasome mediated degradation (UBP2). Other deubiquitinating enzymes remove Ub from Ub-peptide degradation products produced by the proteasomes and thereby accelerate proteasome mediated degradation (Doa-4). Little is known about the specific cellular functions of the ubp family members. The presence of multiple family members suggests considerable functional diversity. Disruption of ubp genes, in general, has not resulted in phenotypic variation, suggesting considerable functional redundancy among members of the superfamily.

Protein ubiquitination also serves regulatory functions that do not involve protein degradation (Hochstrasser al., Cell 84:813–815 (1995)). For example, Hicke and Riezman (Hicke and Riezman, Cell 84:277–287 (1996)) have recently demonstrated ligand inducible ubiquitination of the Ste2 receptor in yeast. Ubiquitination of the Ste2 receptor results in receptor endocytosis and receptor targeting to vacuoles, not proteosomes. Chen, et at. (Chen al., Cell 84:853–862 (1996)) have demonstrated that activation of the IKBa Kinase requires a rapid, inducible ubiquitination event. This ubiquitination event is a prerequisite for the specific phosphorylation of IKBa and does not result in subsequent proteolysis of the complex. Whether or not the ubiquitination of Ste2 or IKBa Kinase is reversible through the action of a specific deubiquitinating enzyme is not known.

SUMMARY OF THE INVENTION

The present invention relates to ubiquitin-specific thiol proteases or deubiquitinating enzymes, referred to as DUB (DeUBiquitinating) enzymes, of eukaryotic origin which are members of a superfamily of deubiquitinating enzymes and which comprise a new subfamily of deubiquitinating enzymes which are similar in size and amino acid sequence to one another. DUB enzymes of the present invention are of eukaryotic origin, such as vertebrate origin, including mammalian (e.g., murine, human) origin, as well as yeast origin. All DUB enzymes of the present invention are inducible by at least one cytokine. Further, DUB enzymes of the present invention are of three types: (a) interleukin-3 (IL-3), interleukin-5 (IL-5) and/or granulocyte macrophage colony stimulating factor (GM-CSF)-inducible DUB enzymes; (b) interleukin-2 (IL-2)-inducible DUB enzymes, both (a) and (b) being specifically expressed in hematopoietic cells; and (c) those DUB enzymes induced by at least one cytokine, also referred to as other cytokineinducible DUB enzymes. It was originally thought that the IL-3, IL-5 and GM-CSF-inducible DUB enzymes, described above, were inducible only with IL-3. However, as described herein, this type of DUB enzyme is also inducible with IL-3, IL-5 and/or GM-CSF. The IL-3, IL-5 and GM-CSF receptors share a β common (βc) subunit, which appears to be responsible for induction of this type of DUB enzyme.

As described herein, DUB enzymes of the present invention are encoded by nucleic acid sequences which cross hybridize. Therefore, additional DUB enzymes can be identified through the use of DNAs or RNAs described herein and known hybridization methods. DUB enzymes encoded by DNAs which hybridize, under low stringency, with nucleic acids described herein (e.g., cDNAs, genomic DNAs such as DUB-1, DUB-2, DUB-3, DUB-4, DUB-5, human DUB D38378 and fragments thereof) and which can be confirmed by further analysis, are within the scope of the present invention. It should be noted at this time that DUB-2 of the present application was referred to as (is the same as) DUB-3 of the provisional application U.S. Ser. No. 60/002066 and DUB-3 of the present application was referred to as (is the same as) DUB-2 of the provisional application U.S. Serial No. 60/002066.

DUB enzymes of the present invention include the two conserved domains (one containing an active cysteine residue (CYS domain) and one containing conserved histidine residues (HIS domain)) present in superfamily members. In addition, they include variable regions (e.g., a hypervariable region, a basic region) within the carboxy terminal regions. The DUB enzymes described herein are smaller than previously-described ubiquitin-specific thiol proteases of the ubp superfamily. DUB enzymes of the present invention generally comprise 400–700 amino acid residues, and typically comprise 475–625 amino acid residues and even more typically average 500 to 550 amino acid residues. DUB enzymes of the present invention show substantial identity to one another not only in the conserved regions (i.e., the CYS domain and HIS domain), but throughout their entire amino acid sequences. The DUB enzymes of the present invention generally exhibit at least 30% homology to one another throughout the primary amino acid sequence and, typically, at least 50% identity, and more typically at least 65% identity, and most typically at least 80% identity. The present invention also relates to DUB enzyme variants (also referred to as DUB enzyme mutant polypeptides) and fusion proteins containing a DUB enzyme or DUB enzyme variant.

The present invention further encompasses nucleic acids, including DNA encoding DUB enzymes and DUB enzyme variants and RNA transcribed from or encoded by DNA encoding DUB enzymes or DUB enzyme variants; nucleic acid constructs comprising DNA or RNA encoding a DUB enzyme of the present invention; promoters and enhancers present in DUB genes; and host cells containing the nucleic acid constructs. It further relates to methods of producing heterologous proteins through the use of such promoters and/or enhancers.

The present invention also relates to antibodies (monoclonal and polyclonal) which bind a DUB enzyme or DUB enzyme variant; methods of producing DUB enzymes and DUB enzyme variants and uses thereof, including methods of altering (reducing or inhibiting, enhancing) cell proliferation and diagnostic methods, such as for diagnosing leukemias; methods of identifying inhibitors or enhancers of DUB enzymes; and inhibitors and enhancers of DUB enzymes.

In one embodiment, a DUB enzyme is a ubiquitin-specific thiol protease which is specifically expressed in hematopoietic cells induced with IL-3, IL-5 and/or GM-CSF. IL-3, IL-5 and/or GM-CSF-inducible DUB enzymes specifically expressed in hematopoietic cells include DUB-1 (SEQ ID NO. 2) and other DUB enzymes which are IL-3, IL-5 and/or GM-CSF inducible and have ubiquitin-specific thiol protease activity. Additional IL-3, IL-5 and/or GM-CSF inducible DUB enzymes are encoded by nucleic acids (DNA or RNA) which hybridize under conditions of low stringency with DUB-1-encoding DNA or RNA or a fragment thereof, which can be further confirmed by additional analysis known to those of skill in the art, and/or have amino acid sequences sufficiently similar, as described herein, to that of the DUB-1 enzyme amino acid sequence presented herein that they are IL-3, IL-5 and/or GM-CSF inducible ubiquitin-specific thiol proteases.

In a second embodiment, a DUB enzyme is a ubiquitin-specific thiol protease which is specifically expressed in hematopoietic cells induced with IL-2. IL-2 inducible DUB enzymes specifically expressed in hematopoietic cells include DUB-2 (SEQ. ID NO. 38) and other DUB enzymes which are IL-2 inducible and have ubiquitin-specific thiol protease activity. Additional IL-2 inducible DUB enzymes are encoded by nucleic acids (DNA or RNA) which hybridize under conditions of low stringency to DUB-2-encoding DNA or RNA or a fragment thereof and/or have amino acid sequences sufficiently similar, as described herein, to that of the DUB-2 enzyme amino acid sequence presented herein that they are IL-2 inducible ubiquitin-specific thiol proteases.

Further embodiments of the present invention relate to DNA (cDNA, genomic DNA) of vertebrate origin which encodes DUB enzymes which are specifically expressed in hematopoietic cells and are referred to as (a) IL-3, IL-5 and/or GM-CSF-inducible or (b) IL-2-inducible (i.e., DNA which encodes (a) IL-3, IL-5 and/or GM-CSF or (b) IL-2-inducible DUB enzymes of the present invention); specific IL-3, IL-5 and/or GM-CSF-inducible or IL-2-inducible mRNA from hematopoietic cells; nucleic acid constructs comprising DNA or RNA encoding an IL-3, IL-5 and/or GMCSF-inducible or IL-2-inducible DUB enzyme; host cells containing the nucleic acid constructs; IL-3, IL-5 and/or GM-CSF-inducible or IL-2-inducible promoters; IL-3, IL-5 and/or GM-CSF specific or IL-2 specific enhancers and their use in producing heterologous proteins. The invention also relates to antibodies which bind the IL-3, IL-5 and/or GM-CSF-inducible or IL-2-inducible DUB enzymes, methods of producing the IL-3, IL-5 and/or GM-CSF-inducible or IL-2- inducible DUB enzymes of the present invention; methods of altering (reducing or inducing) cell proliferation; methods of diagnosing the presence or predicting the likelihood of onset of hematopoietic-based cancers, such as leukemias; methods of affecting an immune response; and methods of identifying inhibitors or enhancers of ubiquitin-specific thiol proteases.

In a third embodiment of the present invention, a DUB enzyme is a ubiquitin-specific thiol protease which is inducible by at least one cytokine (other cytokine-inducible DUB enzyme). The specific cytokines that induce these DUB enzymes can be identified by techniques known to those of skill in the art. Such DUB enzymes include DUB-3, DUB-4 and DUB-5, described herein (SEQ ID NOS. 9 and 42), additional other cytokine-inducible DUB enzymes encoded by nucleic acids (DNA or RNA) which hybridize under conditions of low stringency to DNA or RNA encoding DUB-3, DUB-4 or DUB-5 or a fragment thereof and/or have amino acid sequences sufficiently similar, as described herein, to that of DUB-3, DUB-4 or DUB-5 that they are other cytokine-inducible ubiquitin-specific thiol proteases. The inducibility of such DUB enzymes by a specific growth factor or specific growth factors can be assessed using methods described herein and known to those of skill in the art.

Additional embodiments of the present invention relate to DNAs of vertebrate origin which encode DUB enzymes, such as DUB-3, DUB-4 and DUB-5 (SEQ ID NOS. 21, 29 and 30), which are other cytokine-inducible DUB enzymes; RNAs transcribed from such DNAs; nucleic acid (DNA, RNA) constructs which comprise DNA or RNA encoding an other cytokine-inducible DUB enzyme; host cells containing such constructs; promoters and enhancers from the other cytokine-inducible DUB genes and their use in producing heterologous proteins. The invention also relates to antibodies which bind the DUB enzymes which are other cytokine-inducible; uses for the DNAs, RNAs, enzymes and antibodies; methods of producing such other cytokine-inducible DUB enzymes; methods of diagnosing the presence or predicting the likelihood of the onset of conditions or disease states associated with or caused by expression or alteration of expression or activity of an other cytokine-inducible DUB enzyme in cells and methods of identifying inhibitors or enhancers of other cytokine-inducible DUB enzymes. Such other cytokine-inducible DUB enzymes may be induced by growth factors in other (e.g., non-hematopoietic) cell types; this can be assessed using known methods.

A particular embodiment of a DUB enzyme of the present invention is a human DUB enzyme (SEQ ID NO. 24). This human DUB enzyme demonstrates that there is a DUB enzyme subfamily, as defined herein, within the deubiquitinating superfamily comprising the characteristics of: (a) conserved His and Cys domains; (b) deubiquitinating activity; (c) variable regions (hypervariable and basic); (d) similarity in size; (e) similarity in sequence; (f) cytokine inducibility. Search of Genbank DNA sequences showed that a recent submission of random human chromosomal DNA (accession number D38378), derived from human chromosome 4p, translated into a 529 amino acid polypeptide with considerable homology to murine DUB-1. This human polypeptide has 45% amino acid identity to murine DUB-1 (FIG. 11) and, based on this sequence similarity, is a member of the DUB subfamily, described herein. As predicted herein for DUB subfamily members, this human DUB shares amino acid identity with murine DUB-1 not only in the CYS and HIS domains, but also throughout the ORF. The highest level of homology is in the CYS and HIS domains. Additionally, this human DUB contains a basic region (amino acids 400–410 of D38378) and a hypervariable region (amino acids 413–442 of D38378). The DUB enzyme encoded by sequence D38378 is unlikely to be the human homologue of the murine DUB-1 itself, since human and murine homologues tend to have greater than 70% amino acid identity. Comparison of the amino acid sequence encoded by accession D38378 with other DUB enzymes can be carried out, as described herein, to assess their similarities. In addition, ubiquitin-specific thiol protease activity of the D38378-encoded protein can be assessed as described herein.

As a result of the work described herein, methods of altering cell proliferation and agents useful in the methods are available. Cell proliferation, such as hematopoietic cell proliferation, has been arrested, as described herein. Alternatively, cell proliferation can be promoted by inhibiting expression of DUB in cells. A method of arresting cell proliferation is useful in treating or preventing any condition, such as cancers (e.g., hematopoietic cell based cancers, such as leukemias and lymphomas), in which cell proliferation causes adverse physiologic effects. A method of promoting cell proliferation is useful in those contexts in which cell production is desired, such as in producing blood cells for use in replacing cells in an individual in need of blood cell replacement because of a disease or condition (e.g., immune suppression resulting from AIDS) or therapy (e.g., chemotherapy, dialysis). In addition, since it is known that IL-2 activates T-cells and thereby plays a role in inflammation and T-cell immunity, blocking of DUB-2 may be useful as a method of interfering with IL-2 function (i.e. an anti-inflammatory or immunosuppressive action).

BRIEF DESCRIPTION OF THE DRAWINGS

FIGS. 1A–1E are a representation of the nucleotide sequence (SEQ ID NO. 1) and predicted amino acid sequence (SEQ ID NO. 2) of DUB-1, in which the full-length 2674 bp DUB cDNA is shown, sequences which are copies of a conserved motif shown by Shaw and Kamen, *Cell* 46:649–667 (1986) to confer message instability are underlined and a consensus polyadenylation signal is doubly underlined.

FIG. 2 is a schematic representation of the sequence homologies among the amino acid fragments 563–580 of yeast DOA-4 (SEQ ID NO. 3), the amino acid fragment 216–233 of human Tre-2 (SEQ ID NO. 4)), the amino acid fragment 135–152 of Unp (SEQ ID NO. 35), and the amino acid fragment 52–69 of murine DUB (SEQ ID NO. 5); and among the amino acid fragment 864–920 for yeast DOA-4 (SEQ ID NO. 31), the amino acid fragment 995–1049 of human Tre-2 (SEQ ID NO. 32), the amino acid fragment 696–751 of Unp (SEQ ID NO. 36), the amino acid fragment 290–345 of murine DUB (SEQ ID NO. 33); and the alignment of the amino acid fragment 394–421 of murine DUB (SEQ ID NO. 34) with human c-myc (SEQ ID NO. 6).

FIGS. 4A and 4B are a representation of the nucleotide sequence of the DUB-1 promoter (SEQ ID NO. 7). The TATA box and a candidate STAT-binding element are underlined.

FIG. 8 is a representation of the amino acid sequence of exon 2 of DUB-1 (clone T14; SEQ ID NO. 8) and exon 2 of DUB-3 (clone 9-2; SEQ ID NO. 9), aligned to show identities and differences between the two sequences. The proteins are 81% homologous throughout the primary amino acid sequence, as evident from the consensus sequence (SEQ ID NO. 10); the greatest difference is in the "hypervariable" region which extends from amino acid 383 to amino acid 413 in DUB-1 and from amino acid 370 to amino acid 400 in DUB-3.

FIG. 9 is a schematic representation illustrating the amino acid sequence alignment of members of the DUB subfamily of deubiquitinating enzymes, produced by aligning the amino acid sequences corresponding to the CYS domain (SEQ ID NOS. 11–14 ), the HIS domain (SEQ ID NOS. 15–16) and the carboxy terminus (SEQ ID NOS. 17–20) of three DUB subfamily members represented in FIG. 7.

FIGS. 10A–10C are a representation of the nucleic acid sequence of exon 2 of DUB-3 DNA (SEQ ID NO. 21) and the predicted DUB-3 amino acid sequence (SEQ ID NO. 9).

FIG. 11 is a representation of the amino acid sequence of exon 2 of DUB-1 (SEQ ID NO. 22) and the amino acid sequence encoded by GenBank accession number D38378 (SEQ ID NO. 24), aligned to show similarities and differences between the two sequences, which are 45% identical, as evident from the consensus sequence (SEQ ID NO. 23).

FIG. 12 is the partial nucleotide sequence (SEQ ID NO. 29) of DUB-4, derived from the open reading frame of DUB-4, corresponding to amino acids 481 to 525 of the predicted amino acid sequence, which has 84.9% homology to DUB-1.

FIG. 13 is the partial nucleotide sequence (SEQ ID NO. 30) of DUB-5, derived from the open reading frame of DUB-5 corresponding to amino acids 447 to 522 of the predicted amino acid sequence, which has 85.2% homology to DUB-1.

FIGS. 14A–14F are a representation of the nucleotide sequence (SEQ. ID NO. 37) and predicted amino acid sequence (SEQ. ID NO. 38) of DUB-2.

FIG. 17 is a representation of the amino acid sequence of exon 2 of DUB-1 (clone T14; SEQ. ID NO. 8) and exon 2 of DUB-2 (clone 4; SEQ. ID NO. 38), aligned to show identities and differences between the two sequences. The proteins are 88% homologous throughout the primary amino acid sequence.

FIG. 18 is a representation of the partial nucleotide sequences of exon 2 of DUB-1, DUB-2, DUB-3 and DUB-4, (SEQ ID NOS. 39, 40, 41 and 42) aligned to show similarities and differences between the four partial sequences. The consensus/majority sequence is also shown (SEQ. ID NO. 43).

DETAILED DESCRIPTION OF THE INVENTION

Figure 3:
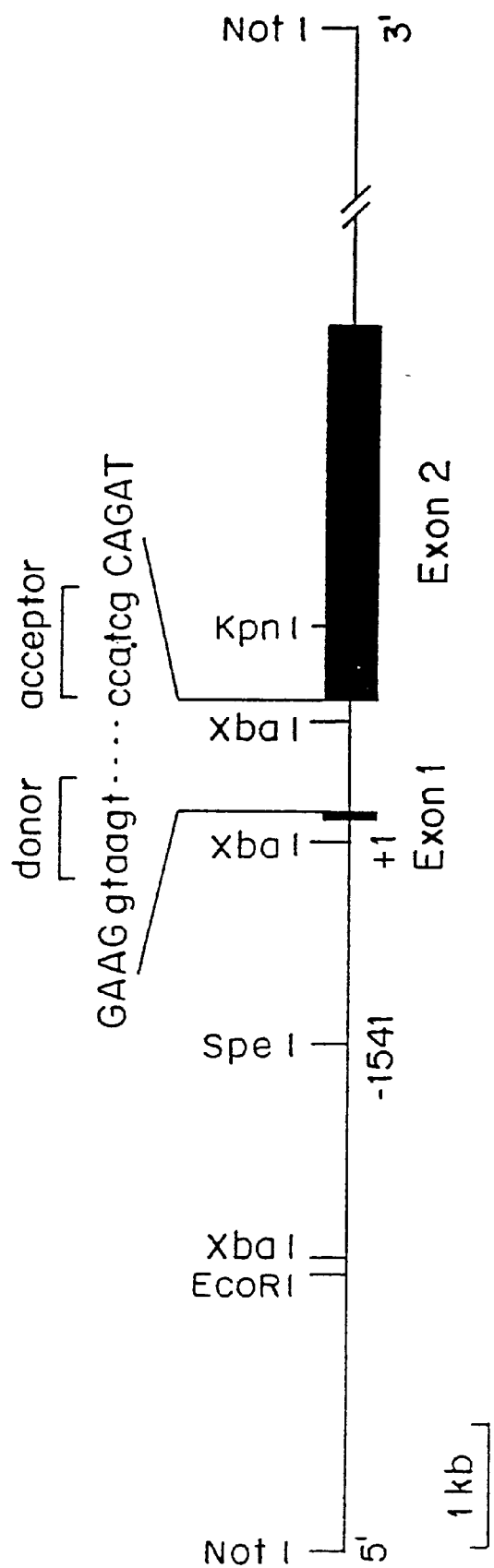
FIG. 3 is a schematic representation of the genomic organization of the DUB-1 gene, including a partial restriction map and an indication of intron-exon boundaries. The lengths and positions of the two exons are indicated. (+1) refers to the first ATG codon.
Figure 5A:
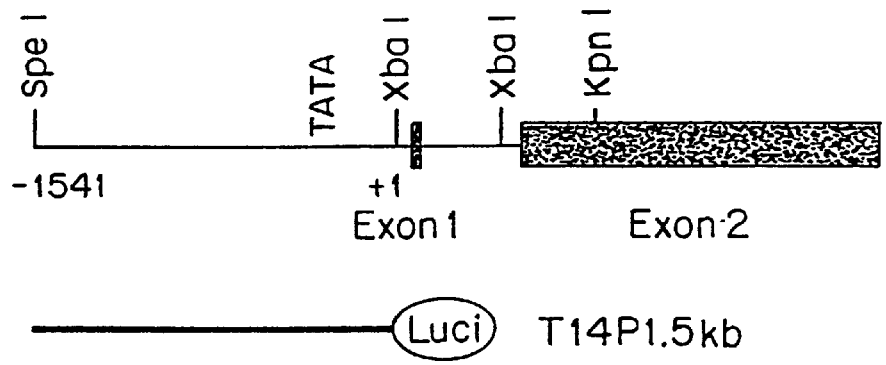
FIGS. 5A and 5B show results of assessment of activity of DUB-1 promoter by determining luciferase activity in Ba/F3-EPO-R cells transfected with pGL2Basic (mock; not shown) or PGL2BASIC containing the entire 1.5 Kb 5'-flanking region of the DUB-1 gene, depicted in FIG. 5A, and stimulated with no cytokine, EPO, or IL-3, as indicated in FIG. 5B.
Figure 5B:
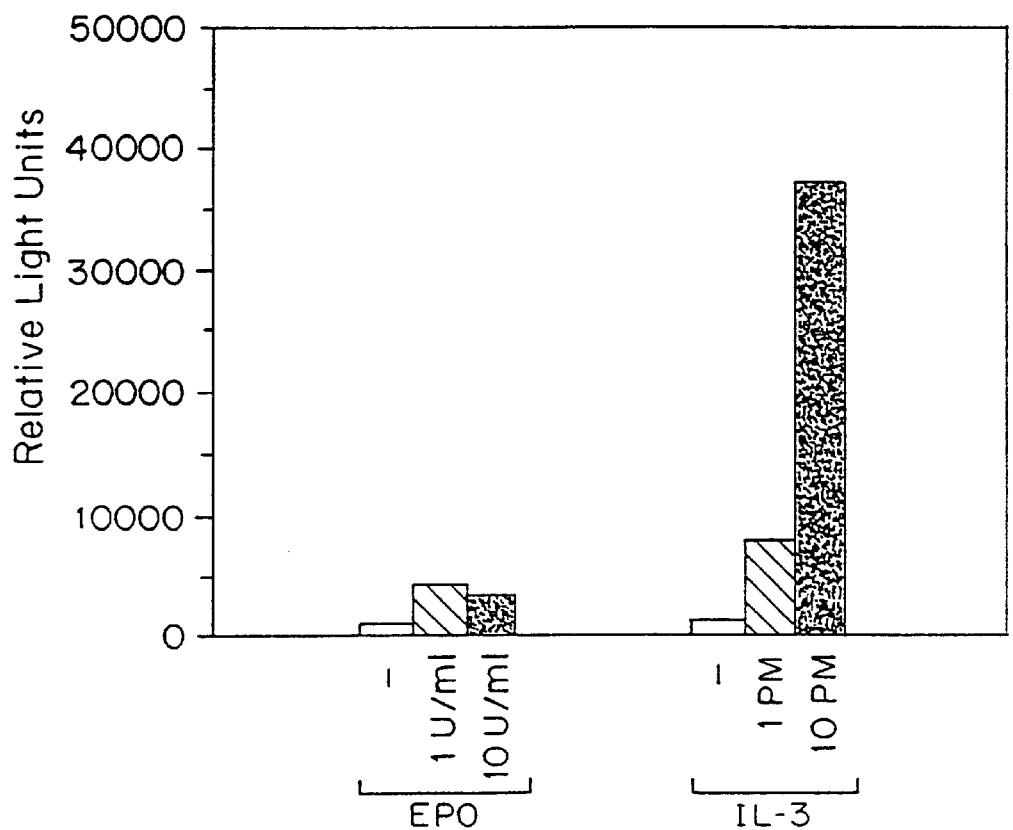
Figure 6:
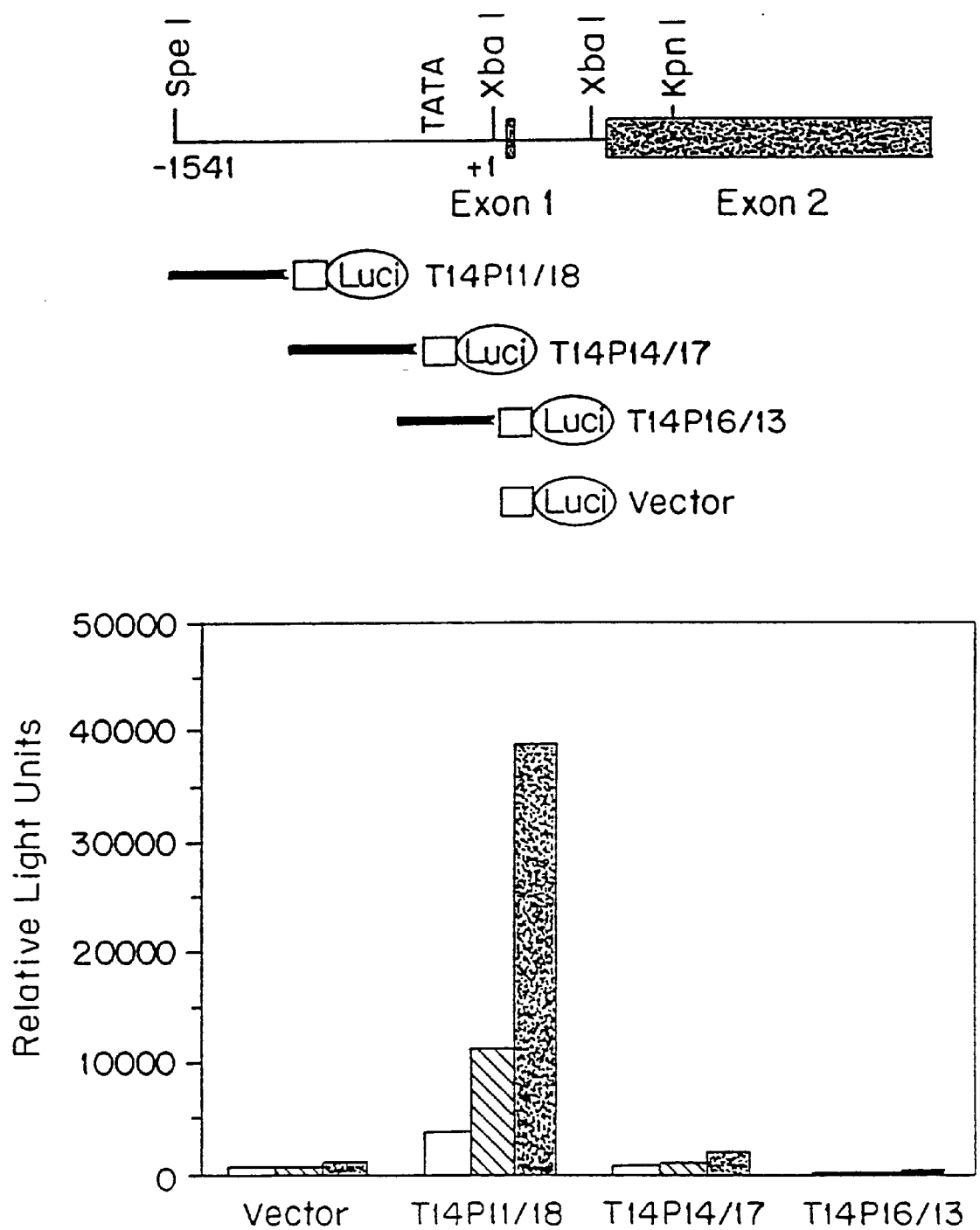
FIG. 6 shows results of assays which identified an IL-3-specific response element in the DUB-1 promoter, using three subclones to test the enhancer activity in pGL2Promoter vector. The top panel is a graphic representation of the constructs transfected into Ba/F3-EPO-R cells to assay luciferase activity. The cells were stimulated for 12 hours with 1 U/ml EPO (open bars), 1 pM IL-3 (striped bars) or 10 pM IL-3 (solid bars).
Figure 7:
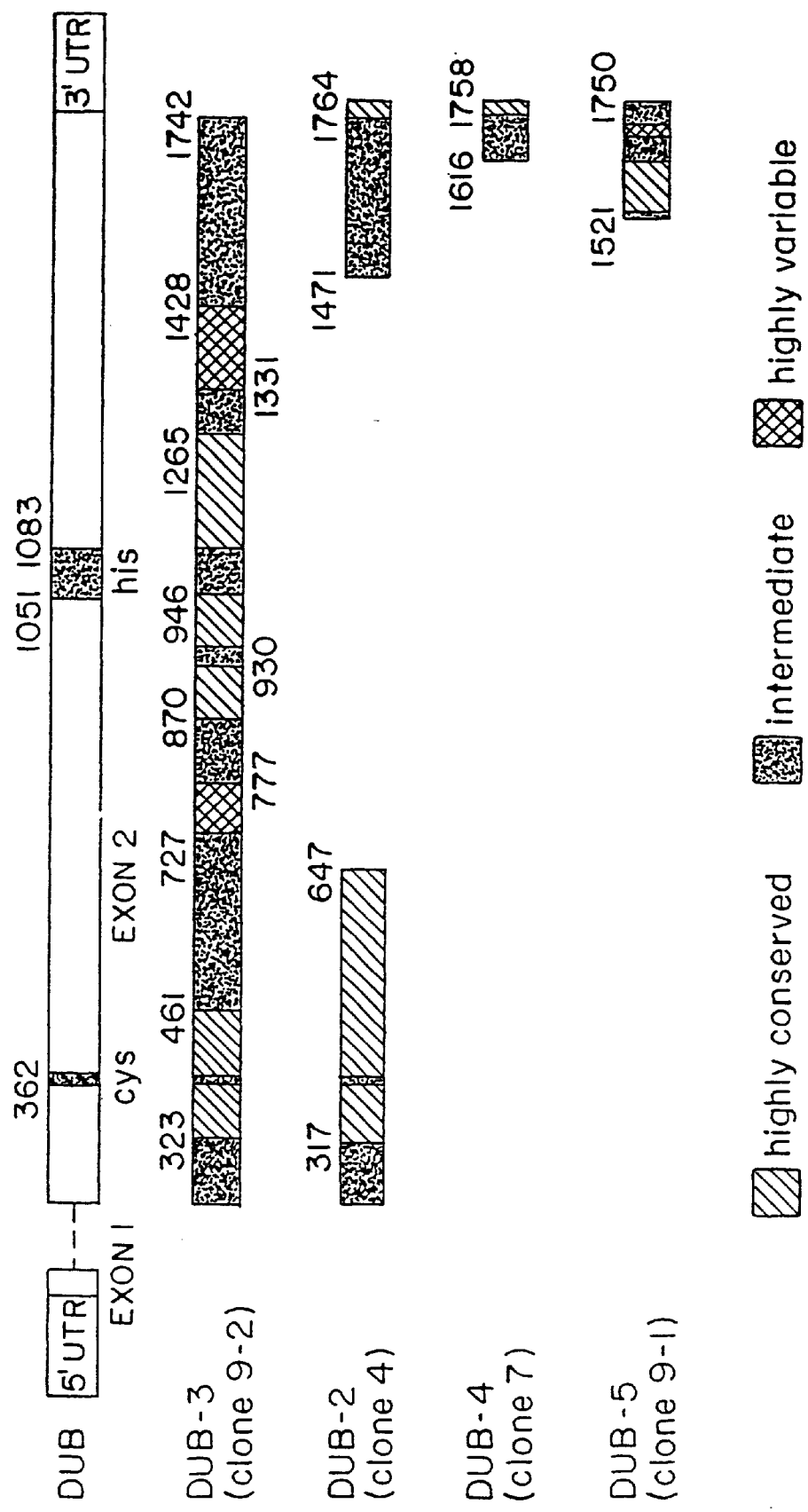
FIG. 7 is a schematic representation of genomic DNA sequences of five members of the DUB subfamily.

Described herein are the identification and characterization of ubiquitin-specific thiol proteases, referred to as deubiquitinating (DUB) enzymes, which comprise a new subfamily of a large superfamily of deubiquitinating enzymes. The DUB enzymes of the present invention, in contrast to members of other subfamilies of deubiquitinating enzymes, are relatively small proteins. They generally comprise 400–700 amino acid residues typically comprise 475–600 amino acid residues and most typically average 500–550 amino acid residues. In addition to including two domains (i.e., the CYS domain and the HIS domain) known to be conserved in other members of the superfamily, DUB enzymes of the present invention include variable regions (i.e. hypervariable and basic) within their carboxy terminal regions. DUB enzymes of the present invention include a hypervariable region and a basic region within their carboxy terminal regions (FIGS. 7–9, 11), indicating that the functional specificity (i.e., ubiquitin substrate specificity) of each DUB enzyme is determined by these carboxy terminal regions.

DUB enzymes of the present invention include DUB enzymes which are of eukaryotic origin (e.g., vertebrate origin, such as of mammalian origin including DUB enzymes from mice, dogs, cats, cows, sheep, pigs, ferrets, chimpanzees, monkeys, and humans, and of non mammalian origin, such as DUB enzymes from poultry and non vertebrate origin, such as DUB enzymes from yeast, Drosophila and C. elegans). The enzymes include (a) DUB enzymes which are specifically expressed in hematopoietic cells induced with IL-3, IL-5 and/or GM-CSF (IL-3, IL-5 and/or GM-CSF-inducible DUB enzymes), such as DUB-1 enzyme; (b) DUB enzymes which are specifically expressed in hematopoietic cells induced with IL-2 (IL-2-inducible enzymes) such as DUB-2 enzyme; and (c) DUB enzymes which are induced by at least one cytokine (other cytokine-inducible DUB enzymes), such as DUB-3, DUB-4 and DUB-5 enzymes, whose sequences are provided herein. A human DUB enzyme has been identified and its amino acid sequence is also provided.

The following is a summary of the work, described in detail in the examples which follow, which resulted in the identification, isolation and characterization of DNAs encoding DUB enzymes of the present invention and in the discovery and characterization of the novel subfamily of DUB enzymes.

As described herein, cDNAs which are inducible by either IL-3 or erythropoietin (EPO) were initially identified (See Example 1). One cDNA, designated DUB-1 or T14, was specifically expressed in hematopoietic cells in response to IL-3, but not in response to EPO, stimulation.

This 298 bp fragment was isolated and used to probe a cDNA library prepared from early hematopoietic progenitor cells inducible by IL-3 and EPO (Ba/F3-EPO-R cells). This resulted in identification of a specific IL-3-inducible mRNA, as described in Example 1. As also described in Example 1, this mRNA disappeared after the cells were depleted of IL-3 and when the cells were switched to EPO and was induced when the cells were restimulated with IL-3. Further assessment of the mRNA expression showed that it was expressed in IL-3 dependent hematopoietic progenitor cell lines, but not in cells from other tissue types. Since the DUB-1 DNA was induced as an immediate-early gene, it is likely DUB-1 plays a role in regulation of cellular growth processes (see Example 3).

In addition, the DUB-1 mRNA is also induced by IL-5 and/or GM-CSF. Induction by these growth factors was determined as described in Example 1. GM-CSF, IL-5 and IL-4 responsive cells lines were generated by transfecting Ba/F3 cells with cDNA encoding either murine GM-CSFRa, murine IL-5Ra or human IL-4R to give Ba/F3-GM-CSFRa, Ba/F3-IL-5Rα or Ba/F3-IL-4R cells respectively. Induction assays were carried out by washing the various Ba/F3 subclones described above with PBS, growing the cells at 37° C. without growth factor, and restimulating the cells with the appropriate cytokine.

Murine IL-3, but not EPO, induced DUB-1 mRNA in Ba/F3-EPO-R cells. In addition, both murine GM-CSF and murine IL-3 induced DUB-1 mRNA in Ba/F3-GM-CSFRa cells. Similarly, murine IL-5 and murine IL-3 induced DUB-1 mRNA in Ba/F3-IL-5Ra cells. Murine IL-3, but not human IL-4, induced DUB-1 mRNA in Ba/F3-IL-4R cells. Since the βc subunit of the IL-3R functionally interacts with the α chains of the IL-3R, the GM-CSFR and the IL-5R (Sato et al., *Curr. Opin. Cell Biol.* 6:174–179 (1994); Gearing et al., *EMBO J.* 8:3667–3676 (1989); Hayashida et al., *Proc. Natl. Acad. Sci. USA* 87:9655–9659 (1990); Kitamura et al., *Proc. Natl. Acad. Sci. USA* 88:5082–5086 (1991); Kitamura et al., *Cell* 66:1165–1174 (1991)) these results suggest that DUB-1 is specifically induced by the βc subunit.

Screening of the cDNA library (prepared as described above) with the 298 bp DUB-1 fragment produced three independent cDNA clones, which were isolated. All three contained approximately 2.6 kb and had full length cDNA inserts, the longest of which was 2674 bp and contained a 1581 bp open reading frame (ORF) (FIG. 1). The ORF in the three CDNA clones was identical in sequence. It also included two stop codons and 183 bp of 5' untranslated region (UTR).

The predicted open reading frame of the DUB-1/T14 cDNA encodes a polypeptide of 526 amino acids (FIG. 1), with a predicted molecular mass of 59 kD. Comparison of the predicted protein with entries in GenBank detected significant similarity with several deubiquitinating enzyme sequences, including Tre-2 (Nakamura et al., *Oncogene* 7:733–741 (1992); Onno et al., *DNA Cell. Biol.* 12:107–118 (1993)), Unp (Gupta et al., *Oncogene* 8:2307–2310 (1993)) and DOA4 (Papa and Hochstrasser, *Nature* 366:313–319 (1993)). Based on the sequence similarities, the protein, referred to herein as DUB-1 (DeUBiquitinating enzyme), is a member of the deubiquitinating enzyme superfamily, which is a group of ubiquitin-specific thiol proteases that cleave ubiquitin from modified intracellular substrates. DUB-1 is also referred to as H-DUB (Hematopoietic-specific Deubiquitinating enzyme). The sequence similarities among the enzymes were restricted to the CYS and HIS domains previously identified for this enzyme superfamily (FIG. 2) (Papa and Hochstrasser, *Nature* 366:313–319 (1993)). A critical cysteine residue in DUB (Cys60) is conserved for all family members (Papa and Hochstrasser, Nature 366:313–319 (1993)). Deubiquitinating enzymes, which are ubiquitin-specific thiol proteases, utilize this cysteine residue for enzymatic cleavage of ubiquitin from the amino terminus of a ubiquitin-conjugated protein (Hershko and Ciechanover, *Annu. Rev. Biochem.* 61:761–807 (1992)). The 3' untranslated region of the DUB-1 cDNA contained two ATTA sequences, located in the A-T rich domains. The AUUUA sequence, found in the 3' untranslated regions of many immediate-early mRNAs, is believed to play a role in DUB mRNA turnover (Shaw and Kamen, *Cell* 46:649–667 (1986)). Assessment of DUB-1 showed that it also has homology to a region of an oncoprotein (c-myc (FIG. 2)).

Members of the deubiquitinating enzyme superfamily have considerable substrate specificity. Further assessment of DUB-1, described in Example 2, showed that it is a functional deubiquitinating enzyme. When expressed as a fusion protein with glutathione-S-transferase (GST-DUB fusion protein), DUB-1 cleaved the protein Ub-Met-βgal, in which ubiquitin is fused to the N-terminus of β-galactosidase, to an extent comparable to that of Ubp1, a known yeast deubiquitinating enzyme. A mutant DUB polypeptide, containing a C60S mutation, was unable to cleave the Ub-Met-βgal substrate (Example 2). Taken together, these results demonstrate that DUB-1 has deubiquitinating activity and that Cys60 is critical for its thiol protease activity.

Increasing evidence suggests that ubiquitin-mediated proteolysis plays an important role in cellular growth and cell cycle progression (p53, cyclin, jun, iKb). As also described herein (Example 3), DUB-1 has been shown to encode a protein that regulates cell growth; DUB-1 has been shown to suppress cell cycle progression in the G1 phase. As described in Example 3, induced expression of DUB-1 arrests cell growth in the G0/G1 phase of the cell cycle. As also described in Example 3, cells expressing a DUB-1 variant in which a cysteine residue critical for thiol protease activity was mutated proliferated normally in IL-3. Results described in Example 3 demonstrate that wild type DUB-1 acts as a growth suppressor in IL-3 dependent cells.

As described in Example 4, DUB-1 mRNA levels are cell cycle regulated. That is, DUB-1 mRNA was induced following cell stimulation by IL-3, but rapidly decreased in abundance before completion of the Gi phase. DUB-1 mRNA levels rapidly declined after 8 hours.

Also described herein is the isolation, using the full length DUB-1 cDNA as a probe, of an IL-2 inducible mRNA. CTLL cells were removed from growth factor and restimulated with IL-2. An inducible 2.5 kb mRNA (DUB-2) was identified that weakly hybridized with the full length DUB-1 cDNA probe. The 2.5 kb DUB-2 mRNA was distinct from the 2.7 kb DUB-1 mRNA. DUB-2 mRNA levels were rapidly induced within 30 minutes of IL-2 restimulation but declined after 6 hours, similar to the induction kinetics observed for DUB-1 mRNA. The DUB-2 mRNA was super-induced in the presence of cycloheximide (10 μg/ml), thereby defining DUB-2 as an IL-2-specific immediate-early gene product.

The DUB-2 mRNA (2.5 kb) was expressed in the murine T-cell lines 3Do (Marrack et al., *J. Exp. Med* 158:1077–1091 (1983)) but was not expressed in other IL-3 dependent murine hematopoietic cell lines including 32D and Ba/F3. The DUB-2 mRNA was also expressed in murine primary T-cells but was not expressed in other normal murine tissues.

Also described herein is the isolation, using oligonucleotide primers derived from the DUB-1 cDNA sequence and total RNA from IL-2 stimulated CTLL cells, of a DUB-2 cDNA by RT-PCR. The cDNA fragment, bp 198, contained a full-length open reading frame (FIG. 14). Six independent cDNA clones derived from IL-2 stimulated CTLL cells were sequenced, and all were DUB-2. The DUB-2 cDNA was not isolated by RT-PCR from unstimulated CTLL cells or from IL-3 stimulated Ba/F3 cells. In addition, six independent cDNA clones derived by RT-PCR from IL-3 stimulated Ba/F3 cells were all DUB-1.

The DUB-2 cDNA encodes a polypeptide of 545 amino acids (62 kD) that has 93% amino acid similarity and 88% identity to DUB-1 (FIG. 17). The DUB-2 polypeptide contains the highly conserved Cys and His domains. These domains are most likely responsible for forming the enzyme active site. The likely active site nucleophile of DUB-2 is a cysteine residue (C60) in the Cys domain that is found in all known ubp family members. In addition, DUB-2 has a lysine rich region (amino acids 374 to 384) and a hypervariable region (amino acids 431 to 451), which contains a duplication of the eight amino acid sequence, PQEQNHQK.

Also described herein is the isolation, using the full-length DUB-1 cDNA as a probe, of five murine genomic clones, each containing a full-length DUB family member. The murine library used was a total murine DNA library. Despite this, and the fact that the full-length murine ORF was used as the probe, no members of the deubiquitinating enzyme superfamily other than members of the novel DUB subfamily described herein were isolated.

As discussed above, the DUB subfamily members are all related to each other in size and sequence. The DUB sub-family is a new subfamily of the large deubiquitinating enzyme superfamily.

Figure 18:
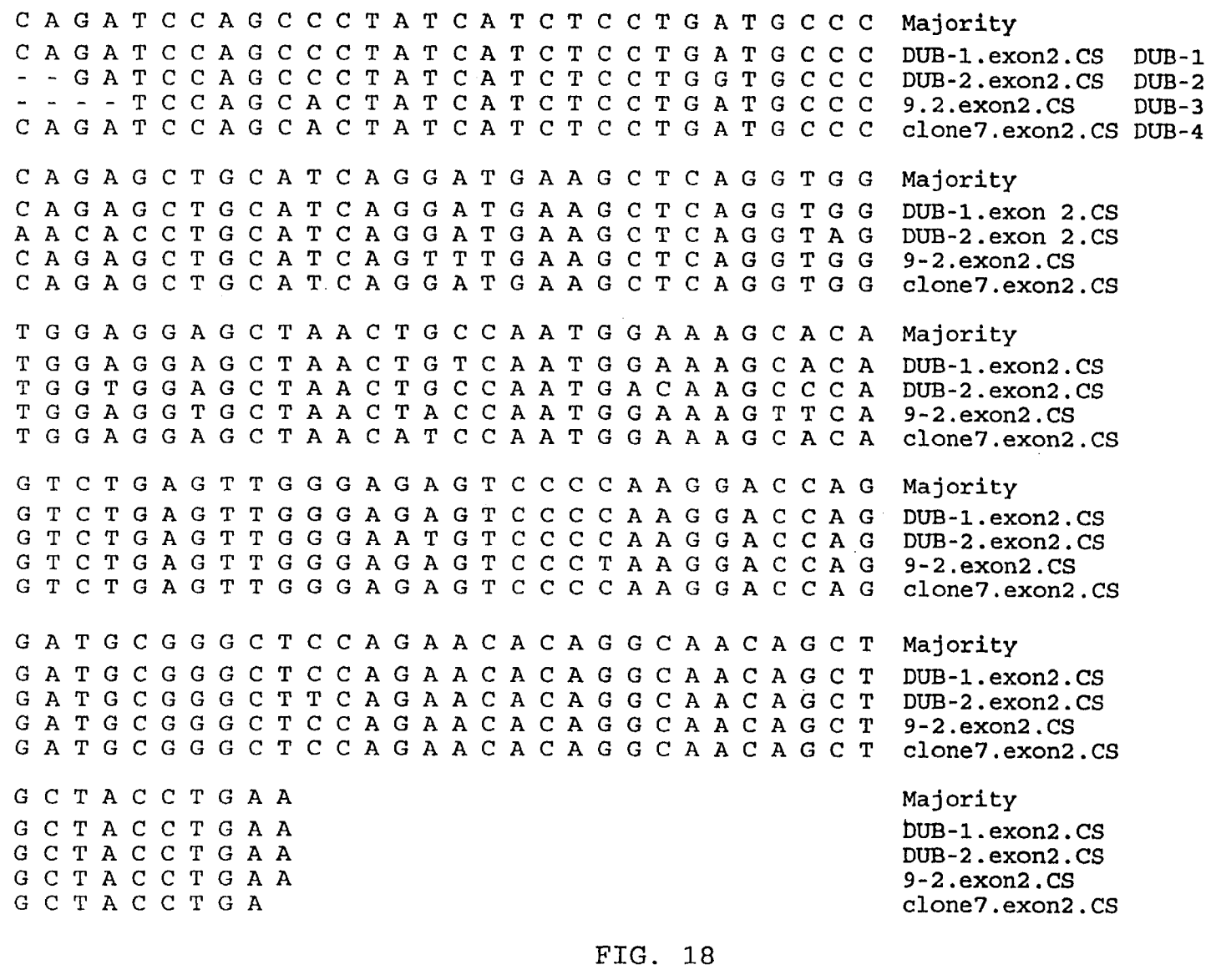

One genomic clone has an ORF identical to the ORF of the DUB-1 cDNA and, therefore, is the DUB-1 gene itself. A second clone, designated clone 4, has a nucleotide sequence which is identical within the ORF to the DUB-2 cDNA described above and, therefore, is the DUB-2 gene. A third clone, designated 9–2, has an ORF which is 81% identical to the ORF of DUB-1; the DNA is designated DUB-3. The DUB-3 enzyme, like DUB-1 and DUB-2 has deubiquitinating activity in vitro. A comparison of the DUB-1 and DUB-3 sequences is represented schematically in FIG. 7 and shows sequence homology of approximately 45% throughout the ORF. The other two clones contained DNA which contained a hypervariable region and a basic region near the carboxy terminus, as represented schematically in FIG. 7. Partial DNA sequences for DUB-4 are shown in FIGS. 12 and 18 and the partial DNA sequence for DUB-5 is shown in FIG. 13. The 143 bp sequence for DUB-4 (clone 7) is derived from the open reading frame of DUB-4 corresponding to amino acid residues 481–525. The 228 bp sequence for DUB-5 (clone 9-1) is derived from the open reading frame of DUB-5 corresponding to amino acid residues 447 to 522. The corresponding DUB-4 and DUB-5 predicted amino acid sequences are 84.9% and 85.2% homologous, respectively, to the DUB-1 amino acid sequence. All five genes contain two exons and have identical intron-exon boundaries. The predicted amino acid sequences include multiple differences, which suggests that each clone is an independent gene and not an allelic variant of the same gene. Internal STOP codons were not observed, indicating that these sequences are bona fide genes and not pseudogenes. All five genes map to a region of murine chromosome 7 and are likely to occur as a tandem repeat along the chromosome, further evidence that they are five separate genes. This region of mouse chromosome 7 corresponds to a region of human chromosome 11p15, a region known to contain a tumor suppressor gene (Koufos, M. F. et al., *Nature* 316:330–334 (1985); Koufos, M. F. et al., *Am. J. Hum. Genet.* 44:711–719 (1989)) and is a frequent site of translocations in human leukemia. (Boehm, et al., *EMBO J.* 179:901–909 (1994); LeBeau et al., *PNAS* 83:9744–9748 (1986); McGuire et al., *Mol. Cell. Biol.* 9:2124–2132 (1989)).

Alignment of the DUB-1 and DUB-2 exon 2 amino acid sequences showed that DUB-2 has 93% amino acid similarity and 88% identity to DUB-1 (FIG. 17). Alignment of the DUB-1 and DUB-3 exon 2 amino acid sequences similarly showed that the two enzymes are 81% homologous throughout the primary amino acid sequence (FIG. 8); the greatest difference is in the "hypervariable" region which extends from amino acid 383 to amino acid 413 in DUB-1 and from amino acid 370 to amino acid 400 in DUB-3. DUB-1 and DUB-3 exon 1 amino acid sequences are identical. DUB-2 also contains a small exon (exon 1) encoding amino acids 1–9 and a larger exon (exon 2) encoding amino acids 10–545 similar to the genomic organization of DUB-1 and DUB-3. Alignments of the DUB-1, DUB-2 and DUB-3 enzyme amino acid sequences for the CYS domain and the C-terminal domain and of the DUB-1 and DUB-3 amino acid sequences for the HIS domain are shown in FIG. 9, in which the extensive homology of the three sequences is evident. Alignment of the nucleotide sequences of a region of exon 2 of DUB-1, DUB-2, DUB-3 and DUB-4 is shown in FIG. 18. Alignment of the amino acid sequence of exon 2 of DUB-1 with human DUB enzyme D38378 is shown in FIG. 11. This shows that the human DUB and murine DUB-1 share amino acid identity not only in the CYS and HIS domains where the highest level of homology is evident, but also throughout the ORF. Human DUB is 529 amino acid polypeptide which contains a basic region (amino acid residues 400–410 of D38378, FIG. 11) and a hypervariable region (amino acid residues 413–442 of D38378, FIG. 11).

Characterization of the DUB-1 gene showed that it is an immediate-early gene that is specifically induced by the receptors for IL-3, IL-5 and/or GM-CSF, suggesting a requirement for the β common (βc) subunit shared by these receptors. This is the first example of an immediate-early gene that is induced by a specific subunit of a cytokine receptor. Work described herein (Example 5) also showed that DUB-1 contains a promoter which is specifically activated by IL-3, IL-5 and/or GM-CSF (i.e., an IL-3, IL-5 and/or GM-CSF responsive promoter). The 5' region of DUB-1 was shown to contain an IL-3, IL-5 and/or GM-CSF specific enhancer. This DUB-1 enhancer is the first example of an enhancer that is specifically activated by a specific subunit of a cytokine receptor. Deletional analysis identified a minimal enhancer region of 112 bp (−1528 to −1416 of 5' region, FIG. 4). This enhancer region has no known DNA binding elements, such as GAS or ISRE elements (Darnell et al., *Science* 264:1415–1421, (1994)), and the signaling pathway that activates this enhancer remains unknown. Attempts to further truncate the 112 base pair enhancer region resulted in significant loss of activity.

Further, as described herein, the membrane proximal region of βc subunit, containing amino acids 455–544, is required for induction of the DUB-1 gene. This region of βc has previously been shown to activate the JAK/STAT pathway and the c-myc induction pathway (Watanabe et al., *Mol. Biol. Cell.* 6:627–636 (1995); Watanabe et al., *Mol. Biol. Cell.* 4:983–992 (1993b)). These pathways may play a role in DUB-1 induction. In contrast, the Ras/Raf/MAP Kinase pathway is activated by the distal region of the Sc receptor. This region is therefore not required for induction of DUB-1 transcription.

Although activation of the JAK/STAT pathway by the proximal domain of βc correlates with DUB-1 induction, the JAK/STAT pathway alone cannot account for the specificity of DUB-1 induction. For instance, both IL-3 and EPO activate STAT5A and STAT5B, yet EPO does not induce DUB-1. In addition, no STAT binding elements are found in the 112 base pair enhancer region of the DUB-1 gene. Taken together, these observations suggest that additional levels of specificity must be activated by the βc subunit. For instance the βc may activate an additional unique signaling pathway, such as one recently described (Sims et al., *Mol. Cell. Biol.* 13:690–702 (1993)). Further analysis of the DUB-1 enhancer and its DNA binding proteins may reveal specific determinants of a Sc-specific signaling pathway.

Characterization of the DUB-2 gene showed that it is an IL-2 inducible immediate-early gene. The DUB-2 mRNA is expressed early in the Gi phase of the cell cycle, suggesting that DUB-2 plays a regulatory role in the initial events of the IL-2 mediated growth response.

Further assessment of DUB-2, described in Example 6, showed that it is a functional deubiquitinating enzyme. When expressed as a fusion protein with glutathione-S-transferase (GST-DUB-2 fusion protein), DUB-2 cleaved the protein Ub-Met-βgal, in which ubiquitin is fused to the N-terminus of β-galactosidase, to an extent comparable to that of DUB-1 (Example 2). A mutant DUB-2 polypeptide, containing a C60S mutation, was unable to cleave the Ub-Met-βgal substrate. Taken together, these results demonstrate that DUB-2 has deubiquitinating activity comparable to DUB-1 and that Cys6O is critical for its thiol protease activity.

Human homologues of the DUB subfamily of deubiquitinating enzymes have also been cloned. The full-length murine DUB-1 cDNA was used to screen a human genomic library under low stringency conditions. Two rounds of hybridization resulted in the isolation of eight human clones, which contain sequences consistent with DUB subfamily members. The presence of the human homologue(s) in one or more of these clones can be demonstrated using known methods; the sequences of the DNA, mRNA and encoded protein can be determined, also using known methods.

Thus, the present invention relates to a DUB enzyme subfamily, the members of which possess deubiquitinating activity and comprise two conserved domains (the CYS domain and the HIS domain) as do the members of the superfamily. Additionally, the subfamily comprises members which show substantial identity to other subfamily members throughout the primary amino acid sequences, are similar in size, have a variable region in the carboxy terminus which includes both a hypervariable and a basic region (also referred to as a lysine rich region). One DUB enzyme, designated DUB-1, is an IL-3, IL-5 and/or GM-CSF inducible enzyme which has been shown to regulate cell growth. Expression of DUB-1 in cells has been shown to arrest cell proliferation; inhibition of DUB-1 expression results in cell proliferation. Another DUB enzyme, designated DUB-2, is an IL-2 inducible enzyme.

By "substantially identical" is meant a polypeptide or nucleic acid exhibiting at least 30% sequence identity to a reference amino acid or nucleic acid sequence (e.g., the nucleic acid or predicted amino acid sequence of DUB-1). Preferably, the polypeptide or nucleic acid is at least 50% identical, more preferably at least 65% identical, and most preferably at least 80% identical to the reference molecule to which it is compared. For polypeptides, the length of comparison sequences will generally be at least 20 amino acids, more preferably at least 50 amino acids, and most preferably will include the full-length of the molecule. For nucleic acids, the length of comparison sequences will generally be at least 50 nucleotides, preferably at least 75 nucleotides, more preferably at least 100 nucleotides, and up to the full-length molecule.

Sequence identity is typically measured using sequence analysis software that is generally available (e.g., Sequence Analysis Software Package of the Genetics Computer Group, University of Wisconsin Biotechnology Center, Madison, Wis.) and is represented by calculating the percentage of identical monomeric units (nucleotides or amino acids) between the two molecules to be compared when the molecules are aligned. Such software also measures and matches similar sequences by assigning degrees of homology to various substitutions, deletions, and other modifications.

The DUB enzymes of the present invention, being IL-3, IL-5 and/or GM-CSF-inducible, IL-2-inducible and inducible by at least one cytokine, encompass enzymes from eukaryotic cells, as discussed above and substantially pure preparations thereof. Enzymes referred to herein as "isolated" are enzymes purified to a state beyond that which they naturally occur. "Isolated" enzymes include enzymes obtained by methods described herein, similar methods or other suitable methods. Portions or fragments of DUB enzymes described herein are also the subject of this invention, such as portions which comprise the hypervariable regions of DUB enzymes (e.g., approximately amino acids 383–413 of exon 2 of DUB-1 (SEQ ID NO. 27), approximately amino acids 431 to 451 of DUB-2 (SEQ ID NO. 44) and approximately amino acids 370–400 of exon 2 of DUB-3 (SEQ ID NO. 28) as represented in FIGS. 8 and 17). These portions are useful, for example, to produce antibodies (polyclonal or monoclonal) which selectively bind the DUB enzyme(s) in which the portion occurs. For example, they can be used to produce antibodies that bind DUB enzyme(s) which include the hypervariable region of DUB-1 but do not bind those which do not include this hypervariable region. Alternatively, partial amino acid sequences (DUB enzyme portions) from more than one DUB enzyme can be used to produce antibodies which bind to more than one DUB enzyme. Such peptides can be generated by methods known to those skilled in the art, including proteolytic cleavage, de novo synthesis, or by recombinant techniques.

As used herein, the term "substantially pure polypeptide" refers to a DUB polypeptide which has been separated from components which naturally accompany it. Typically, the polypeptide is substantially pure when it is at least 60%, by weight, free from the proteins and naturally-occurring organic molecules with which is normally associated in its native milieu. Preferably, the preparation is at least 75%, more preferably at least 90%, and most preferably about 99% by weight, DUB polypeptide. Substantially pure DUB polypeptide can be obtained, for example, by extraction from a natural source (e.g., hematopoietic cell); by expression of a recombinant nucleic acid encoding a DUB polypeptide; or by chemically synthesizing the protein. Purity can be measured by any standard method, e.g., by column chromatography, polyacrylamide gel electrophoresis, or by HPLC analysis.

The present invention also encompasses isolated eukaryotic DNA which encodes a ubiquitin-specific thiol protease. Specifically, it encompasses cDNA (e.g., mammalian from mice, dogs, cats, cows, sheep, pigs, ferrets, chimpanzees, monkeys, humans and other vertebrates and non-mammalian) encoding a ubiquitin-specific thiol protease or functional deubiquitinating enzyme, and active portions thereof, and isolated genomic DNA (e.g., mammalian from mice, dogs, cats, cows, sheep, pigs, ferrets, chimpanzees, monkeys, humans and other vertebrates and non-mammalian) encoding such an enzyme and active portions of the deubiquitinating enzyme (i.e., a protein or polypeptide which is less than the entire amino acid sequence encoded by the cDNA or isolated genomic DNA of the present invention and has ubiquitin-specific thiol protease activity). cDNA or genomic DNA which encodes a ubiquitin-specific thiol protease includes a) the DNA sequences represented herein (e.g., FIGS. 1, 10 and 14 (SEQ ID NOS. 1, 21 and 37); b) DNA which hybridizes, under conditions of low stringency (e.g., as described in Ausubel (*Current Protocols in Molecular Biology*, Eds. F. M. Ausubel et al., John Wiley & Sons, Inc., New York, 1994), to one of those sequences or to a sequence identified by a method in which one of the DNA sequences or fragments thereof is used as a hybridization probe and encodes a ubiquitin-specific thiol protease; and c) DNA which encodes a ubiquitin-specific thiol protease whose amino acid sequence is provided herein. Conditions of "low stringency", "moderate stringency" and "high stringency" for nucleic acid hybridizations are explained on pages 2.10.1–2.10.16 and pages 6.3.1–6.3.6 in Current Protocols in Molecular Biology, Eds. F. M. Ausubel et al., Vol. 1, John Wiley & Sons, Inc., New York, 1994, the teachings of which are hereby incorporated by reference. Factors such as probe length, base composition, percent mismatch between the hybridizing sequences, temperature and ionic strength influence the stability of nucleic acid hybrids. Thus, high, moderate or low stringency conditions can be determined empirically, depending in part upon the characteristics of the known DNA to which other unknown nucleic acids are being compared for homology.

An "isolated nucleic acid" as used herein, refers to nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. "Isolated nucleic acid" includes, for example, a recombinant DNA which is incorporated into a vector, e.g., an autonomously replicating plasmid or vector; or into the genomic DNA of a prokaryote or eukaryote, or which exists as a separate molecule (e.g., a cDNA or genomic DNA fragment produced by polymerase chain reaction or restriction endonuclease treatment) independent of other DNA sequences. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

The invention also relates to RNA transcribed from (encoded by) a cDNA or isolated genomic DNA of the present invention. Nucleic acids useful as nucleic acid probes in hybridization assays are also the subject of this invention. Both full-length nucleic acid sequences (cDNA, genomic DNA, RNA) which encode a DUB enzyme of the present invention and DNA and RNA fragments (i.e., less than an entire cDNA or genomic DNA) which do not encode a DUB enzyme are useful as nucleic acid probes. For example, as described herein, a 298 bp DUB-1 cDNA fragment (bp 1280–1578 of SEQ ID NO. 1; Example 1) and full-length cDNA (i.e., the DUB-1 ORF cDNA; Example 5) have been used to identify DUB-encoding DNA and RNA in cells. Also useful as hybridization probes are portions of the DUB-1 ORF cDNA; full-length DUB-2, DUB-3, DUB-4 and DUB-5 DNAs (cDNAs and genomic DNAs) and portions thereof, such as portions of the ORF, and additional DNAs which hybridize under low stringency conditions to DNA whose sequences are represented herein. DUB nucleic acid fragments are also useful as primers for isolating additional DUB enzyme-encoding DNAs. For example, as described in Example 1, two primers (SEQ ID NOS. 25 and 26) were used as polymerase chain reaction (PCR) primers to identify the 298 bp DUB-1 cDNA. Additional nucleic acid probes and primers can be identified from nucleic acid sequences represented herein and from nucleic acids identified through use of sequences represented herein, using known methods. Primers are typically at least 15 to 18 nucleotides in length, and probes are typically at least 30 nucleotides in length, usually between 100 and 500 nucleotides in length, and most preferably at least 500 nucleotides in length. Such nucleic acid probes and primers are encompassed by the present invention.

The invention further relates to antibodies (e.g., monoclonal and polyclonal) and antibody fragments which bind the DUB enzyme subfamily members. Antibodies can be made as described herein (e.g., Example 3) or as known to those of skill in the art. See, for example J. Sambrook et al., *Molecular Cloning: A Laboratory Manual,* Second Edition, Cold Spring Harbor Laboratory Press, Cold Spring Harbor, N.Y., 1989 and *Current Protocols in Molecular Biology,* Eds. F. M. Ausubel et al., John Wiley & Sons, Inc., New York, 1994. Polyclonal antiserum has been produced, as described in Example 3, against a fusion protein containing DUB-1 which has been shown to be useful in identifying the DUB-1 polypeptide. Similarly, polyclonal sera can be produced against other members of the DUB subfamily (e.g., DUB-2, DUB-3, DUB-4, DUB-5 polyclonal antisera) or against fragments thereof. For example, polyclonal antisera can be produced against the hypervariable region of a DUB enzyme, such as the hypervariable region of DUB-1 (FIG. 8), DUB-3 (FIG. 8) or human DUB D38378 (FIG. 11). The resulting polyclonal sera can be used to identify a particular DUB enzyme (i.e., to distinguish among DUB enzymes based on the variability of amino acid sequence shown to be present in the carboxy terminus of each DUB protein). Alternatively, known methods can be used to produce monoclonal antibodies which bind members of the DUB subfamily described herein, fragments of DUB enzymes (e.g., hypervariable regions of DUB enzymes) or additional DUB enzymes identified through methods described herein. Also included within the scope of the invention are antibody fragments and derivatives which comprise at least the functional portion of the antigen binding domain of an anti-DUB antibody molecule. Antibody fragments which contain the antigen binding domain of the molecule can be generated by known techniques. For example, such fragments include, but are not limited to: the F(ab')$_2$ fragment which can be produced by pepsin digestion of the antibody molecule; Fab' fragments which can be generated by reducing the disulfide bridges of the F(ab')$_2$ fragment; and F$_v$ fragments which can be produced by recombinant methods (e.g., see *Current Protocols in Immunology,* Coligan et al., ed., John Wiley & Sons, Inc. 1994, Unit 2.12), or as described in U.S. Pat. No. 4,642,334.

Ubiquitin-specific thiol proteases (deubiquitinating enzymes) of the present invention can be produced as fusion proteins, such as the fusion protein described herein which includes a heterologous protein, such as a glutathione-S-transferase, and a ubiquitin-specific thiol protease (e.g., DUB-1, DUB-2, DUB-3). Also the subject of the present invention are mutant or variant ubiquitin-specific thiol proteases, such as those in which an amino acid residue critical for enzymatic cleavage of ubiquitin from the amino terminus of a ubiquitin-conjugated protein is deleted or altered, rendering the enzyme nonfunctional or less active (unable to enzymatically cleave ubiquitin or able to do so but to a lesser extent than the wild type or unaltered enzyme). In one embodiment, the variant ubiquitin-specific thiol protease comprises a C60S mutation or mutation of an equivalent cysteine residue. Specifically, in one embodiment, the cysteine residue at position 60 of the DUB-1 protein is replaced by a serine residue; in another embodiment the cysteine residue at position 60 of the DUB-2 protein has been replaced by a serine residue. In an additional embodiment, DNA encoding a DUB enzyme variant of a DUB enzyme whose expression in hematopoietic cells results in arrest of growth of the hematopoietic cells in the G0/G1 phase of the cell cycle, wherein the variant lacks a conserved cysteine required for thiol protease activity and, when expressed in hematopoietic cells, does not induce arrest of growth of the hematopoietic cells in the G0/G1 phase of the cell cycle. Alternatively, other cysteine residues which are critical for the thiol protease activity of a DUB enzyme of the present invention can be mutated; amino acids other than serine can be substituted for the critical cysteine residues. These mutant or variant DUB enzymes can be used to isolate the specific protein substrates of each DUB enzyme in cells. For example, because the C60S DUB variant described herein is catalytically inactive, it should bind stably to the ubiquitin-conjugated substrate and thereby form a stable complex that can be purified and analyzed.

The invention also relates to methods of synthesizing DUB enzymes and to methods of using the claimed cDNAs, isolated genomic DNAs, enzymes and active portions thereof and antibodies and antibody fragments. In one embodiment of the present invention, a DUB enzyme of the present invention is produced in an appropriate host cell (e.g., mammalian, such as human, cells, yeast cells, bacterial cells) by introducing into the host cell a nucleic acid construct, such as a plasmid, comprising DNA or RNA encoding the DUB enzyme (heterologous nucleic acid (DNA or RNA) encoding the DUB enzyme) and appropriate regulatory elements necessary for expression of the thiol protease in the host cell. The resulting host cell contains the heterologous nucleic acid (DNA or RNA) encoding a DUB enzyme.

Expression of DUB-1 in cells results in arrest of cell growth in the G0/G1 phase of the cell cycle. Thus, the work described herein has provided a method of preventing or reducing cell proliferation. The effects of other DUB-1 enzymes on cell proliferation can be demonstrated, using the methods described herein or other methods known to those of skill in the art. Preventing or reducing proliferation of cells such as cancer cells (e.g., leukemias, solid tumors, lymphomas) provides a method of treating or preventing the cancer.

The present invention relates to a method of modifying (reducing/preventing or promoting) the proliferation of cells, particularly hematopoietic cells, by altering activity of a DUB enzyme, such as DUB-1, either directly or indirectly. Cell proliferation can be prevented or reduced by producing the DUB enzyme in cells, as described above. In addition, cell proliferation can be prevented or reduced by introducing into cells an agent (e.g., a protein or peptide) which prevents degradation of the ubiquitin-specific thiol protease, thus prolonging its activity. Suppression of proliferation of hematopoietic cells is useful, for example, to suppress the immune system during organ or cell transplantation and, thus, to reduce the likelihood of rejection of the transplant. Alternatively, cell proliferation can be promoted or enhanced by inhibiting the activity of the DUB enzyme, such as DUB-1. Activity of the protease can be inhibited by introducing into cells an agent (e.g., nucleic acids, antibodies, proteins or peptides, small organic molecules) which inhibits activity of the protease, directly (e.g., by binding to or degrading the enzyme) or indirectly (e.g., by acting as a decoy on which the enzyme acts). Proliferation of hematopoietic cells can be carried out in vitro or in vivo. If it is carried out in vitro, the resulting cells (e.g., hematopoietic cells) are introduced into a recipient using known methods. In one embodiment, hematopoietic cells are obtained from an individual, using known methods. An inhibitor of the ubiquitin-specific thiol protease (e.g., antisense nucleic acids, antibodies which bind the thiol protease) is combined with the cells, under conditions appropriate for the agent to enter the cells and affect production of the DUB enzyme, such as DUB-1 enzyme (e.g., through binding of antisense nucleic acids to DNA encoding the enzyme) or inhibit its activity (e.g., through use of antibodies which bind the enzyme). As a result, activity of the ubiquitin-specific thiol protease is inhibited and cell proliferation occurs. The cells are maintained under conditions appropriate for their proliferation for sufficient time to produce the number of cells desired. The resulting cells are introduced into an individual, who can be the individual from whom the cells were originally obtained or another individual, using known methods. In one embodiment, autologous blood cells are modified as described, resulting in their proliferation, and reinfused intravenously.

The present invention further relates to antibodies which bind a DUB enzyme of the present invention, such as DUB-1 or DUB-2. The antibodies can be monoclonal or polyclonal. They can bind more than one ubiquitin-specific thiol protease of the present invention (e.g., DUB-1 and DUB-2) or bind specifically to a region unique to one of the ubiquitin-specific thiol proteases (e.g., to the hypervariable region of DUB-1 or of DUB-2 or of DUB-3), thus making it possible to distinguish among the DUB enzymes of the present invention. For example, an antibody can be produced, using known methods, which binds the hypervariable region of DUB-1, as represented in FIG. 8, but does not bind DUB-2 or DUB-3, in which the hypervariable regions are markedly different in amino acid sequence. Alternatively, an antibody which binds a region common to all or more than one ubiquitin-specific thiol proteases of the present invention can be produced.

Another embodiment of the present invention is a method of diagnosing the presence or predicting the likelihood of onset of hematopoietic-based cancers (e.g., leukemia) by assessing the level of a DUB enzyme (e.g., DUB-1) of the present invention or of nucleic acid encoding the protease in a sample (e.g., a blood, bone marrow or other tissue sample) obtained from an individual. Levels of the enzyme (e.g., DUB-1 enzyme) which are low (i.e., less than the level which occurs in an unaffected individual) indicate that the individual has a hematopoietic-based cancer. Enzyme levels can be assessed using known methods, such as a hybridization assay, in the case in which nucleic acid levels are detected, or an immunoassay, in the case in which enzyme levels are assessed. In either case, the method can be designed to detect all DUB-encoding DNA or all DUB enzyme in a sample or to detect a selected DNA (or group of DNAs) or a selected enzyme (or group of enzymes). Detecting specific DNA(s) or enzyme(s) is particularly useful if they are shown to be those responsible for or associated with a specific hematopoietic-based cancer. Diagnostic reagents (e.g., nucleic acid hybridization probes, antibodies) useful in a general method (i.e., one in which all nucleic acids encoding DUB enzymes of the present invention or all proteases of the present invention are detected) or in a method in which selected nucleic acids or selected DUB enzymes are detected are available as a result of the work described herein and can be made using art-recognized, reproducible methods.

The present invention also relates to a method of identifying modifiers (inhibitors or enhancers) of DUB enzymes of the present invention. A variety of formats can be used to identify antagonist of DUB-1 or other DUB subfamily members. In one embodiment, a DUB enzyme is combined with a ubiquitinated substrate of the DUB enzyme and an agent to be assessed for its effect on DUB enzyme activity. The combination is maintained under conditions appropriate for the DUB enzyme to act on its substrate. Decreased DUB activity (decreased cleavage of the ubiquitinated substrate) indicates that the agent is an inhibitor of the DUB enzyme activity. Increased DUB activity (increased cleavage) indicates that the agent is an enhancer of the DUB enzyme activity. In one embodiment, an in vitro assay is carried out as described in Examples 2 and 6. In these embodiments a fusion protein, containing, for example, the full length DUB-1 protein sequence, or the full length DUB-2 protein sequence cleaves a ubiquitin-conjugated substrate in vitro. The cleaved substrate can be assayed on an immunoblot. Inhibitors of this cleavage assay can be readily screened by their addition to the reaction in vitro. For example, an agent which inhibits activity of a DUB enzyme is identified by introducing into a host cell two constructs: a first DNA construct which encodes a fusion protein comprising the DUB enzyme and a second protein which is an affinity ligand (e.g., an enzyme, antigen or other molecule for which there is a binding partner) and a second DNA construct which encodes a ubiquitin conjugated substrate of the second protein, thereby producing host cells containing the two constructs.

The host cells produced are maintained under conditions appropriate for expression of the fusion protein and the ubiquitin-conjugated substrate, thereby producing host cells expressing the fusion protein and the substrate. The host cells expressing the fusion protein and the substrate with an agent to be assessed are combined (or the host cells are otherwise contacted with the agent) and the resulting combination is maintained under conditions appropriate for the DUB enzyme component of the fusion protein to act upon its substrate (e.g., by cleaving). The extent to which the DUB enzyme cleaves the substrate is assessed. If cleavage occurs to a lesser extent in the presence of the agent than in its absence, the agent is an inhibitor of the DUB enzyme. If cleavage occurs to a greater extent in the presence of the agent than in its absence, the agent is an enhancer of DUB enzyme activity. Activity of the enzyme in the absence of the agent is assessed under the same conditions as those used for assessing its activity in the presence of the agent (i.e., under control conditions) to produce a control or reference value. The control or reference value can be a previously established value or can be determined simultaneously with or after assessment in the presence of the agent.

In one embodiment, the fusion protein is a DUB enzyme-enzyme fusion protein, such as a DUB enzyme-glutathione-S-transferase fusion protein.

In a second embodiment, an intracellular assay is carried out as described in Example 3. In this embodiment, dexamethasone induced expression of DUB-1 arrests Ba/F3 cell growth in IL-3, but does not kill these cells. Antagonists of DUB-1 can be screened that, when added to the dexamethasone-induced cells, will block DUB-1 activity and thereby promote cell proliferation. One advantage of this cell-based assay is that it screens out drugs (antagonists) that are toxic to the cells.

As described herein, the DUB-1 gene contains an IL-3, IL-5 and/or GM-CSF specific enhancer and an IL-3, IL-5 and/or GM-CSF inducible promoter in its 1.5 kb 5' flanking region. The enhancer is within the sequence −1541 to +1 of FIG. 4 and the promoter is within the sequence −1541 to −965 of FIG. 4. Recently, it has been found that the 112 bp fragment, −1528 to −1416, of the 5' region of DUB-1 is the minimal region required for IL-3, IL-5 and/or GM-CSF induction of DUB-1. The promoter and/or the enhancer can be incorporated into a DNA construct which also includes DNA encoding a product (or products) to be expressed in a host cell; the DNA is present in the construct in such a location that it is operably linked to the IL-3, IL-5 and/or GM-CSF-inducible promoter (i.e., expression of the DNA is under control of the IL-3, IL-5 and/or GM-CSF-inducible promoter). The construct is introduced into an appropriate host cell, which can be a hematopoietic cell that is responsive to IL-3, IL-5 and/or GM-CSF or another cell type which has been modified to be IL-3, IL-5 and/or GM-CSF responsive. Upon exposure to IL-3, IL-5 and/or GM-CSF the promoter and/or enhancer are induced and expression of the protein encoded by the operably-linked DNA occurs. The cells in which the product is made can be introduced into an individual, to whom they provide the product (e.g., for diagnostic, preventive or therapeutic purposes). Alternatively, the product can be isolated from the cells in which they are produced and administered to an individual. Alternatively, the promoter and/or the enhancer from another DUB gene can be used in the DNA construct. In these embodiments, cells containing the construct are induced by a growth factor to which the promoter and/or enhancer are responsive.

A further embodiment of the present invention is host cells containing nucleic acid constructs which comprise DNA or RNA encoding a DUB enzyme. The host cells can be any type of cell (e.g., prokaryote, eukaryote, including mammalian and non-mammalian cells) in which the DUB enzyme can be expressed. Nucleic acid constructs can be plasmids or other vectors from which expression occurs extrachromosomally or can be plasmids or vectors which integrate into host cell chromosomal DNA. A construct which expresses a DUB enzyme extrachromosomally also comprises sequences necessary (e.g., a promoter) for expression of the protein in the host cell type used. The nucleic acid construct can also include, for example, an enhancer, DNA encoding a signal sequence and DNA encoding a selectable marker. Nucleic acid constructs are vectors that can be used to amplify and/or express nucleic acids encoding DUB enzymes or portions thereof. An expression vector is a replicable construct in which a nucleic acid sequence encoding the DUB polypeptide is operably linked to suitable control sequences capable of effecting the expression of the DUB polypeptide. The need for such control sequences will vary depending on the cell selected and the transformation method chosen. Generally, control sequences include a transcriptional promoter and/or enhancer, a sequence encoding suitable ribosomal binding sites, and sequences which control the termination of transcription and translation. Amplification vectors include an origin of replication and a gene encoding a selectable marker to facilitate recognition of transformants, but do not require expression control domains. A gene and a promoter and/or enhancer are defined as "operably linked" if the promoter and/or enhancer controls transcription of the gene. A "functional promoter" is defined as a region of DNA involved in binding RNA polymerase to initiate transcription. The nucleic acid construct is introduced into host cells using known methods, such as electroporation, transfection or transformation, infection, calcium phosphate precipitation, microprojectile bombardment and other known means by which DNA can be introduced into cells. The resulting host cells, which contain the nucleic acid construct (or at least the DUB-encoding DNA) are maintained under conditions appropriate for production of the DUB enzyme. The DUB enzyme can be isolated or removed from the host cells using known methods.

The present invention is illustrated by the following examples, which are not intended to be limiting in any way.

METHODS AND MATERIALS

The following methods and materials were used in Examples 1–7.

Methods

Cells and Cell Culture

Ba/F3 is an IL-3-dependent murine pro-B cell line (Palacios and Steinmetz, Cell 41:727–734 (1985)). Ba/F3-EPO-R cells were generated by stable transfection of Ba/F3 cells with the cDNA encoding murine EPO-R (D'Andrea et al., Cell 57:277 (1989)). Ba/F3-EPO-R cells grow in either murine IL-3 or human EPO (Carroll et al., Proc. Natl. Acad. Sci. USA 92:2869–2873 (1995); Liboi et al., Proc. Natl. Acad. Sci. USA 90:11351–11355 (1993)). Ba/F3-GMCSFRα cells were generated by stable transfection of Ba/F3 cells with the cDNA encoding the murine GMCSFRα (Park et al., Proc. Natl. Acad. Sci. USA 89:4295–4299 (1992)). Ba/F3-GMCSFRα cells grow in either murine IL-3 or murine GM-CSF. Ba/F3-IL5Rα cells were generated by stable transfection of Ba/F3 cells with the cDNA encoding the murine IL5Rα chain (Takaki et al., EMBO. J.: 2833–2838 (1991); Takaki et al., EMBO. J. 9:4367–4374 (1990); Devos et al., EMBO. J. 10:2133–2137 (1991)). Ba/F3-IL5Rα cells grow in either murine IL-3 or murine IL-5. The Ba/F3-hIL-4R cells grow in either murine IL-3 or human IL-4 (Seldin et al., Proc. Natl. Acad. Sci. 91:2140–2144 (1994)). All Ba/F3 subclones were maintained in RPMI 1640 medium supplemented with 10% fetal calf serum (FCS) and 10% conditioned medium from WEHI-3B cells as a source of murine IL-3.

CTLL-2 cells were maintained in RPMI 1640 medium supplemented with 10% (vol/vol FCS and 2 U/ml of murine recombinant IL-2 (Boehringer-Mannheim). CTLL cells are a murine T-cell line that is dependent on Interleukin-2 for growth. 3DO cells (Marrack et al., J. Exp. Med. 158:1077–1091 (1983)) were grown as previously described.

For induction assays, the various Ba/F3 subclones were washed three times in PBS, grown at 37° C. without growth factor for eight hours, then restimulated with murine IL-3 or with one of several other growth factors for one hour. Ba/F3-EPO-R cells were restimulated with human EPO (1 pM=10 mU/ml) (Genetics Institute). Ba/F3-GMCSFRα cells were restimulated with murine GM-CSF (Prepro Tech Inc.). Ba/F3-IL5Rα cells were restimulated with murine IL-5 (R and D Systems). Ba/F3-IL4R cells were restimulated with human IL-4 (Genzyme). CTLL cells were similarly starved in RPMI 1640-10% FCS for an 8 hour period and stimulated for various times with IL-2 containing medium.

Isolation of DUB-1 and DUB-2 cDNA

Total cellular RNA was isolated by the guanidinium isothiocyanate procedure (Chirgwin et al., *Biochemistry* 18:5294–5299 (1979)) and subjected to the differential display analysis (Liang and Pardee, *Science* 257:967–971 (1992); Gene Hunter).

The DUB-1 (T14) cDNA fragment was isolated using a 5' primer (5' TCTGTGCTGGG 3'; (SEQ ID NO. 25) and a 3' primer (5' TTTTTTTTTTTGT 3') (SEQ ID NO:26) and subcloned into pCRII (Invitrogen). The DUB-1 cDNA was shown by dideoxy DNA sequencing to be 298 bp in length and to contain the 5' and 3' primers. RNA samples were electrophoresed on denaturing formaldehyde gels and blotted on to Duralon-UV membranes (Stratagene). The specified cDNA inserts, purified from agarose gels (Qiagen), were radiolabeled (Feinberg and Vogelstein, *Anal. Biochem* 132:6–13 (1983)) and hybridized for 1 hour to the filters in a 68° C. oven. Hybridized filters were washed at room temperature in 0.1×SSC and 0.1% sodium dodecyl sulfate.

DUB-2 cDNA was isolated by RT-PCR, using total cellular RNA prepared from IL-2 stimulated CTLL cells. Primers were derived from the DUB-1 sequence. The 5' primer was, 5'TTTGAAGAGGTCTTTGGAGA3' (SEQ ID NO:45), which is-upstream of the ATG START codon. The 3' primer was, 5'GTGTCCACAGGAGCCTGTGT3' (SEQ ID NO:46), which is downstream of the TGA STOP codon. The PCR reaction was performed at 94° C. for one minute, 55° C. for one minute, and 72° C. for two minutes for a total of 35 cycles. The amplified cDNA was cloned into PCRII (Invitrogen) and sequenced by the dideoxynucleotide method. PCR errors were eliminated by confirming the sequence of six independent cDNA clones. The DUB-2 cDNA product was amplified by RT-PCR using mRNA derived from IL-2 stimulated CTLL cells. Six independent RT-PCR products were compared by sequence analysis and all were identical.

Northern and Souther Blot Analysis

In general for Northern blots, RNA samples (10–30 μg) were electrophoresed on denaturing formaldehyde gels and blotted onto Duralon-UV membranes (Stratagene). For Southern blots, genomic DNA (10 μg) was digested with the indicated restriction enzymes, electrophoresed on 1% agarose gel, and blotted onto Duralon-UV membranes (Stratagene). The indicated cDNA inserts, purified from agarose gels (Qiagen), were radiolabeled and hybridized for 1 hour to the membranes in a 68° C. oven. Hybridized filters were washed at room temperature in 0.1×SSC and 0.1% sodium dodecyl sulfate.

Northern blot analysis of total RNA (10 μg per lane) from Ba/F3-EPO-R cells was carried out under various growth conditions. The probe was a 298 bp cDNA fragment, cloned by differential display, from the 3' end of the DUB cDNA. RNA was prepared from cells growing in murine IL-3 or after switching cells to EPO for 8 hours, 12 hours or 24 hours. Total RNA was isolated from cells cultured under different conditions. Where indicated, cycloheximide (10 μg/ml) was added. $^{32}$P-labeled probes are also indicated. Total cellular RNAs (10 μg) and tissue RNAs (20 μg) were subjected to Northern blot analysis and probed with the DUB-1 cDNA. The blot was stripped and rehybridized with the β-actin cDNA probe.

cDNA Library Construction

A cDNA library, from Ba/F3 cells growing in IL-3, was constructed in the phage vector, lambda ZAP (Stratagene). Poly(A)+mRNA used for library construction was prepared by the Fast Track mRNA Isolation Kit (Invitrogen). The T14 cDNA (298 bp) isolated by differential display, was labeled with $^{32}$P dCTP by random prime labeling (Feinberg & Vogelstein, *Anal. Biochem* 132:6–13 (1983)) and used to screen 1×10$^6$ PFUs from the library. Three independent positive clones with variable lengths that hybridized with the T14 cDNA probe were isolated, and the corresponding plasmids were isolated from the phage clones. The cDNA from one clone was sequenced on both strands by the dideoxy DNA sequencing protocol (USB).

Assessment of Deubiquitinating Activity

Deubiquitination of ubiquitin-conjugated β-galactosidase fusion protein in transformed bacteria has been previously described (Papa and Hochstrasser, *Nature* 366:313–319, (1993)). The 1578 bp of the wild-type DUB fragment (corresponding to amino acids 1 to 526) and a cDNA containing a missense mutation (C60S) were generated by PCR and inserted, in frame, into pGEX-2TK (Pharmacia) downstream of the glutathione-S-transferase coding element. In addition, a 1638 bp fragment from the wild-type DUB-2 cDNA (corresponding to amino acids 1 to 545) and a cDNA containing a missense mutation (C60S) were generated by PCR and inserted, in frame, into pGEX-2TK (Pharmacia) downstream of the glutathione-S-transferase (GST) coding element. Ub-Met-βgal was expressed from a pACYC184-based plasmid. Plasmid-bearing *E. coli* MC1066 cells or MC1061 cells were lysed and analyzed by immunoblotting with a rabbit anti-βgal antiserum (Cappel), a rabbit anti-GST antiserum (Santa Cruz) and the ECL system (Amersham).

Assessment of Cell Cycle Regulation of DUB-1 mRNA

Ba/F3-EPO-R cells were arrested in G0 by growth factor starvation for 12 hours and were restimulated with IL-3 to enter the cell cycle synchronously. Total RNA (10 μg per lane) extracted from cells at the indicated time (in hours) was subjected to Northern blotting analysis with the indicated cDNA probes. The different cell cycle phases were determined by flow-cytometric analysis of cellular DNA content. Immunoblot Analysis of Steroid Induced DUB-1 Polypeptide Lysates (100 μg of total protein) from the indicated cells were electrophoresed in 10t SDS-polyacrylamide gels and blotted with an affinity purified anti-DUB-1 antibody (1:1000). Transfected Ba/F3 cells were cultured in IL-3 medium with or without dexamethasone (0.1 μM). Cell number was calculated by the trypan blue exclusion technique. Ba/F3 cells, transfected with wild-type DUB-1, were grown in IL-3 with or without dexamethasone for 6 days. Dexamethasone-treated cells were washed, replated in IL-3 medium (without dexamethasone) on day 7, and cultured for an additional 6 days. The indicated cell lines were grown for 48 hours (5×10$^5$ cells/ml) with or without dexamethasone (0.1 μM). The cells were stained with propidium iodide and analyzed by flow cytometry.

The open reading frame of DUB-1 (or DUB-1 (C6OS)) was generated by PCR using the following primers: 5' GCGAATTCTTTGAAGAGGGTCTTTGGAGA 3' (SEQ ID NO:47) (−19 to 1) and 5' ATCTCGAGGTGTCCACAG-GAGCCTGTGT 3' (SEQ ID NO:48) (1802 to 1781). The fragment (1637 bp) was subcloned into the Sma I/Xho I cloning sites of pMSG (Pharmacia) which contains a MMTV-LTR inducible promoter and a gpt selection marker. Parental Ba/F3 cells were electroporated with vector alone or with pMSG-DUB-1, as previously described (D'Andrea et al., *Mol. Cell. Biol.* 11:1980–1981 (1991)). After 3 days in IL-3 medium, the cells were selected in IL-3 medium containing 250 µg/ml Xanthine, 15 µg/ml hypoxanthine, 10 µg/ml thymidine, 2 µg/ml aminopterin, 25 µg/ml mycophenolic acid. Gpt-resistant subclones were isolated by limiting dilution. DUB-1 expression was induced by adding 0.1 µM dexamethasone (diluted from 10 mM stock in 70% ETOH). Immunoblots were performed as previously described (Barber and D'Andrea, *Mol. Cell. Biol.* 14:6506–6514 (1994)) using an affinity purified anti-DUB-1 antiserum and ECL technology. The DUB-1 antiserum was raised by injecting a full length GST-DUB-1 fusion protein into a New Zealand White rabbit purified by standard procedures (Yamashita et al., *Proc. Natl. Acad. Sci. USA* 91:6712–6716 (1994)). In vitro translation of the full-length DUB-1 polypeptide was performed by standard procedures (Promega). Cell growth was measured by the trypan blue exclusion technique (D'Andrea et al., *Mol. Cell. Biol.* 11:1980–1981 (1991)). Cell cycle analysis was performed by FACS, as previously described (Carroll et al., *Proc. Natl. Acad. Sci. USA* 92:2869–2873 (1995)). The percentage of cells in each phase of the cell cycle was determined by analyzing data with the computer program CELLFIT (Becton Dickinson).

EXAMPLE 1

Identification of cDNA Specifically Expressed in Hematopoietic Cells Induced with IL-3, IL-5 and/or GM-CSF Mitogen induction of DUB-1 mRNA: Hematopoietic growth factors, such as IL-3 and erythropoietin (EPO), stimulate different cellular responses by inducing different sets of immediate-early genes. Growth in IL-3 results in proliferation (J. N. Ihle, *In T. Kishimoto (ed.), Interleukins: Molecular Biology and Immunology*. Karger, Basel p.65–106 (1993)); growth in EPO results in proliferation and erythroid-specific differentiation (Nijhof et al., *Exp. Hematol.* 15:779–784 (1987)). We have recently described one cell line, Ba/F3-EPO-R, that has functional receptors for both murine IL-3 and EPO (Liboi et al., *Proc. Natl. Acad. Sci. USA* 90:11351–11355 (1993); Carroll et al., *Proc. Natl. Acad. Sci. USA* 92:2869–2873 (1995)). Using this cell line, we initially identified cDNAs that were inducible by either IL-3 or EPO by the differential display method (Liang and Pardee, *Science* 257:967–971 (1992); Liang et al., *Nucle. Acids Res.* 21:3269–3275 (1993)).

cDNA (designated DUB-1 or T14) was specifically expressed in cells induced with IL-3. This RT-PCR fragment (298 bp) was isolated from a differential display gel and used as a probe to identify a specific IL-3 inducible MRNA. An MRNA (3.1 kb) was detected in cells growing in IL-3. When cells were switched to EPO, the mRNA disappeared after 8 hours. In addition, when Ba/F3-EPO-R cells were depleted of IL-3 for 8 hours, the T14 mRNA disappeared. When the cells were restimulated with IL-3, the T14 mRNA, like the c-myc mRNA, was induced after 1 hour. The presence of cycloheximide (CHX) (10 µg/ml) plus IL-3 resulted in a superinduction of the T14 mRNA. Expression reached a maximum at 3 hours post stimulation and declined by 6 hours.

The T14 probe was used to detect mRNA expression in murine cell lines and tissues. The mRNA was detected in the IL-3 dependent early hematopoietic progenitor cell lines, Ba/F3 and FDCP1, but not in the myeloid cell line, 32D. Other cell lines, including MEL, CTLL, and 011 (megakaryocyte) lacked the T14 mRNA. The T14 mRNA was not detected in normal adult murine tissue samples.

Induction of DUB-1 mRNA by Other Growth Factors: GM-CSF, IL-5 and IL-4 responsive cell lines were generated and tested for induction of DUB-1 MRNA as described below. Ba/F3-GMCSFRa cells were generated by stable transfection of Ba/F3 cells with the cDNA encoding the murine GMCSFRA (Park et al., *Proc. Natl. Acad. Sci. USA* 89:4295–4299 (1992)). Ba/F3-GMCSFRα cells grow in either murine IL-3 or murine GM-CSF. Ba/F3-IL-5Rα cells were generated by stable transfection of Ba/F3 cells with the cDNA encoding the murine IL-5Rα chain (Takaki et al., *EMBO. J.*:2833–2838 (1991), Takaki et al., *EMBO. J.* 9: 4367–4374 (1990), Devos et al., *Science* 264:1415–1421 (1994)). Ba/F3-IL-5Rα cells grow in either murine IL-3 or murine IL-5. Ba/F3-IL-4R cells were generated by stable transfection of Ba/F3 cells with the cDNA encoding the human IL-4R. Ba/F3-IL-4R cells grow in either murine IL-3 or human IL-4 (Seldin, et al., *Proc. Natl. Acad. Sci.* 91: 2140–2144). All Ba/F3 subclones were maintained in RPMI 1640 medium supplemented with 10% fetal calf serum (FCS) and 10% conditioned medium from WEHI-3B cells as a source of murine IL-3.

The induction assays were carried out by washing the various Ba/F3 subclones three times with PBS, growing the cells at 37° C. without growth factor for eight hours, known as starving the cells, and then restimulating the cells with the appropriate cytokine. That is, Ba/F3-EPO-R cells were restimulated with both human EPO (1 pM=10 mU/ml) (Genetics Institute) and murine IL-3; Ba/F3-GM-CSFRα cells were restimulated with murine GM-CSF (Prepro Tech. Inc.); Ba/F3-IL-5Rα cells were restimulated with murine IL-5 (R and D Systems); and Ba/F3-IL-4R cells were restimulated with human IL-4 (Genzyme).

Murine IL-3, but not EPO, induced DUB-1 mRNA in Ba/F3-EPO-R cells. Both murine GM-CSF and murine IL-3 induced DUB-1 mRNA in Ba/F3-GM-CSFRa cells. Similarly, murine IL-5 and murine IL-3 induced DUB-1 mRNA in Ba/F3-IL-5Rα cells. Murine IL-3, but not human IL-4, induced DUB-1 mRNA in Ba/F3-IL-4R cells. Since the βc subunit of the IL-3R functionally interacts with the α chains of the IL-3R, the GM-CSFR and the IL-5R (Sato et al., *Curr. Opin. Cell Biol.* 6:174–179 (1994); Gearing et al., *EMBO. J.* 8:3667–3676 (1989); Hayashida et al., *Proc. Natl. Acad. Sci. USA* 87:9655–9659 (1990); Kitamura et al., *Proc. Natl. Acad. Sci. USA* 88:5082–5086 (1991); Kitamura et al., *Cell* 66:1165–1174 (1991)) these results suggest that DUB-1 is specifically induced by the βc subunit.

DUB-1 Sequence Analysis: Using the T14 partial cDNA as a probe, a cDNA library prepared from Ba/F3-EPO-R cells growing in IL-3 was screened. Three independent CDNA clones that hybridized with the T14 probe were isolated. All three contained approximately 2.6 kb and had full length cDNA inserts. The longest cDNA was 2674 bp and contained a 1581 bp open reading frame (FIG. 1). There are two stop codons and 183 bp of 5' untranslated region (UTR).

EXAMPLE 2

DUB-1 Encodes a Functional Deubiquitinating Enzyme

In order to determine whether DUB-1 has deubiquitinating activity, DUB-1 was expressed as a fusion protein. The open reading frame of DUB-1 was subcloned, in frame, into the bacteria expression vector, PGEX. pGEX-DUB-1 was co-transformed into E. coli (MC1066) with a plasmid encoding the protein, Ub-Met-βgal, in which ubiquitin is fused to the N-terminus of β-galactosidase. As shown by immunoblot analysis, two independent cDNA clones encoding glutathione-S-transferase (GST)-DUB-1 fusion protein resulted in cleavage of Ub-Met-βgal to an extent comparable to that observed with Ubpl, a known yeast deubiquitinating enzyme (Papa and Hochstrasser, Nature 366:313–319, (1993)). As control, pGEX vector alone failed to result in ubiquitin cleavage. A mutant DUB-1 polypeptide, containing a C60S mutation, was unable to cleave the Ub-Met-βgal substrate. Taken together, these results demonstrate that DUB-1 has deubiquitinating activity and that Cys60 is critical for its thiol protease activity.

EXAMPLE 3

Assessment of DUB-1 Function

Further work showed that induced expression of DUB-1 rrests cell growth in the Gi phase of the cell cycle. Initial attempts to obtain stable cell lines that constitutively express DUB-1 were unsuccessful, raising the ossibility that DUB-1 interferes with cell growth and/or viability and, therefore, DUB-1 was expressed in Ba/F3 cells using a steroid-(dexamethasone)inducible promoter. Twelve qpt-resistant Ba/F3 subclones were generated after transfection with either pMSG/DUB-1 or mutant pMSG/DUB-1(C60S), which encodes the inactive enzyme. Dexamethasone (0.1 μM) induced DUB-1 mRNA in all transfected cells, but not in parental or mock transfected cells.

The induced DUB-1 polypeptide was identified using a polyclonal antiserum raised against the GST-DUB-1 fusion protein. Dexamethasone induced DUB-1 or DUB-1(C60S) in the transfected Ba/F3 cells. These proteins had the same electrophoretic mobility (59 kD) as full length DUB-1 polypeptide synthesized by in vitro translation.

After dexamethasone induction, cells expressing DUB-1 failed to proliferate, but remained viable in IL-3 medium. In contrast, dexamethasone-induced cells expressing DUB-1 (C60S) proliferated normally in IL-3. In order to exclude the possibility that the growth inhibitory effects were due to nonspecific toxicity, dexamethasone was removed. Cells expressing wild-type DUB-1 resumed normal proliferation 48 hours following dexamethasone withdrawal. The percentage of cells in G1, S, and G2/M were: DUB-1 -dex (32%, 61%, 7%), +dex (82%, 14%, 4%); DUB-1(C60S) -dex (35%, 57%, 8%), +dex (35%, 57%, 8%). Data shown are representative of at least three separate dexamethasone induction experiments.

Cell cycle analysis demonstrated that the majority of cells were arrested in G1 following dexamethasone induction of DUB-1. This concentration of dexamethasone (0.1 μM) slightly reduced IL-3 dependent proliferation of parental Ba/F3 cells or DUB-1(C60S) expressing cells (to 80% of maximum), but it completely blocked proliferation of the wild-type DUB-1 expressing cells. These results show that wild-type DUB-1 therefore acts as a growth suppressor in Ba/F3 cells.

EXAMPLE 4

Expression of DUB-1 mRNA

Ba/F3-EPO-R cells arrest in early Gi when deprived of IL-3 for 12 hours and can be induced to reenter the cell cycle synchronously by readdition of growth factor (Carroll et al., Proc. Natl. Acad. Sci. USA 92:2869–2873 (1995)). DUB-1 mRNA was induced following 30 to 60 minutes in IL-3 but rapidly decreased in abundance before the completion of G1 phase. The kinetics of induction of DUB-1 (T14) mRNA in the cell cycle were similar to that of c-myc. Cyclin D2 mRNA accumulated later in GI phase, as previously described (Matsushime et al., Cell 65:701–713 (1991)). DUB-1 mRNA levels rapidly declined after 8 hours. In contrast, c-myc and cyclin D2 mRNA levels remained elevated as cells entered S phase (12 hours). The expression of GAPDH showed minimal oscillation throughout the cell cycle.

EXAMPLE 5

Isolation of a Full-Length Genomic Clone for DUB-1

Methods and Materials

Cells and Cell Culture

Ba/F3 is an IL-3 dependent murine pro-B cell line (Glotzer et al., Nature 349:132–138 (1991)). The Ba/F3-EPO-R cell line grows in either IL-3 or EPO, as previously described (Scheffner et al., Cell 63:1129–1136 (1990)). Ba/F3 and Ba/F3-EPO-R cells were maintained in RPMI 1640 medium supplemented with 10% fetal calf serum (FCS) and 10% conditioned medium from WEHI-3B cells as a source of IL-3. For growth factor stimulation, Ba/F3-EPO-R cells were washed in RPMI 1640 and treated with either 0.05 U/ml EPO or 10 pM recombinant IL-3.

Northern Analysis

RNA samples (10–30 μg) were electrophoresed on denaturing formaldehyde gels and blotted onto Duralon-UV membranes (Stratagene). The cDNA inserts, purified from agarose gels (Qiagen), were radiolabeled (Schwob et al., Cell 79:233–244 (1994)) and hybridized for 1 hour to the membranes in a 60° C. oven. Hybridized filters were washed at room temperature in 0.1×SSC and 0.1% sodium dodecyl sulfate.

Cloning of the DUB-1 Gene and Construction of Promoter Plasmids

A mouse genomic library prepared in Lambda FIX II (Stratagene, La Jolla, Calif.) was screened with the ORF region of the DUB-1 cDNA. The probe was labeled with $^{32}$P-dCTP by the random primer method (Pharmacia), and hybridization was performed in 0.8M NaCl, 0.02M Pipes pH6.5, 0.5% SDS, 50% deionized formamide and 100 μg/ml denatured, sonicated salmon sperm DNA for 16 hours at 42° C. A clone encompassing the DUB-1 gene and its 5' and 3'-flanking sequences was recovered as a 13 Kb Not I fragment. The clone was mapped by restriction enzyme digestion and partially sequenced by the dideoxy DNA sequencing protocol (USB).

A 1.5 Kb Spe I/Xba I fragment in the 5'-flanking region of DUB-1 was subcloned into pGL2Basic plasmid vector (Pharmacia). This pGL2Basic plasmid contains the luciferase reporter gene with no promoter. Additional DNA fragments from the 5'-flanking region of the DUB-1 gene were generated by PCR using pairs of 20-mer oligonucleotides designed according to the genomic DNA sequence. These fragments were subcloned into the pGL2Promoter plasmid vector (Pharmacia), which contains the SV40 basic promoter and the luciferase reporter gene.

Transient Transfection and Transactivation Experiments

All plasmid DNAs were purified using Qiagen columns (Qiagen Inc., CA). The indicated Ba/F3 subclones (10' cells per transfection) were transfected by electroporation with 10 μg of a test plasmid. The cells were starved by depletion of cytokine for 5 hours before electroporation. After electroporation cells were divided into pools and restimulated with the indicated cytokines at variable concentrations. Luciferase levels were assayed after 12 hours of stimulation by vendor specifications (Luciferase Assay Kit, Analytical Luminescence Laboratory, San Diego, Calif.). Each construct was tested at least three times by independent transfection.

Interspecific Mouse Backcross Mapping

Interspecific backcross progeny were generated by mating (C57BL/6J×M. spretus) F1 females and C57BL/6J males as described previously (Budarf et al., *Genomics* 8:575–578 (1990); Copeland et al., *Trends Genet.* 7:113–118 (1991)). The strategies described by Budarf et al. and Copeland et al. were used to map the DUB-1, DUB-2 and DUB-3 genes to mouse chromosome 7, in a region corresponding to human chromosome 11;15.

EXAMPLE 6

DUB-2 Encodes a Functional Deubiquitinating Enzyme

In order to determine whether DUB-2 has deubiquitinating activity, DUB-2 was expressed as a GST fusion protein. The open reading frame of DUB-2 was subcloned, in frame, into the bacteria expression vector, PGEX. pGEX-DUB-2 was co-transformed into *E. coli* (MC1061) with a plasmid encoding the protein, Ub-Met-βgal, in which ubiquitin is fused to the N-terminus of β-galactosidase. As shown by immunoblot analysis, a cDNA clone encoding glutathione-S-transferase (GST)-DUB-2 fusion protein resulted in cleavage of Ub-Met-βgal to an extent comparable to that observed with GST-DUB-1 (Example 2). As control, cells with the pGEX vector or pBluescript vector with a nontranscribed DUB-2 insert failed to cleave Ub-Met-βgal. A mutant DUB-2 polypeptide, containing a C60S mutation, was unable to cleave the Ub-Met-βgal substrate. Taken together, these results demonstrate that DUB-2 has deubiquitinating activity and that Cys60 is critical for its thiol protease activity.

EXAMPLE 7

Identification of cDNA Specifically Expressed in Hematopoietic Cells Induced with IL-2 and Isolation of a Full-Length Genomic Clone for DUB-2

Mitogen Induction of DUB-2 mRNA. In the process of cloning the DUB-1 gene, a large family of related DUB genes that cross-hybridized with the DUB-1 cDNA probe was identified. We reasoned that other cytokines might induce these related, but functionally distinct DUB enzymes. Here we report the identification of an IL-2 inducible DUB enzyme, DUB-2.

CTLL-2 cells were maintained in RPMI 1640 medium supplemented with 10% (vol/vol) FCS and 2 U/ml of murine recombinant IL-2 (Boehringerr-Mannheim). CTLL cells were starved in RPMI 1640–10%FCS for an 8 hour period and restimulated for various times with IL-2 containing medium. An inducible 2.5 kb mRNA (DUB-2) was identified that weakly hybridized with the full length DUB-1 cDNA probe. The 2.5 kb DUB-2 mRNA was distinct from the 2.7 kb DUB-1 mRNA. DUB-2 mRNA levels were rapidly induced within 30 minutes of IL-2 restimulation but declined after 6 hours, similar to the induction kinetics observed for DUB-1 MRNA in IL-3, IL-5 and/or GM-CSF responsive cells. The DUB-2 mRNA was superinduced in the presence of cycloheximide (10 μg/ml), thereby defining DUB-2 as an IL-2 specific immediate-early gene product.

DUB-2 cDNA was isolated by RT-PCR, using total cellular RNA prepared from IL-2 stimulated CTLL cells. Primers were derived from the DUB-1 sequence. The 5' primer was, 5'TTTGAAGAGGTCTTTGGAGA3' (SEQ ID NO:49), which is upstream of the ATG START codon. The 3' primer was, 5'GTGTCCACAGGAGCCTGTGT3' (SEQ ID NO:51), which is downstream of the TGA STOP codon. The PCR reaction was performed at 94° C. for one minute, 55° C. for one minute, and 72° C. for two minutes for a total of 35 cycles. The amplified cDNA was cloned into PCRII (Invitrogen) and sequenced by the dideoxynucleotide method. PCR errors were eliminated by confirming the sequence of six independent cDNA clones. The DUB-2 cDNA product was amplified by RT-PCR using mRNA derived from IL-2 stimulated CTLL cells. Six independent RT-PCR products were compared by sequence analysis and all were identical.

Figure 15:
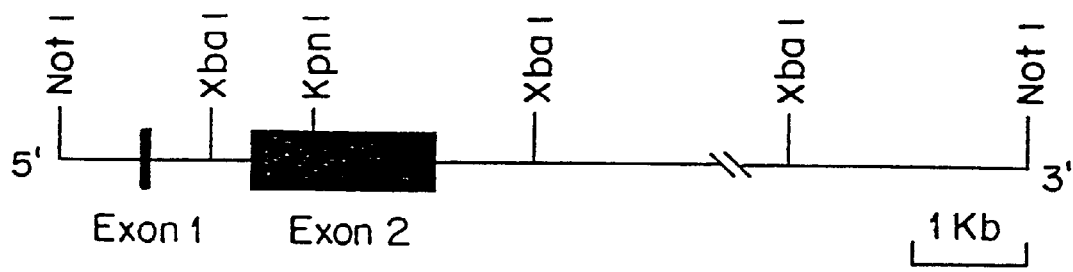
FIG. 15 is a schematic representation of the genomic organization of the DUB-2 gene, including a partial restriction map.
Figure 16:
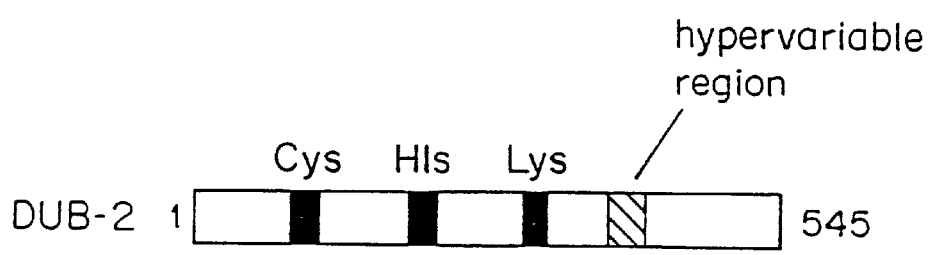
FIG. 16 is a schematic representation of DUB-2. Individual domains refer to the Cys domain (amino acid 52–69), the His domain (amino acid 290–395) the Lys domain (amino acid 374–384), and the hypervariable region.

In order to verify the sequence of the DUB-2 cDNA and to obtain additional 5' and 3' untranslated sequence, we isolated a full-length genomic clone for murine DUB-2 (FIG. 15). The nucleotide sequence of the DUB-2 cDNA and the DUB-2 genomic clone were identical within the open reading frame. The DUB-2 gene contains a small exon (exon 1) encoding amino acids 1–9 and a larger exon (exon 2) encoding amino acids 10–545, similar to the genomic organization of the DUB-1 gene. The sequence of the intron-exon junction conforms to a consensus sequence for a eukaryotic splice junction. A region of the genomic clone 5' to the ATG START site was sequenced and found to contain a STOP codon. This sequence is shown as the 5' untranslated sequence of the DUB-2 cDNA clone (bp 1 to 198) (FIG. 14).

Results

DUB-1 Is a Hematopoietic-Specific, Cytokine-Inducible Immediate-Early Gene

Hematopoietic growth factors, such as IL-3 and erythropoietin (EPO), stimulate different cellular responses by inducing different sets of immediate-early genes. Growth in IL-3 results in proliferation (J. N. Ihle, *In T. Kishimoto (ed.). Interleukins: Molecular Biology and Immunology.* Karger, Basel p.65–106 (1993)); growth in EPO results in proliferation and erythroid-specific differentiation (Nijhof et al., *Exp. Hematol.* 15:779–784 (1987)). The cell line, Ba/F3-EPO-R, has functional receptors for both murine IL-3 and EPO (Liboi et al., *Proc. Natl. Acad. Sci. USA* 90:11351–11355 (1993); Carroll et al., *Proc. Natl. Acad. Sci. USA* 92:2869–2873 (1995)). Using this cell line, cDNAs that were inducible by either IL-3 or EPO were identified by the differential display method (Liang and Pardee, *Science* 257:967–971 (1992); Liang et al., *Nucle. Acids Res.* 21:3269–3275 (1993)).

One of these cDNAs (DUB-1) was specifically expressed in cells induced with IL-3. The DUB-1 mRNA (2.7 kb) was detected in cells growing in IL-3. When cells were switched to EPO, the mRNA disappeared after 8 hours. In addition, when Ba/F3-EPO-R cells were depleted of IL-3 for 8 hours, the DUB-1 MRNA disappeared. When the cells were restimulated with IL-3, the DUB-1 mRNA, like the c-myc mRNA, was induced after 1 hour. The presence of cycloheximide (CHX) (10 μg/ml) plus IL-3 resulted in a superinduction of the DUB-1 mRNA. Expression reached a maximum at 3 hours post stimulation and declined by 6 hours.

The full-length DUB-1 probe was used to detect mRNA expression in murine cell lines and tissues. The mRNA was detected in the IL-3 dependent early hematopoietic progenitor cell lines, Ba/F3 and FDCP1, but not in the myeloid cell line, 32D. Other cell lines, including MEL, CTLL, and 011 (megakaryocyte) lacked the DUB-1 mRNA. The DUB-1 mRNA was not detected in normal adult murine tissue samples.

In addition, DUB-1 mRNA is also be induced by IL-5 and/or GM-CSF. Induction by these growth factors was tested as described in Example 1. GM-CSF, IL-5 and IL-4 responsive cells lines were generated by transfecting Ba/F3 cells with cDNA encoding either murine GM-CSFRα, murine IL-5Rα or human IL-4R to give Ba/F3-GM-CSFRα, Ba/F3-IL-5Rα or Ba/F3-IL-4R cells respectively. Induction assays were carried out by washing the various Ba/F3 subclones described above with PBS, growing the cells at 37° C. without growth factor, and restimulating the cells with the appropriate cytokine.

As reported earlier murine IL-3, but not EPO, induced DUB-1 mRNA in Ba/F3-EPO-R cells. In addition, both murine GM-CSF and murine IL-3 induced DUB-1 mRNA in Ba/F3-GM-CSFRα cells. Similarly, murine IL-5 and murine IL-3 induced DUB-1 mRNA in Ba/F3-IL-5Rα cells. Murine IL-3, but not human IL-4, induced DUB-1 mRNA in Ba/F3-IL-4R cells. Since the βc subunit of the IL-3R functionally interacts with the α chains of the IL-3R, the GM-CSFR and the IL-5R (Sato et al., Curr. Opin. Cell Biol. 6:174–179 (1994); Gearing et al., EMBO. J. 8:3667–3676 (1989); Hayashida et al., Proc. Natl. Acad. Sci. USA 87:9655–9659 (1990); Kitamura et al., Proc. Natl. Acad. Sci. USA 88:5082–5086 (1991); Kitamura et al., Cell 66:1165–1174 (1991) these results suggest that DUB-1 is specifically induced by the βc subunit.

DUB-1 Genomic Organization

A total of $1\times10^6$ recombinant phage were screened under low stringency conditions with the full-length DUB-1 cDNA, and five positive clones were identified. By restriction analysis and hybridization with $^{32}$P-labeled oligonucleotides complementary to different segments of the cDNA, one phage clone was found to contain the full-length DUB-1 coding region. The four other clones contained genes with considerable homology to DUB-1 and are presumably DUB-1 family members. A schematic diagram of the DUB-1 gene and a restriction map are shown (FIG. 3). The gene contains a small exon (exon 1) encoding the first 9 amino acids of DUB-1 and a larger exon (exon 2) encoding amino acids 10–526 of DUB-1. The coding region is identical to the sequence of the DUB-1 cDNA clone. The sequence of the intron-exon junction conforms to a consensus sequence for a eukaryotic splice junction. The 1.5 kb sequence of the DUB-1 gene, 5' to the ATG start site of translation initiation, is shown in (FIG. 4). This sequence contains a TATA box (−320) and a candidate STAT-binding element at position (−1310).

Identification of a Functional Promoter in the DUB-1 Gene

The Ba/F3-EPO-R, Ba/F3-IL-5R, Ba/F3-IL4R and Ba/F3-GM-CSF cells described in Example 1, were transiently transfected with a plasmid containing the 1.5 kb 5' flanking region of the DUB-1 gene (T14P1.5 kb), driving a luciferase reporter. Luciferase activity was increased in a dose-dependent manner by IL-3, GM-CSF and IL-5 but not human IL-4 or EPO. In addition, luciferase activity was not increased by IFN-α or IFN-γ, despite the expression of functional interferon receptors on Ba/F3 cells. No luciferase activity was observed when vector alone was transfected. Taken together, these data verify that activation of the βc subunit is required for induction of the DUB-1 gene. In addition, these results demonstrate that the 1.5 kb 5' flanking region of the DUB-1 gene contains a functional promoter and elements that mediate βc-dependent transcriptional activation.

Identification of a Minimal βc-Responsive Enhancer Element

Figure 19A:
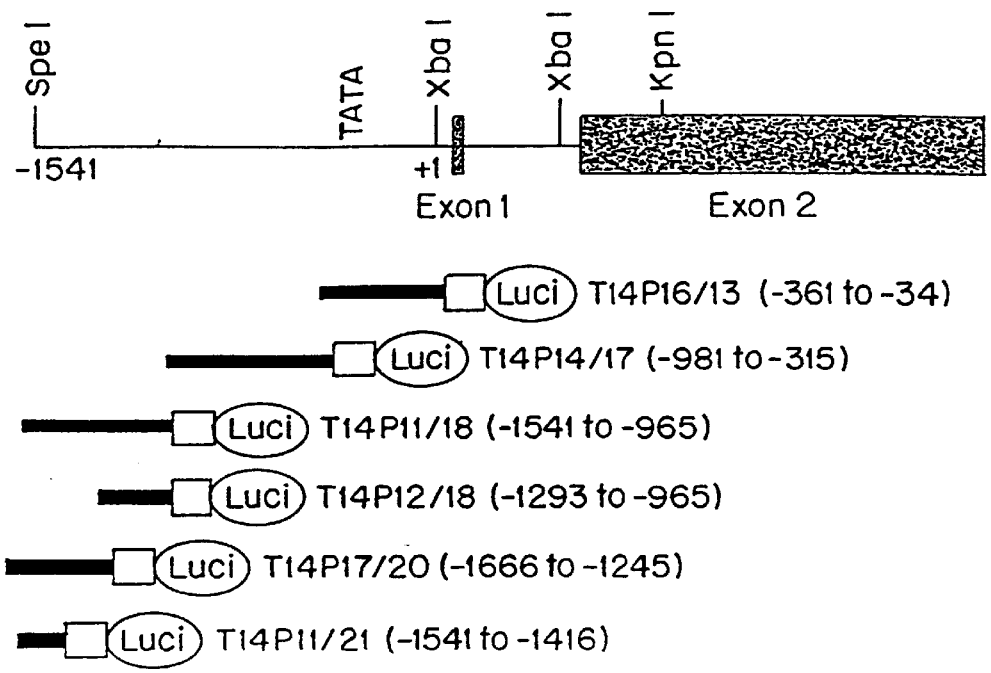
FIG. 19A is a representation of the variable DNA fragments of the DUB-1 promoter region which were subcloned into the pGL2 Promoter vector and tested for enhancer activity.
Figure 19B:
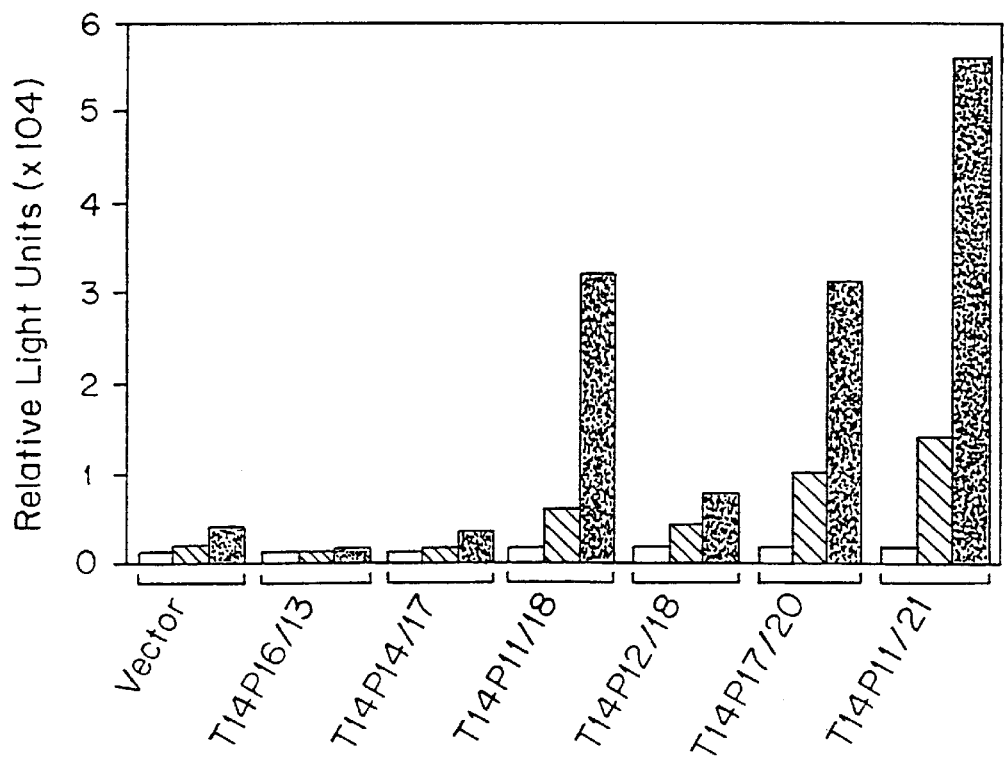
FIG. 19B shows the results of the luciferase activity assay in cells transfected with the constructs shown in A. The cells were starved and restimulated with no growth factor (open bars), 1 pM of IL-3 (striped bars), or 10 pM of IL-3 (solid bars). Luciferase assays were performed after 12 hours.

To further delineate the specific DNA sequence required for IL-3 induction, we next divided the 1.5 kb region into several DNA fragments (FIG. 19). Each fragment was subcloned into the vector, pGL2Promoter, which contains the luciferase gene driven by an SV40 promoter, without an enhancer (FIG. 19A). The fragments T14Pll/18, T14P17/20 and T14Pll/21 had IL-3 dependent enhancer activity. Stimulation of cells with 10 pM of IL-3 resulted in 3 to 4 fold higher luciferase activity than stimulation with 1 pM IL-3. Stimulation of cells with EPO resulted in no increased luciferase activity. The fragments T14P14/17, T14P16/13 and T14P12/18 had no enhancer activity. Since the three fragments with functional activity (T14Pll/18, T14P17/20 and T14P11/21) overlap at the region −1541 to −1416, this region (125 bp) was initially identified as a βc-specific inducible enhancer.

Figure 20A:
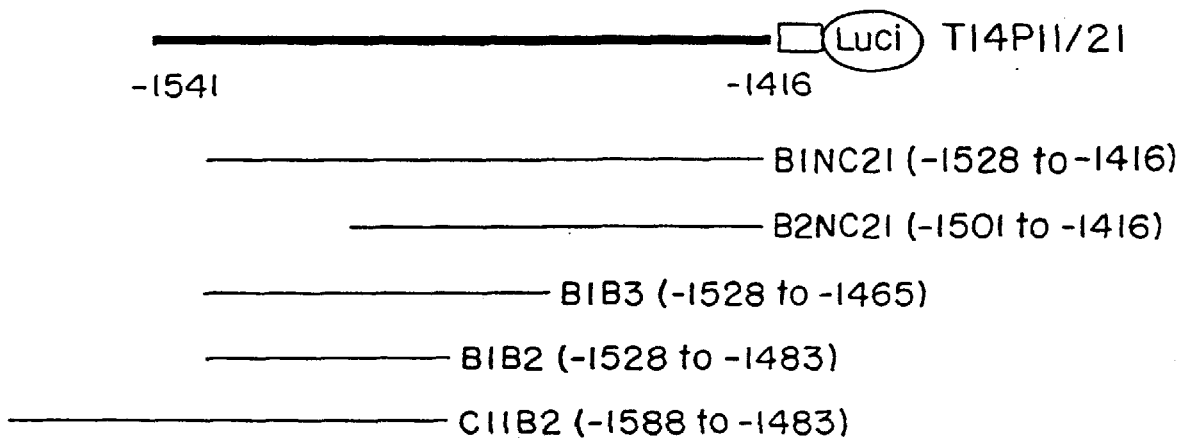
FIG. 20A is a representation of the variable DNA fragments which were generated by PCR and subcloned into the pGL2Promoter vector.
Figure 20B:
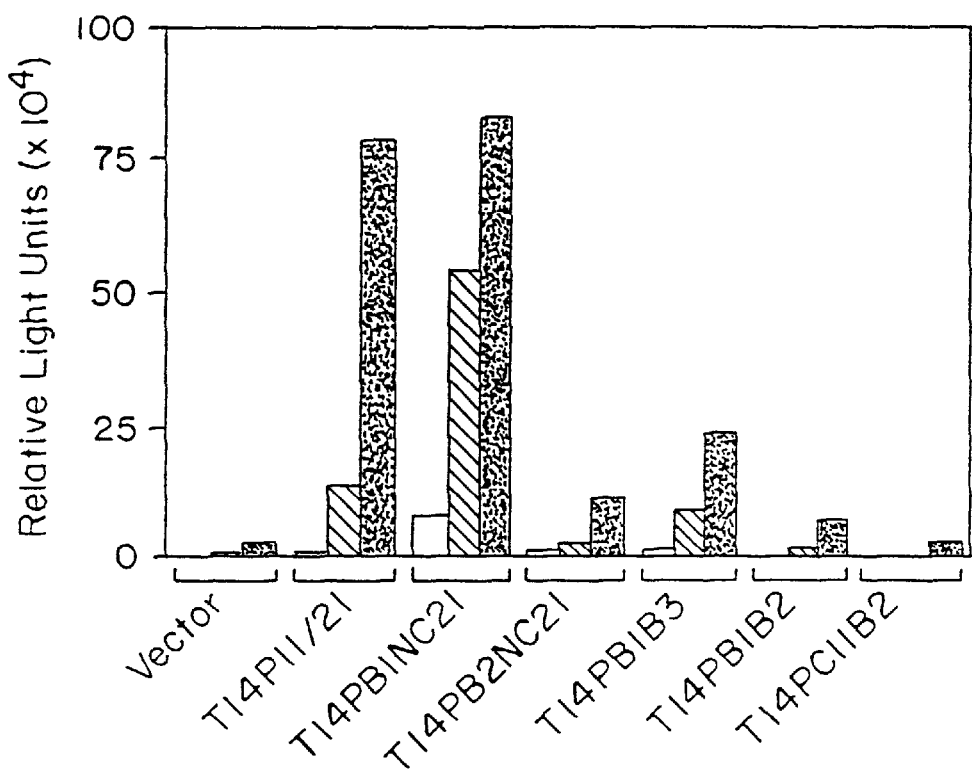
FIG. 20B shows the results of the luciferase activity assay in cells transfected with constructs shown in A. The cells were starved and restimulated with no growth factor (open bars), 1 pM of IL-3 (striped bars), or 10 pM of IL-3 (solid bars). Luciferase assays were performed after 12 hours.

We next performed further truncations of the DUB-1 enhancer region (Tl4Pll/21) (FIG. 20). A region of 112 base pairs (BlNC21), corresponding to base pair −1528 to −1416, had activity comparable to the T14Pll/21 fragment. Further truncations within this region generated DNA fragments with only partial activity. For instance, the B1B3 fragment (5' end) demonstrated enhancer activity that was 28% of the activity of the T14P11/21 fragment. The B2NC21 fragment (3' end) had enhancer activity that was 14% of the activity of the T14P11/21 fragment. These data demonstrate that the 112 base pair fragment is the minimal region required for βc-specific DUB-1 induction. This fragment was not activated by EPO or IL-4 stimulation. The 112 base pair sequence (FIG. 15, underlined) contained no known enhancer consensus sequences and therefore, may contain a novel βc-specific transcriptional activation element.

DUB-2 Is an IL-2 Specific Immediate-Early Gene

As reported herein DUB-1 is an IL-3, IL-5 and/or GM-CSF-inducible immediate-early gene. In order to identify related mRNAs that are specifically induced by other growth factors, CTLL cells were removed from growth factor and restimulated with IL-2. An inducible 2.5 kb mRNA (DUB-2) was identified that weakly hybridized with the full length DUB-1 cDNA probe. The 2.5 kb DUB-2 mRNA was distinct from the 2.7 kb DUB-1 mRNA. DUB-2 mRNA levels were rapidly induced within 30 minutes of IL-2 restimulation but declined after 6 hours, similar to the induction kinetics observed for DUB-1 mRNA. The DUB-2 mRNA was superinduced in the presence of cycloheximide (10 μg/ml), thereby defining DUB-2 as an IL-2-inducible immediate-early gene.

The DUB-2 mRNA (2.5 kb) was expressed in the murine T-cell lines 3DO (Marrack et al., J. Exp. Med. 158:1077–1091 (1983)) but was not expressed in other IL-3 dependent murine hematopoietic cell lines including 32D and Ba/F3. The DUB-2 mRNA was also expressed in murine primary T-cells but was not expressed in other normal murine tissues.

Using oligonucleotide primers derived from the DUB-1 cDNA sequence and total RNA from IL-2 stimulated CTLL cells, we isolated a DUB-2 cDNA by RT-PCR. The cDNA fragment (bp 198 to 1873) contained a full-length open reading frame. Six independent cDNA clones derived from IL-2 stimulated CTLL cells were sequenced, and all were DUB-2. The DUB-2 CDNA was not isolated by RT-PCR from unstimulated CTLL cells or from IL-3 stimulated Ba/F3 cells. In addition, six independent cDNA clones derived by RT-PCR from IL-3 stimulated Ba/F3 cells were all DUB-1.

In order to verify the sequence of the DUB-2 CDNA and to obtain additional 5' and 3' untranslated sequence, a full-length genomic clone for murine DUB-2 (FIG. 15) was isolated. The nucleotide sequence of the DUB-2 cDNA and the DUB-2 genomic clone were identical within the open reading frame. The DUB-2 gene contains a small exon (exon 1) encoding amino acids 1–9 and a larger exon (exon 2) encoding amino acids 10–545, similar to the genomic organization of the DUB-1 gene. The sequence of the intron-exon junction conforms to a consensus sequence for a eukaryotic splice junction. A region of the genomic clone 5' to the ATG START site was sequenced and found to contain a STOP codon. The sequence is shown as the 5' untranslated sequence of the DUB-2 cDNA clone (bp 1 to 198) FIG. 14.

The DUB-2 cDNA encodes a polypeptide of 545 amino acids (62 kD) that has 93% amino acid similarity and 88% identity to DUB-1 (FIG. 17). Both DUB-1 and DUB-2 polypeptides contain the highly conserved Cys and His domains. These domains probably help form the enzyme active site. The likely active site nucleophile of DUB-2 is a cysteine residue (C60) in the Cys domain that is found in all known ubp family members and is also present in DUB-1. In addition, DUB-1 and DUB-2 have a lysine rich region (Lys domain; amino acids 374 to 384 of DUB-2) and a hypervariable region (amino acid 431 to 451 of DUB-2), in which the DUB-1 and DUB-2 sequences diverge considerably. The hypervariable region of DUB-2 contains a duplication of the eight amino acid sequence, PQEQNHQK (SEQ ID NO:51).

DUB-1 and DUB-2 Encode a Functional Deubiquitinating Enzyme

Assessment of both DUB-1 (Example 2) and DUB-2 (Example 6) showed that they are functional deubiquitinating enzymes. When expressed as fusion proteins with glutathione-S-transferase (GST-DUB-1 and GST-DUB-2 fusion proteins), both DUB-1 and DUB-2 cleaved the protein Ub-Met-βgal, in which ubiquitin is fused to the N-terminus of β-galactosidase, with comparable results. Mutant DUB-1 and DUB-2 polypeptides, containing a C60S mutation, was unable to cleave the Ub-Met-βgal substrate. Taken together these results demonstrate that DUB-1 and DUB-2 have comparable deubiquitinating activity and that the Cys 60 is critical in both for thiol protease activity.

DUB-1, DUB-2 and DUB-3 Chromosomal Mapping

The chromosomal location of DUB-1, DUB-2 and DUB-3 was determined by interspecific backcross analysis using progeny derived from matings of (C57BL/6J×M. spretus) F1×C57BL/6J mice. C57BL/6J and M. spretus DNAs were digested with several enzymes and analyzed by Southern blot hybridization for informative restriction fragment length polymorphisms (RFLPs) using either the DUB-1, DUB-2 or DUB-3 specific probes. The mapping results indicate that DUB-1, DUB-2 and DUB-3 are all located on mouse chromosome 7 consistent with the hypothesis that the DUB genes are all closely linked on mouse chromosome 7 and have evolved through a series of tandem gene duplication events. The mapping results also indicate that the DUB gene subfamily is unlinked to Tre2 (Nakamura et al., *Oncogene* 7:733–741 (1992)) or unp (Gupta et al., *Oncogene* 8:2307–2310 (1993)).

This region of mouse chromosome 7 containing the DUB genes shares homology with human chromosome 11p15, evidence that the human homolog of DUB-1 and DUB-2 reside on human chromosome 11p. This region of human chromosome 11 is a frequent site of translocations in human leukemias (Beau et al., *Proc, Natl. Acad. Sci. USA* 83:9744–9748 (1986); McGuire et al., *Mol. Cell. Biol.* 9:2124–2132 (1989); Boehm et al., *EMBO. J.* 7:285–294 (1988)) and is a site of a tumor suppressor locus (Koufos et al., *Nature* 316:330–334 (1985); Koufos et al., *Am J. Hum. Genet.* 44:711–719 (1989)).

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. An isolated DNA comprising a nucleotide sequence selected from the group consisting of:
 a) SEQ ID NO.: 1;
 b) a complement of SEQ ID NO.: 1;
 c) SEQ ID NO.: 21;
 d) a complement of SEQ ID NO.: 21
 e) SEQ ID NO.: 37;
 f) a complement of SEQ ID NO. 37; and
 g) an active portion of any one of a)–f).

2. An isolated DNA which encodes an amino acid sequence selected from the group consisting of:
 a. SEQ ID NO.: 2;
 b. SEQ ID NO.: 9; and
 c. SEQ ID NO.: 38.

3. An isolated DNA comprising the sequence of base pairs numbered 1280–1578 of SEQ ID NO.: 1 as represented in FIG. 1.

4. The isolated DNA of claim 1 further comprising a promoter.

5. The isolated DNA of claim 1 further comprising an enhancer.

6. An isolated DNA encoding a variant of a DUB enzyme encoded by a nucleotide sequence of claim 1 whose expression in hematopoietic cells results in arrest of growth of the hematopoietic cells in the G0/G1 phase of the cell cycle, wherein the variant lacks a conserved cysteine required for thiol protease activity and, when expressed in hematopoietic cells, does not induce arrest of growth of the hematopoietic cells in the G0/G1 phase of the cell cycle.

7. An isolated RNA encoded by a nucleotide sequence selected from the group consisting of:
 a) SEQ ID NO.: 1;
 b) SEQ ID NO.: 21;
 c) SEQ ID NO.: 37; and
 d) an active portion of any one of a)–c).

8. A host cell containing a heterologous nucleic acid encoding a DUB enzyme.

9. A host cell of claim 8, wherein the heterologous nucleic acid encoding a DUB enzyme consists of a nucleotide sequence selected from the group consisting of:
 a) SEQ ID NO.: 1 or an active portion thereof;
 b) SEQ ID NO.: 21 or an active portion thereof;
 c) SEQ ID NO.: 37 or an active portion thereof;
 d) DNA encoding DUB-1 enzyme of SEQ ID NO.: 2 or an active portion thereof;
 e) DNA encoding DUB-3 enzyme of SEQ ID NO.: 9 or an active portion thereof;
 f) DNA encoding DUB-2 enzyme of SEQ ID NO.: 38 or an active portion thereof;
 g) DNA encoding DUB-4 enzyme or an active portion thereof; and
 h) DNA encoding DUB-5 enzyme or an active portion thereof.

10. A host cell of claim 8 wherein the DNA encodes a DUB enzyme which is expressed in hematopoietic cells induced with IL-3, IL-5 and/or GM-CSF.

11. A host cell of claim 8 wherein the DNA encodes a DUB enzyme which is cytokine inducible.

12. A host cell of claim 8 wherein the DNA encodes a DUB enzyme which is IL-2 inducible.

13. A nucleic acid construct for expressing a DUB enzyme in a cell, comprising a nucleic acid encoding the DUB enzyme to be expressed.

14. A nucleic acid construct of claim 13 which is a DNA construct.

15. The DNA construct of claim 14, wherein the DNA encoding a DUB enzyme is selected from the group consisting of:
 a) SEQ ID NO.: 1 or an active portion thereof;
 b) SEQ ID NO.: 21 or an active portion thereof;
 c) SEQ ID NO.: 37 or an active portion thereof;
 d) DNA encoding DUB-1 enzyme having SEQ ID NO.: 2 or an active portion thereof;

e) DNA encoding DUB-3 enzyme having SEQ ID NO.: 9 or an active portion thereof;

f) DNA encoding DUB-2 enzyme having SEQ ID NO. 38 or an active portion thereof;

g) DNA encoding DUB-4 enzyme or an active portion thereof; and h) DNA encoding DUB-5 enzyme or an active portion thereof.

16. The DNA construct of claim 15 further comprising DNA encoding a second protein, wherein expression of the construct in a cell produces a fusion protein comprising the DUB enzyme and the second protein.

17. The DNA construct of claim 16 wherein the second protein is glutathione-S-transferase.

18. A method of reducing proliferation of an isolated mammalian cell, comprising inducing the expression of a DUB enzyme in said cell at a level sufficient to arrest growth of the cell.

19. A method of claim 18, wherein expression of the DUB enzyme is induced by IL-3, IL-5 and/or GM-CSF.

20. A method of claim 18, wherein the DUB enzyme has the amino acid sequence of SEQ ID NO.: 2.

21. A method of claim 18, wherein the isolated mammalian cell is a hematopoietic cell.

22. A method of reducing proliferation of an isolated mammalian cell, comprising introducing into the cell a nucleic acid construct comprising DNA encoding a DUB enzyme, under conditions suitable for inducing expression of the DUB enzyme at a level sufficient to arrest growth of the cell.

23. A method of claim 22 wherein expression of the DUB enzyme is under the control of an inducible promoter.

24. A method of claim 22, wherein expression of the DUB enzyme is induced by IL-3, IL-5 and/or GM-CSF.

25. A method of claim 22, wherein the nucleic acid construct comprises a nucleotide sequence selected from the group consisting of SEQ ID NO.: 1 and the nucleotide sequence which encodes DUB-1 enzyme of SEQ ID NO.: 2.

26. A method of identifying an agent which inhibits activity of a DUB enzyme, comprising the steps of:

a) introducing into a host cell:
1) a first nucleic acid construct encoding a fusion protein comprising the DUB enzyme and a second protein which is an enzyme; and
2) a second nucleic acid construct encoding a ubiquitin conjugated substrate of the second protein, thereby producing a host cell containing the first and second constructs;

b) maintaining the host cell produced in a) under conditions appropriate for expression of the fusion protein and the ubiquitin-conjugated substrate, thereby producing a host cell expressing the fusion protein and the ubiquitin-conjugated substrate;

c) combining the host cell expressing the fusion protein and the ubiquintin-conjugated substrate with an agent to be assessed; and d) determining the extent to which the enzyme in the fusion protein acts upon the ubiquitin-conjugated substrate, wherein if the DUB enzyne acts to a lesser extent on the ubiquitin-conjugated substrate in the presence of the agent than in the absence of the agent the agent is an inhibitor of the DUB enzyme.

27. A method of claim 26 wherein the DUB enzyme in the fusion protein cleaves the ubiquitin-conjugated substrate and the extent to which the DUB enzyme acts is assessed by determining the extent to which cleavage of the ubiquitin-conjugated substrate occurs.

28. An isolated DNA comprising the sequence consisting of the base pairs numbered −1528 to −1416 of SEQ ID NO.: 7, as represented in FIG. 4.

29. A method of producing a DUB enzyme comprising the step of culturing a host cell transfected with a nucleic acid encoding a DUB enzyme under conditions in which the nucleic acid is expressed, thereby producing the DUB enzyme.

30. The method of claim 29, wherein the nucleic acid encoding a DUB enzyme consists of a nucleic acid sequence selected from the group consisting of:

a) SEQ ID NO.: 1 or an active portion thereof;

b) SEQ ID NO.: 21 or an active portion thereof;

c) SEQ ID NO.: 37 or an active portion thereof;

d) DNA encoding DUB-1 enzyme of SEQ ID NO.: 2 or an active portion thereof;

e) DNA encoding DUB-3 enzyme of SEQ ID NO.: 9 or an active portion thereof;

f) DNA encoding DUB-2 enzyme of SEQ ID NO.: 38 or an active portion thereof;

g) DNA encoding DUB-4 enzyme or an active portion thereof; and h) DNA encoding DUB-5 enzyme or an active portion thereof.

31. The method of claim 29, wherein the nucleic acid encoding a DUB enzyme consists of a nucleotide sequences which hybridizes under stringency conditions of 0.1×SSC/0.1% SDS at room temperature to a nucleotide sequence encoding a DUB enzyme.

* * * * *

SEQUENCE LISTING

```
<160> NUMBER OF SEQ ID NOS:  51

<210> SEQ ID NO 1
<211> LENGTH: 2674
<212> TYPE: DNA
<213> ORGANISM: Murine
<220> FEATURE:
<221> NAME/KEY: CDS
<222> LOCATION: (184)...(1761)

<400> SEQUENCE: 1
gaattcggca cgaggaaaaa cttccttctg ctcccttaga agactccagc tagttatttg      60
aagaggtctt tgtagacacg gtggttgctc tttcctccca agaagagatt ctctagaagg     120
gaaaaacttc cttctgctcc cttagaagac tacagcaagt tctttgaaga ggtctttgga     180 gac atg gtg gtt gct ctt tcc ttc cca gaa gca gat cca gcc cta tca     228
    Met Val Val Ala Leu Ser Phe Pro Glu Ala Asp Pro Ala Leu Ser
```

-continued

|   | 1 |   |   | 5 |   |   |   | 10 |   |   |   | 15 |   |   |      |
|---|---|---|---|---|---|---|---|----|---|---|---|----|---|---|------|
| tct | cct | gat | gcc | cca | gag | ctg | cat | cag | gat | gaa | gct | cag | gtg | gtg | gag | 276 |
| Ser | Pro | Asp | Ala | Pro | Glu | Leu | His | Gln | Asp | Glu | Ala | Gln | Val | Val | Glu |
|     |     |     |     | 20  |     |     |     |     | 25  |     |     |     |     | 30  |     |

| gag | cta | act | gtc | aat | gga | aag | cac | agt | ctg | agt | tgg | gag | agt | ccc | caa | 324 |
| Glu | Leu | Thr | Val | Asn | Gly | Lys | His | Ser | Leu | Ser | Trp | Glu | Ser | Pro | Gln |
|     |     |     |     | 35  |     |     |     |     | 40  |     |     |     |     | 45  |     |

| gga | cca | gga | tgc | ggg | ctc | cag | aac | aca | ggc | aac | agc | tgc | tac | ctg | aat | 372 |
| Gly | Pro | Gly | Cys | Gly | Leu | Gln | Asn | Thr | Gly | Asn | Ser | Cys | Tyr | Leu | Asn |
|     |     |     | 50  |     |     |     |     | 55  |     |     |     |     | 60  |     |     |

| gca | gcc | ctg | cag | tgc | ttg | aca | cac | aca | cca | cct | cta | gct | gac | tac | atg | 420 |
| Ala | Ala | Leu | Gln | Cys | Leu | Thr | His | Thr | Pro | Pro | Leu | Ala | Asp | Tyr | Met |
|     | 65  |     |     |     |     | 70  |     |     |     |     | 75  |     |     |     |     |

| ctg | tcc | cag | gag | cac | agt | caa | acc | tgt | tgt | tcc | cca | gaa | ggc | tgt | aag | 468 |
| Leu | Ser | Gln | Glu | His | Ser | Gln | Thr | Cys | Cys | Ser | Pro | Glu | Gly | Cys | Lys |
| 80  |     |     |     |     | 85  |     |     |     |     | 90  |     |     |     |     | 95  |

| ttg | tgt | gct | atg | gaa | gcc | ctt | gtg | acc | cag | agt | ctc | ctg | cac | tct | cac | 516 |
| Leu | Cys | Ala | Met | Glu | Ala | Leu | Val | Thr | Gln | Ser | Leu | Leu | His | Ser | His |
|     |     |     |     | 100 |     |     |     |     | 105 |     |     |     |     | 110 |     |

| tcg | ggg | gat | gtc | atg | aag | ccc | tcc | cat | att | ttg | acc | tct | gcc | ttc | cac | 564 |
| Ser | Gly | Asp | Val | Met | Lys | Pro | Ser | His | Ile | Leu | Thr | Ser | Ala | Phe | His |
|     |     |     |     | 115 |     |     |     |     | 120 |     |     |     |     | 125 |     |

| aag | cac | cag | cag | gaa | gat | gcc | cac | gag | ttt | ctc | atg | ttc | acc | ttg | gaa | 612 |
| Lys | His | Gln | Gln | Glu | Asp | Ala | His | Glu | Phe | Leu | Met | Phe | Thr | Leu | Glu |
|     |     |     | 130 |     |     |     |     | 135 |     |     |     |     | 140 |     |     |

| aca | atg | cat | gaa | tcc | tgc | ctt | caa | gtg | cac | aga | caa | tca | aaa | ccc | acc | 660 |
| Thr | Met | His | Glu | Ser | Cys | Leu | Gln | Val | His | Arg | Gln | Ser | Lys | Pro | Thr |
|     | 145 |     |     |     |     | 150 |     |     |     |     | 155 |     |     |     |     |

| tct | gag | gac | agc | tca | ccc | att | cat | gac | ata | ttt | gga | ggc | tgg | tgg | agg | 708 |
| Ser | Glu | Asp | Ser | Ser | Pro | Ile | His | Asp | Ile | Phe | Gly | Gly | Trp | Trp | Arg |
| 160 |     |     |     |     | 165 |     |     |     |     | 170 |     |     |     |     | 175 |

| tct | cag | atc | aag | tgt | ctc | ctt | tgc | cag | ggt | acc | tca | gat | acc | tat | gat | 756 |
| Ser | Gln | Ile | Lys | Cys | Leu | Leu | Cys | Gln | Gly | Thr | Ser | Asp | Thr | Tyr | Asp |
|     |     |     |     | 180 |     |     |     |     | 185 |     |     |     |     | 190 |     |

| cgc | ttc | ctg | gac | atc | ccc | ctg | gat | atc | agc | tca | gct | cag | agt | gta | aag | 804 |
| Arg | Phe | Leu | Asp | Ile | Pro | Leu | Asp | Ile | Ser | Ser | Ala | Gln | Ser | Val | Lys |
|     |     |     | 195 |     |     |     |     | 200 |     |     |     |     | 205 |     |     |

| caa | gcc | ttg | tgg | gat | aca | gag | aag | tca | gaa | gag | cta | tgt | gga | gat | aat | 852 |
| Gln | Ala | Leu | Trp | Asp | Thr | Glu | Lys | Ser | Glu | Glu | Leu | Cys | Gly | Asp | Asn |
|     | 210 |     |     |     |     | 215 |     |     |     |     | 220 |     |     |     |     |

| gcc | tac | tac | tgt | ggt | aag | tgt | aga | cag | aag | atg | cca | gct | tct | aag | acc | 900 |
| Ala | Tyr | Tyr | Cys | Gly | Lys | Cys | Arg | Gln | Lys | Met | Pro | Ala | Ser | Lys | Thr |
|     | 225 |     |     |     |     | 230 |     |     |     |     | 235 |     |     |     |     |

| ctg | cat | gtt | cat | att | gct | cca | aag | gta | ctc | atg | gta | gtg | tta | aat | cgc | 948 |
| Leu | His | Val | His | Ile | Ala | Pro | Lys | Val | Leu | Met | Val | Val | Leu | Asn | Arg |
| 240 |     |     |     |     | 245 |     |     |     |     | 250 |     |     |     |     | 255 |

| ttc | tca | gcc | ttc | acg | ggt | aac | aag | tta | gac | aga | aaa | gta | agt | tac | ccg | 996 |
| Phe | Ser | Ala | Phe | Thr | Gly | Asn | Lys | Leu | Asp | Arg | Lys | Val | Ser | Tyr | Pro |
|     |     |     |     | 260 |     |     |     |     | 265 |     |     |     |     | 270 |     |

| gag | ttc | ctt | gac | ctg | aag | cca | tac | ctg | tct | gag | cct | act | gga | gga | cct | 1044 |
| Glu | Phe | Leu | Asp | Leu | Lys | Pro | Tyr | Leu | Ser | Glu | Pro | Thr | Gly | Gly | Pro |
|     |     |     | 275 |     |     |     |     | 280 |     |     |     |     | 285 |     |     |

| ttg | cct | tat | gcc | ctc | tat | gcc | gtc | ctg | gtc | cat | gat | ggt | gcg | act | tct | 1092 |
| Leu | Pro | Tyr | Ala | Leu | Tyr | Ala | Val | Leu | Val | His | Asp | Gly | Ala | Thr | Ser |
|     |     |     | 290 |     |     |     |     | 295 |     |     |     |     | 300 |     |     |

| cac | agt | gga | cat | tac | ttc | tgt | tgt | gtc | aaa | gct | ggt | cat | ggg | aag | tgg | 1140 |
| His | Ser | Gly | His | Tyr | Phe | Cys | Cys | Val | Lys | Ala | Gly | His | Gly | Lys | Trp |
|     |     |     |     | 305 |     |     |     |     | 310 |     |     |     |     | 315 |     |

| tac | aag | atg | gat | gat | act | aaa | gtc | acc | agg | tgt | gat | gtg | act | tct | gtc | 1188 |

-continued

```
Tyr Lys Met Asp Asp Thr Lys Val Thr Arg Cys Asp Val Thr Ser Val
320                 325                 330                 335 ctg aat gag aat gcc tat gtg ctc ttc tat gtg cag cag gcc aac ctc      1236
Leu Asn Glu Asn Ala Tyr Val Leu Phe Tyr Val Gln Gln Ala Asn Leu
                340                 345                 350 aaa cag gtc agt att gac atg cca gag gga aga ata aat gag gtt ctt      1284
Lys Gln Val Ser Ile Asp Met Pro Glu Gly Arg Ile Asn Glu Val Leu
            355                 360                 365 gac cct gaa tac cag ctg aag aaa tca cgg aga aaa aag cat aag aag      1332
Asp Pro Glu Tyr Gln Leu Lys Lys Ser Arg Arg Lys Lys His Lys Lys
        370                 375                 380 aaa agc cct ttc aca gaa gat tta gga gag ccc tgc gaa aac agg gat      1380
Lys Ser Pro Phe Thr Glu Asp Leu Gly Glu Pro Cys Glu Asn Arg Asp
    385                 390                 395 aag aga gca att aaa gaa acc tcc tta gga aag ggg aaa gtg ctt cag      1428
Lys Arg Ala Ile Lys Glu Thr Ser Leu Gly Lys Gly Lys Val Leu Gln
400                 405                 410                 415 gaa gtg aac cac aag aaa gct ggg cag aaa cac ggg aat acc aaa ctc      1476
Glu Val Asn His Lys Lys Ala Gly Gln Lys His Gly Asn Thr Lys Leu
                420                 425                 430 atg cct cag aaa cag aac cac cag aaa gct ggg cag aac ctc agg aat      1524
Met Pro Gln Lys Gln Asn His Gln Lys Ala Gly Gln Asn Leu Arg Asn
            435                 440                 445 act gaa gtt gaa ctt gat ctg cct gct gat gca att gtg att cac cag      1572
Thr Glu Val Glu Leu Asp Leu Pro Ala Asp Ala Ile Val Ile His Gln
        450                 455                 460 ccc aga tcc act gca aac tgg ggc agg gat tct cca gac aag gag aat      1620
Pro Arg Ser Thr Ala Asn Trp Gly Arg Asp Ser Pro Asp Lys Glu Asn
    465                 470                 475 caa ccc ttg cac aat gct gac agg ctc ctc acc tct cag ggc cct gtg      1668
Gln Pro Leu His Asn Ala Asp Arg Leu Leu Thr Ser Gln Gly Pro Val
480                 485                 490                 495 aac act tgg cag ctc tgt aga cag gaa ggg aga cga aga tcg aag aag      1716
Asn Thr Trp Gln Leu Cys Arg Gln Glu Gly Arg Arg Arg Ser Lys Lys
                500                 505                 510 ggg cag aac aag aac aag caa ggg cag agg ctt ctg ctt gtt tgc          1761
Gly Gln Asn Lys Asn Lys Gln Gly Gln Arg Leu Leu Leu Val Cys
            515                 520                 525 tagtgatcac ccaccactc acacaggctc ctgtggacac actgttgacc caaggtgcct    1821
ggaacaagag gtttggatct ctgtttcagg cagggacaat gcctcaccct tcacgtgggg    1881
tccacctatc ctctgggccc ttgcctgttt ttgctgactg actctctgat tgtttgaatg    1941
tggaaaaaaa gtgcccagga tgttggtaca ggttaaagac aagaagctgg acacccggag    2001
gaggtctgaa tagcctctcc tgcaactcat ggaatctgag cagcatagag actaaatcac    2061
cacactggag ctttcttttc ttttcttttc ttttcttttc ttttcttttc ttttcttttc    2121
tcttctcttc tcttctcttc tcttctcttc tcttctcttc tcttctcttc tcttctcttc    2181
tctcctctcc tctcctctcc tctcctctcc tctcctctcc tctcctttcc tttccttcc     2241 tttccttttt ttttaaattt atttttttgtt attagatatt ttctttattt acatttcaaa    2301
tgctatccca aaagttccct ataccctccc ccaactctgc caccctaccc acccactccc    2361
acttcttggc tctggcattt ccctgtactg gggcatataa agtttgcaat accaaagggc    2421
ctctcttccc aatgatggcc aactaggtca ccttctgcta catatgcagc tagagaccct    2481
aagaaaacac actggaactc ttgaggtttg gagttttcgc tcaggcaaac aagttgcttt    2541
tcaactgccc tttctaacct cttacccaga aaatgtgtag ttcaccctgt agagatagat    2601
```

-continued

```
gctcttattc ttagtgtgtg atcaacagtt ctttggtcaa ataaattctg ttacttcaca    2661
aaaaaaaaaa aaa                                                        2674
```

<210> SEQ ID NO 2
<211> LENGTH: 526
<212> TYPE: PRT
<213> ORGANISM: Murine

<400> SEQUENCE: 2

```
Met Val Val Ala Leu Ser Phe Pro Glu Ala Asp Pro Ala Leu Ser Ser
 1               5                  10                  15

Pro Asp Ala Pro Glu Leu His Gln Asp Glu Ala Gln Val Val Glu Glu
            20                  25                  30

Leu Thr Val Asn Gly Lys His Ser Leu Ser Trp Glu Ser Pro Gln Gly
        35                  40                  45

Pro Gly Cys Gly Leu Gln Asn Thr Gly Asn Ser Cys Tyr Leu Asn Ala
    50                  55                  60

Ala Leu Gln Cys Leu Thr His Thr Pro Pro Leu Ala Asp Tyr Met Leu
65                  70                  75                  80

Ser Gln Glu His Ser Gln Thr Cys Cys Ser Pro Glu Gly Cys Lys Leu
                85                  90                  95

Cys Ala Met Glu Ala Leu Val Thr Gln Ser Leu His Ser His Ser
            100                 105                 110

Gly Asp Val Met Lys Pro Ser His Ile Leu Thr Ser Ala Phe His Lys
        115                 120                 125

His Gln Gln Glu Asp Ala His Glu Phe Leu Met Phe Thr Leu Glu Thr
    130                 135                 140

Met His Glu Ser Cys Leu Gln Val His Arg Gln Ser Lys Pro Thr Ser
145                 150                 155                 160

Glu Asp Ser Ser Pro Ile His Asp Ile Phe Gly Gly Trp Trp Arg Ser
                165                 170                 175

Gln Ile Lys Cys Leu Leu Cys Gln Gly Thr Ser Asp Thr Tyr Asp Arg
            180                 185                 190

Phe Leu Asp Ile Pro Leu Asp Ile Ser Ser Ala Gln Ser Val Lys Gln
        195                 200                 205

Ala Leu Trp Asp Thr Glu Lys Ser Glu Glu Leu Cys Gly Asp Asn Ala
    210                 215                 220

Tyr Tyr Cys Gly Lys Cys Arg Gln Lys Met Pro Ala Ser Lys Thr Leu
225                 230                 235                 240

His Val His Ile Ala Pro Lys Val Leu Met Val Val Leu Asn Arg Phe
                245                 250                 255

Ser Ala Phe Thr Gly Asn Lys Leu Asp Arg Lys Val Ser Tyr Pro Glu
            260                 265                 270

Phe Leu Asp Leu Lys Pro Tyr Leu Ser Glu Pro Thr Gly Gly Pro Leu
        275                 280                 285

Pro Tyr Ala Leu Tyr Ala Val Leu Val His Asp Gly Ala Thr Ser His
    290                 295                 300

Ser Gly His Tyr Phe Cys Cys Val Lys Ala Gly His Gly Lys Trp Tyr
305                 310                 315                 320

Lys Met Asp Asp Thr Lys Val Thr Arg Cys Asp Val Thr Ser Val Leu
                325                 330                 335

Asn Glu Asn Ala Tyr Val Leu Phe Tyr Val Gln Gln Ala Asn Leu Lys
            340                 345                 350

Gln Val Ser Ile Asp Met Pro Glu Gly Arg Ile Asn Glu Val Leu Asp
```

-continued

```
                355                 360                 365
Pro Glu Tyr Gln Leu Lys Lys Ser Arg Arg Lys Lys His Lys Lys Lys
            370                 375                 380
Ser Pro Phe Thr Glu Asp Leu Gly Glu Pro Cys Glu Asn Arg Asp Lys
385                 390                 395                 400
Arg Ala Ile Lys Glu Thr Ser Leu Gly Lys Gly Lys Val Leu Gln Glu
                405                 410                 415
Val Asn His Lys Lys Ala Gly Gln Lys His Gly Asn Thr Lys Leu Met
            420                 425                 430
Pro Gln Lys Gln Asn His Gln Lys Ala Gly Gln Asn Leu Arg Asn Thr
            435                 440                 445
Glu Val Glu Leu Asp Leu Pro Ala Asp Ala Ile Val Ile His Gln Pro
450                 455                 460
Arg Ser Thr Ala Asn Trp Gly Arg Asp Ser Pro Asp Lys Glu Asn Gln
465                 470                 475                 480
Pro Leu His Asn Ala Asp Arg Leu Leu Thr Ser Gln Gly Pro Val Asn
                485                 490                 495
Thr Trp Gln Leu Cys Arg Gln Gly Arg Arg Arg Ser Lys Lys Gly
            500                 505                 510
Gln Asn Lys Asn Lys Gln Gly Gln Arg Leu Leu Leu Val Cys
            515                 520                 525
```

<210> SEQ ID NO 3
<211> LENGTH: 18
<212> TYPE: PRT
<213> ORGANISM: Yeast

<400> SEQUENCE: 3

```
Gly Leu Glu Asn Leu Gly Asn Ser Cys Tyr Met Asn Cys Ile Ile Gln
1               5                   10                  15
Cys Ile
```

<210> SEQ ID NO 4
<211> LENGTH: 18
<212> TYPE: PRT
<213> ORGANISM: Homo sapiens

<400> SEQUENCE: 4

```
Gly Leu Ser Asn Leu Gly Asn Thr Cys Phe Met Asn Ser Ser Ile Gln
1               5                   10                  15
Cys Val
```

<210> SEQ ID NO 5
<211> LENGTH: 18
<212> TYPE: PRT
<213> ORGANISM: Murine

<400> SEQUENCE: 5

```
Gly Leu Gln Asn Thr Gly Asn Ser Cys Tyr Leu Asn Ala Ala Leu Gln
1               5                   10                  15
Cys Leu
```

<210> SEQ ID NO 6
<211> LENGTH: 28
<212> TYPE: PRT
<213> ORGANISM: Homo sapiens

<400> SEQUENCE: 6

Pro Ser Thr Arg Lys Asp Tyr Pro Ala Ala Lys Arg Ala Lys Leu Asp
1               5                   10                  15

Ser Gly Arg Val Leu Lys Gln Ile Ser Asn Asn Arg
            20                  25

<210> SEQ ID NO 7
<211> LENGTH: 1559
<212> TYPE: DNA
<213> ORGANISM: Murine

<400> SEQUENCE: 7

| | | | | | |
|---|---|---|---|---|---|
| actagtaagg | atataacagg | aaataatgac | taagactgtg | gtatgaaggt | aattcactga | 60 |
| tagtagaaat | ggaaaaaaaa | gtatcaggtt | tcactgcttc | ataaggagat | acaacagtga | 120 |
| ctaagaccgg | tttttctaaa | catgtgtggt | tatttgtttg | agtgtctgtg | tgtgtgtttg | 180 |
| attcttttct | tttcttttct | tttcttttct | tttcttttct | tttcttttct | tgaggtaatg | 240 |
| aaagccaatg | gtcatgagtt | gaagcgataa | tagggtgatt | gataacaagc | tcaaggtcag | 300 |
| tatggcgaag | gagccatatt | gtctcaaaaa | catacaagaa | gggaggattt | gcctgctttg | 360 |
| gtccacctag | agtgagtctt | attactgaag | taaggctgaa | tgagcataat | ggagctaatt | 420 |
| gggtgattga | atcatctact | cagcagttac | aactttagag | gcaatggcac | tataaaaatg | 480 |
| ttttttgttt | tgttttgttt | ttcccagata | gggttttgct | gtgtagccct | ggctgtcttg | 540 |
| gacctcactc | tgtagaccag | ggtagcctcc | aactgagaaa | ctgccctgca | tctgcctccc | 600 |
| aagtgctggg | atcacaaggt | tgcataacaa | ctgcctgcaa | aaattttgta | caagtaatta | 660 |
| gagagttagt | tgtgggtaaa | acacatcaaa | atgctttgca | ttcttgagtg | ctgataatac | 720 |
| actaaagaag | cagagtatag | attcaaggtc | atttttttt | ttttttttta | gagaatcaac | 780 |
| agtctactta | ctggactaga | tgtcttcata | gaccatatga | ctttgactgg | aaatgtgtct | 840 |
| tctacagaga | aagtggagag | agagagagaa | aaagaaggaa | ggaaggaagg | aaggaaggaa | 900 |
| ggaaggacgg | aaggaaggaa | gagagagaga | tagagagaga | gagagacaga | gaaagagaga | 960 |
| gagagagaga | taaagaaaga | aaggaaggaa | ggaaggaagg | aaggacggac | ggaaggaagg | 1020 |
| aagagagaga | gatagagaga | agagaagaga | aagagagaga | gagagataaa | gaaaggaagg | 1080 |
| aaggaaggaa | ggaaggaagg | aaggaaggaa | ggaaggaagg | aaggaagaaa | gaaagggcaa | 1140 |
| aagggaagga | aaaccaggcc | taggctgttt | atactggttc | tgtgtggtta | gcaaggtaat | 1200 |
| gggaactctt | gtatggcatg | tatagtcatc | tatttgacat | aattttgtaa | ctttattcca | 1260 |
| aataaaaccc | aaacttaaga | cacctaggaa | attggagcta | aattcaggga | aatgcactcc | 1320 |
| aaagagatga | catttctgag | ctgctttgca | gaaaccacac | ccaacttgtg | agaggcttgt | 1380 |
| ctgggattgg | ctgtcctggg | aagactgtag | gcgtggtcac | aagactggag | tttaaaagac | 1440 |
| tgagcatttg | tcctcacttg | cacagattct | ctagaaggga | aaaacttcct | tctgctccct | 1500 |
| tagaagacta | cagcaagttc | tttgaagagg | tctttggaga | catggtggtt | gctctttcc | 1559 |

<210> SEQ ID NO 8
<211> LENGTH: 508
<212> TYPE: PRT
<213> ORGANISM: Murine

<400> SEQUENCE: 8

Pro Ala Leu Ser Ser Pro Asp Ala Pro Glu Leu His Gln Asp Glu Ala
1               5                   10                  15

Gln Val Val Glu Glu Leu Thr Val Asn Gly Lys His Ser Leu Ser Trp
            20                  25                  30

```
Glu Ser Pro Gln Gly Pro Gly Cys Gly Leu Gln Asn Thr Gly Asn Ser
         35                  40                  45
Cys Tyr Leu Asn Ala Ala Leu Gln Cys Leu Thr His Thr Pro Pro Leu
 50                  55                  60
Ala Asp Tyr Met Leu Ser Gln Glu His Ser Gln Thr Cys Cys Ser Pro
 65                  70                  75                  80
Glu Gly Cys Lys Leu Cys Ala Met Glu Ala Leu Val Thr Gln Ser Leu
                 85                  90                  95
Leu His Ser His Ser Gly Asp Val Met Lys Pro Ser His Ile Leu Thr
                100                 105                 110
Ser Ala Phe His Lys His Gln Gln Glu Asp Ala His Glu Phe Leu Met
                115                 120                 125
Phe Thr Leu Glu Thr Met His Glu Ser Cys Leu Gln Val His Arg Gln
        130                 135                 140
Ser Lys Pro Thr Ser Glu Asp Ser Ser Pro Ile His Asp Ile Phe Gly
145                 150                 155                 160
Gly Trp Trp Arg Ser Gln Ile Lys Cys Leu Leu Cys Gln Gly Thr Ser
                165                 170                 175
Asp Thr Tyr Asp Arg Phe Leu Asp Ile Pro Leu Asp Ile Ser Ser Ala
                180                 185                 190
Gln Ser Val Lys Gln Ala Leu Trp Asp Thr Glu Lys Ser Glu Glu Leu
        195                 200                 205
Cys Gly Asp Asn Ala Tyr Tyr Cys Gly Lys Cys Arg Gln Lys Met Pro
        210                 215                 220
Ala Ser Lys Thr Leu His Val His Ile Ala Pro Lys Val Leu Met Val
225                 230                 235                 240
Val Leu Asn Arg Phe Ser Ala Phe Thr Gly Asn Lys Leu Asp Arg Lys
                245                 250                 255
Val Ser Tyr Pro Glu Phe Leu Asp Leu Lys Pro Tyr Leu Ser Glu Pro
                260                 265                 270
Thr Gly Gly Pro Leu Pro Tyr Ala Leu Tyr Ala Val Leu Val His Asp
        275                 280                 285
Gly Ala Thr Ser His Ser Gly His Tyr Phe Cys Cys Val Lys Ala Gly
        290                 295                 300
His Gly Lys Trp Tyr Lys Met Asp Asp Thr Lys Val Thr Arg Cys Asp
305                 310                 315                 320
Val Thr Ser Val Leu Asn Glu Asn Ala Tyr Val Leu Glu Tyr Val Gln
                325                 330                 335
Gln Ala Asn Leu Lys Gln Val Ser Ile Asp Met Pro Glu Gly Arg Ile
                340                 345                 350
Asn Glu Val Leu Asp Pro Glu Tyr Gln Leu Lys Lys Ser Arg Arg Lys
        355                 360                 365
Lys His Lys Lys Lys Ser Pro Phe Thr Glu Asp Leu Gly Glu Pro Cys
        370                 375                 380
Glu Asn Arg Asp Lys Arg Ala Ile Lys Glu Thr Ser Leu Gly Lys Gly
385                 390                 395                 400
Lys Val Leu Gln Glu Val Asn His Lys Lys Ala Gly Gln Lys His Gly
                405                 410                 415
Asn Thr Lys Leu Met Pro Gln Lys Gln Asn His Gln Lys Ala Gly Gln
                420                 425                 430
Asn Leu Arg Asn Thr Glu Val Glu Leu Asp Leu Pro Ala Asp Ala Ile
        435                 440                 445
```

-continued

Val Ile His Gln Pro Arg Ser Thr Ala Asn Trp Gly Arg Asp Ser Pro
    450                 455                 460

Asp Lys Glu Asn Gln Pro Leu His Asn Ala Asp Arg Leu Leu Thr Ser
465                 470                 475                 480

Gln Gly Pro Val Asn Thr Trp Gln Leu Cys Arg Gln Glu Gly Arg Arg
                    485                 490                 495

Arg Ser Lys Lys Gly Gln Asn Lys Asn Lys Gln Gly
            500                 505

<210> SEQ ID NO 9
<211> LENGTH: 509
<212> TYPE: PRT
<213> ORGANISM: Murine
<220> FEATURE:
<221> NAME/KEY: VARIANT
<222> LOCATION: (1)...(509)
<221> NAME/KEY: VARIANT
<222> LOCATION: (1)...(509)
<223> OTHER INFORMATION: Xaa = Any Amino Acid

<400> SEQUENCE: 9

Pro Ala Leu Ser Ser Pro Asp Ala Pro Glu Leu His Gln Phe Glu Ala
  1               5                  10                  15

Gln Val Glu Val Leu Thr Thr Asn Gly Lys Phe Ser Leu Ser Trp
                 20                  25                  30

Glu Ser Pro Xaa Gly Pro Gly Cys Gly Leu Gln Asn Thr Gly Asn Ser
                 35                  40                  45

Cys Tyr Leu Asn Ala Ala Leu Gln Cys Leu Thr His Thr Pro Pro Leu
 50                  55                  60

Ala Asp Tyr Met Leu Ser Gln Glu His Ser Gln Thr Cys Cys Ser Pro
65                  70                  75                  80

Glu Gly Cys Lys Met Cys Ala Met Glu Glu Cys Val Thr Gln Ser Leu
                 85                  90                  95

Xaa Leu Ser Leu Xaa Gly Asp Val Met Lys Pro Ser Gln Ile Leu Thr
                100                 105                 110

Ser Ala Phe His Lys His Gln Gln Glu Asp Ala His Glu Phe Leu Met
            115                 120                 125

Phe Thr Leu Glu Thr Met His Glu Ser Cys Leu Gln Val His Arg Gln
130                 135                 140

Ser Asp Pro Thr Pro Gln Asp Thr Ser Pro Ile His Asp Ile Phe Gly
145                 150                 155                 160

Gly Trp Trp Arg Ser Gln Ile Lys Cys Leu Xaa Ala Gly Thr Ser His
                165                 170                 175

Thr Phe Asp Pro Phe Leu Asp Val Pro Leu Asp Ile Ser Ser Ala Gln
            180                 185                 190

Ser Val Asn Gln Ala Leu Trp Asp Thr Gly Lys Ser Glu Glu Leu Leu
            195                 200                 205

Gly Glu Asn Ala Tyr Tyr Cys Gly Arg Cys Arg Gln Lys Met Pro Ala
210                 215                 220

Ser Lys Thr Leu His Val His Ile Ala Pro Lys Val Leu Leu Leu Val
225                 230                 235                 240

Leu Lys Arg Phe Ser Ala Phe Thr Gly Asn Lys Leu Asp Arg Lys Val
                245                 250                 255

Ser Tyr Pro Glu Phe Leu Asp Leu Lys Pro Tyr Leu Ser Glu Pro Thr
            260                 265                 270

Gly Gly Pro Leu Pro Tyr Ala Leu Tyr Ala Val Leu Val His Asp Gly
        275                 280                 285

```
Ala Thr Ser Asn Ser Gly His Tyr Phe Cys Cys Val Lys Ala Gly His
    290                 295                 300

Gly Lys Trp Tyr Lys Met Asp Asp Thr Lys Val Thr Arg Cys Asp Val
305                 310                 315                 320

Thr Ser Val Leu Asn Glu Asn Ala Tyr Val Leu Phe Tyr Val Gln Gln
                325                 330                 335

Ala Asp Leu Lys Gln Val Ser Ile Asp Met Pro Glu Gly Arg Val His
                340                 345                 350

Glu Val Leu Asp Pro Lys Tyr Gln Leu Lys Ser Arg Arg Lys Lys
            355                 360                 365

His Lys Met Gln Cys His Cys Ser Phe Gly Ala Gly Glu Gly Thr Arg
    370                 375                 380

Glu Lys Asp Gly Arg Arg Glu Gln Arg Asn Leu Leu Arg Glu Gly Ser
385                 390                 395                 400

Ala Xaa Ser Glu Val Asn His Glu Lys Ala Gly Ser Glu His Gly Asn
                405                 410                 415

Thr Lys Leu Val Pro Gln Glu Gln Asn His Gln Arg Ala Gly Gln Asn
            420                 425                 430

Leu Arg Asn Thr Glu Val Glu Leu Asp Leu Pro Val Asp Val Ile Val
            435                 440                 445

Ile His Gln Pro Arg Ser Thr Ala Asn Trp Gly Xaa Gly Cys Ser Ser
    450                 455                 460

Ile Lys Glu Asn Gln Pro Trp Xaa Thr Asn Gly Asp Arg Phe Leu Thr
465                 470                 475                 480

Ser Gln Gly Leu Met Ser Pro Gly Gln Leu Cys Ser Gln Gly Gly Arg
                485                 490                 495

Xaa Arg Ser Lys Lys Gly Lys Asn Lys Tyr Lys Gln Gly
            500                 505

<210> SEQ ID NO 10
<211> LENGTH: 418
<212> TYPE: PRT
<213> ORGANISM: Artificial Sequence
<220> FEATURE:
<223> OTHER INFORMATION: consensus

<400> SEQUENCE: 10

Pro Ala Leu Ser Ser Pro Asp Ala Pro Glu Leu His Gln Glu Ala Gln
1               5                   10                  15

Val Val Glu Leu Thr Asn Gly Lys Ser Leu Ser Trp Glu Ser Pro Gly
                20                  25                  30

Pro Gly Cys Gly Leu Gln Asn Thr Gly Asn Ser Cys Tyr Leu Asn Ala
            35                  40                  45

Ala Leu Gln Cys Leu Thr His Thr Pro Leu Ala Asp Tyr Met Leu
    50                  55                  60

Ser Gln Glu His Ser Gln Thr Cys Cys Ser Pro Glu Gly Cys Lys Cys
65                  70                  75                  80

Ala Met Glu Val Thr Gln Ser Leu Ser Gly Asp Val Met Lys Pro Ser
                85                  90                  95

Ile Leu Thr Ser Ala Phe His Lys His Gln Gln Glu Asp Ala His Glu
            100                 105                 110

Phe Leu Met Phe Thr Leu Glu Thr Met His Glu Ser Cys Leu Gln Val
            115                 120                 125

His Arg Gln Ser Pro Thr Asp Ser Pro Ile His Asp Ile Phe Gly Gly
    130                 135                 140
```

```
Trp Trp Arg Ser Gln Ile Lys Cys Leu Gly Thr Ser Thr Asp Phe Leu
145                 150                 155                 160

Asp Pro Leu Asp Ile Ser Ser Ala Gln Ser Val Gln Ala Leu Trp Asp
            165                 170                 175

Thr Lys Ser Glu Glu Leu Gly Asn Ala Tyr Tyr Cys Gly Cys Arg Gln
        180                 185                 190

Lys Met Pro Ala Ser Lys Thr Leu His Val His Ile Ala Pro Lys Val
    195                 200                 205

Leu Val Leu Arg Phe Ser Ala Phe Thr Gly Asn Lys Leu Asp Arg Lys
210                 215                 220

Val Ser Tyr Pro Glu Phe Leu Asp Leu Lys Pro Tyr Leu Ser Glu Pro
225                 230                 235                 240

Thr Gly Gly Pro Leu Pro Tyr Ala Leu Tyr Ala Val Leu Val His Asp
                245                 250                 255

Gly Ala Thr Ser Ser Gly His Tyr Phe Cys Val Lys Ala Gly His
            260                 265                 270

Gly Lys Trp Tyr Lys Met Asp Asp Thr Lys Val Thr Arg Cys Asp Val
        275                 280                 285

Thr Ser Val Leu Asn Glu Asn Ala Tyr Val Leu Phe Tyr Val Gln Gln
    290                 295                 300

Ala Leu Lys Gln Val Ser Ile Asp Met Pro Glu Gly Arg Glu Val Leu
305                 310                 315                 320

Asp Pro Tyr Gln Leu Lys Lys Ser Arg Arg Lys Lys His Lys Gly Glu
                325                 330                 335

Asp Arg Leu Gly Glu Val Asn His Lys Ala Gly His Gly Asn Thr Lys
            340                 345                 350

Leu Pro Gln Gln Asn His Gln Ala Gly Gln Asn Leu Arg Asn Thr Glu
        355                 360                 365

Val Glu Leu Asp Leu Pro Asp Ile Val Ile His Gln Pro Arg Ser Thr
    370                 375                 380

Ala Asn Trp Gly Ser Lys Glu Asn Gln Pro Asn Asp Arg Leu Thr Ser
385                 390                 395                 400

Gln Gly Gln Leu Cys Gln Gly Arg Arg Ser Lys Lys Gly Asn Lys Lys
                405                 410                 415

Gln Gly

<210> SEQ ID NO 11
<211> LENGTH: 18
<212> TYPE: PRT
<213> ORGANISM: Murine

<400> SEQUENCE: 11

Gly Leu Gln Asn Thr Gly Asn Ser Cys Tyr Leu Asn Ala Ala Leu Gln
1               5                   10                  15

Cys Leu

<210> SEQ ID NO 12
<211> LENGTH: 18
<212> TYPE: PRT
<213> ORGANISM: Murine

<400> SEQUENCE: 12

Gly Leu Gln Asn Thr Gly Asn Ser Cys Tyr Leu Asn Ala Ala Leu Gln
1               5                   10                  15

Cys Leu
```

<210> SEQ ID NO 13
<211> LENGTH: 18
<212> TYPE: PRT
<213> ORGANISM: Murine

<400> SEQUENCE: 13

Gly Leu Gln Asn Thr Gly Asn Ser Cys Tyr Leu Asn Ala Ala Leu Gln
 1               5                  10                  15

Cys Leu

<210> SEQ ID NO 14
<211> LENGTH: 18
<212> TYPE: PRT
<213> ORGANISM: Murine

<400> SEQUENCE: 14

Gly Leu Gln Asn Thr Gly Asn Ser Cys Tyr Leu Asn Ala Ala Leu Gln
 1               5                  10                  15

Cys Leu

<210> SEQ ID NO 15
<211> LENGTH: 56
<212> TYPE: PRT
<213> ORGANISM: Murine

<400> SEQUENCE: 15

Tyr Ala Leu Tyr Ala Val Leu Val His Asp Gly Ala Thr Ser His Ser
 1               5                  10                  15

Gly His Tyr Phe Cys Cys Val Lys Ala Gly His Gly Lys Trp Tyr Lys
             20                  25                  30

Met Asp Asp Thr Lys Val Thr Arg Cys Asp Val Thr Ser Val Leu Asn
         35                  40                  45

Glu Asn Ala Tyr Val Leu Phe Tyr
     50                  55

<210> SEQ ID NO 16
<211> LENGTH: 56
<212> TYPE: PRT
<213> ORGANISM: Murine

<400> SEQUENCE: 16

Tyr Ala Leu Tyr Ala Val Leu Val His Asp Gly Ala Thr Ser Asn Ser
 1               5                  10                  15

Gly His Tyr Phe Cys Cys Val Lys Ala Gly His Gly Lys Trp Tyr Lys
             20                  25                  30

Met Asp Asp Thr Lys Val Thr Arg Cys Asp Val Thr Ser Val Leu Asn
         35                  40                  45

Glu Asn Ala Tyr Val Leu Phe Tyr
     50                  55

<210> SEQ ID NO 17
<211> LENGTH: 97
<212> TYPE: PRT
<213> ORGANISM: Murine
<220> FEATURE:
<221> NAME/KEY: VARIANT
<222> LOCATION: (1)...(97)
<221> NAME/KEY: VARIANT
<222> LOCATION: (1)...(97)
<223> OTHER INFORMATION: Xaa = Any Amino Acid -continued

<400> SEQUENCE: 17

Lys Leu Xaa Pro Gln Glu Gln Asn His Gln Lys Ala Gly Gln Asn Leu
1               5                   10                  15

Arg Asn Thr Glu Val Glu Leu Asp Leu Pro Ala Asp Ala Ile Val Ile
            20                  25                  30

His Gln Pro Arg Ser Thr Ala Asn Trp Gly Arg Asp Ala Pro Asp Lys
        35                  40                  45

Glu Asn Gln Pro Trp His Asn Ala Asp Arg Leu Leu Thr Ser Gln Gly
    50                  55                  60

Pro Val Asn Thr Gly Gln Leu Cys Arg Gln Glu Gly Arg Arg Arg Ser
65                  70                  75                  80

Lys Lys Gly Xaa Asn Lys Asn Lys Gln Gly Gln Arg Leu Leu Leu Val
                85                  90                  95

Cys

<210> SEQ ID NO 18
<211> LENGTH: 97
<212> TYPE: PRT
<213> ORGANISM: Murine

<400> SEQUENCE: 18

Lys Leu Met Pro Gln Lys Gln Asn His Gln Lys Ala Gly Gln Asn Leu
1               5                   10                  15

Arg Asn Thr Glu Val Glu Leu Asp Leu Pro Ala Asp Ala Ile Val Ile
            20                  25                  30

His Gln Pro Arg Ser Thr Ala Asn Trp Gly Arg Asp Ser Pro Asp Lys
        35                  40                  45

Glu Asn Gln Pro Leu His Asn Ala Asp Arg Leu Leu Thr Ser Gln Gly
    50                  55                  60

Pro Val Asn Thr Trp Gln Leu Cys Arg Gln Glu Gly Arg Arg Arg Ser
65                  70                  75                  80

Lys Lys Gly Gln Asn Lys Asn Lys Gln Gly Gln Arg Leu Leu Leu Val
                85                  90                  95

Cys

<210> SEQ ID NO 19
<211> LENGTH: 97
<212> TYPE: PRT
<213> ORGANISM: Murine

<400> SEQUENCE: 19

Lys Leu Leu Pro Gln Glu Gln Asn His Gln Lys Ala Gly Gln Ser Leu
1               5                   10                  15

Arg Asn Thr Glu Gly Glu Leu Asp Leu Pro Ala Asp Ala Ile Val Ile
            20                  25                  30

His Gln Leu Arg Ser Thr Glu Asn Trp Gly Arg Asp Ala Pro Asp Lys
        35                  40                  45

Glu Asn Gln Pro Trp His Asn Ala Asp Arg Leu Leu Thr Ser Gln Asp
    50                  55                  60

Pro Val Asn Thr Gly Gln Leu Cys Arg Gln Glu Gly Arg Arg Arg Ser
65                  70                  75                  80

Lys Lys Gly Lys Asn Lys Asn Lys Gln Gly Gln Arg Leu Leu Leu Val
                85                  90                  95

Cys

<210> SEQ ID NO 20
<211> LENGTH: 97
<212> TYPE: PRT
<213> ORGANISM: Murine
<220> FEATURE:
<221> NAME/KEY: VARIANT
<222> LOCATION: (1)...(97)
<221> NAME/KEY: VARIANT
<222> LOCATION: (1)...(97)
<223> OTHER INFORMATION: Xaa = Any Amino Acid

<400> SEQUENCE: 20

Lys Leu Val Pro Gln Glu Gln Asn His Gln Arg Ala Gly Gln Asn Leu
 1               5                  10                  15

Arg Asn Thr Glu Val Glu Leu Asp Leu Pro Val Asp Ala Ile Val Ile
            20                  25                  30

His Gln Pro Arg Ser Thr Ala Asn Trp Gly Thr Asp Ala Pro Asp Lys
        35                  40                  45

Glu Asn Gln Pro Trp His Asn Gly Asp Arg Leu Leu Thr Ser Gln Gly
    50                  55                  60

Leu Met Ser Pro Gly Gln Leu Cys Ser Gln Gly Gly Arg Xaa Arg Ser
65                  70                  75                  80

Lys Lys Gly Lys Asn Lys Asn Lys Gln Gly Gln Arg Leu Leu Leu Val
                85                  90                  95

Cys

<210> SEQ ID NO 21
<211> LENGTH: 1523
<212> TYPE: DNA
<213> ORGANISM: murine
<220> FEATURE:
<221> NAME/KEY: misc_feature
<222> LOCATION: (1)...(1523)
<223> OTHER INFORMATION: n = A,T,C or G

<400> SEQUENCE: 21
ccagcactat catctcctga tgccccagag ctgcatcagt ttgaagctca ggtggtggag      60
gtgctaacta ccaatggaaa gttcagtctg agttgggaga gtccctaagg accaggatgc     120
gggctccaga acacaggcaa cagctgctac ctgaacgcag ccctgcagtg cttgacacac     180
acaccacctc tagctgacta catgctgtcc caggagcaca gtcaaacctg ttgttcccca     240
gaaggttgta agatgtgtgc tatggaagaa tgtgtgaccc agagtctttg actctcactg     300
ggggatgtca tgaagccctc ccagattttg acctctgcct tccacaagca ccagcaggaa     360
gatgcccatg agtttctcat gttcaccttg gaaacaatgc atgaatcctg ccttcaagtg     420
cacagacaat cagatcccac ccctcaggat acgtcaccca ttcatgacat atttggaggc     480
tggtggaggt ctcagatcaa gtgtctcnat gcaggcacct cacataccct cgatcccttc     540
ctggatgtcc cctggatat cagctcagct cagagtgtaa atcaagcctt gtgggataca      600
gggaagtcag aagagctact tggagagaat gcctactact gtggtaggtg tagacagaag     660
atgccagctt ctaagaccct gcatgttcat attgctccaa aggtactcct gctagtgtta     720
aagcgcttct cagccttcac gggtaacaag ttagacagaa aagtaagcta cccggagttc     780
cttgacctga agccataccct gtctgagcct actggaggac ctttgcctta tgccctctat     840
gccgtcctgg tccatgatgg tgcgacttct aacagtggac attacttctg ttgtgtcaaa     900
gctggtcatg ggaagtggta caagatggat gatactaagg tcaccaggtg tgatgtgact     960
tctgtcctga atgagaatgc ctatgtgctc ttctatgtgc agcaggccga cctcaaacag    1020

-continued

```
gtcagtattg acatgccaga gggcagagta catgaggttc ttgaccctaa ataccagctg      1080
aagaaatccc ggagaaaaaa gcataagatg caatgccatt gctcatttgg tgcgggagaa      1140
ggcactcgcg aaaagatgg aagaagagag caaagaaacc tccttaggga gggaagtgcc       1200
tcagaagtga accacgagaa agctgggtca gaacatggga ataccaaact cgtgcctcag      1260
gaacagaacc accagagagc tggcagaac ctcaggaata ctgaagttga acttgatctg       1320
cctgttgatg tcattgtgat tcaccagccc agatccacag caaactgggg cnacggatgc      1380
tccagtatca aagagaatca accctggntc acnaatggtg acaggttcct cacctctcag     1440
ggcctcatga gccctgggca gctctgtagt cagggtggga gatgaagatc gaagaagggg      1500
aagaacaagt acaagcaagg gca                                              1523
```

<210> SEQ ID NO 22
<211> LENGTH: 521
<212> TYPE: PRT
<213> ORGANISM: Murine

<400> SEQUENCE: 22

```
Ser Phe Pro Glu Ala Asp Pro Ala Leu Ser Ser Pro Asp Ala Pro Glu
 1               5                  10                  15

Leu His Gln Asp Glu Ala Gln Val Val Glu Leu Thr Val Asn Gly
             20                  25                  30

Lys His Ser Leu Ser Trp Glu Ser Pro Gln Gly Pro Gly Cys Gly Leu
         35                  40                  45

Gln Asn Thr Gly Asn Ser Cys Tyr Leu Asn Ala Ala Leu Gln Cys Leu
     50                  55                  60

Thr His Thr Pro Pro Leu Ala Asp Tyr Met Leu Ser Gln Glu His Ser
 65                  70                  75                  80

Gln Thr Cys Cys Ser Pro Glu Gly Cys Lys Leu Cys Ala Met Glu Ala
                 85                  90                  95

Leu Val Thr Gln Ser Leu Leu His Ser His Ser Gly Asp Val Met Lys
            100                 105                 110

Pro Ser His Ile Leu Thr Ser Ala Phe His Lys His Gln Gln Glu Asp
        115                 120                 125

Ala His Glu Phe Leu Met Phe Thr Leu Glu Thr Met His Glu Ser Cys
    130                 135                 140

Leu Gln Val His Arg Gln Ser Lys Pro Thr Ser Glu Asp Ser Ser Pro
145                 150                 155                 160

Ile His Asp Ile Phe Gly Gly Trp Trp Arg Ser Gln Ile Lys Cys Leu
                165                 170                 175

Leu Cys Gln Gly Thr Ser Asp Thr Tyr Asp Arg Phe Leu Asp Ile Pro
            180                 185                 190

Leu Asp Ile Ser Ser Ala Gln Ser Val Lys Gln Ala Leu Trp Asp Thr
        195                 200                 205

Glu Lys Ser Glu Glu Leu Cys Gly Asp Asn Ala Tyr Tyr Cys Gly Lys
    210                 215                 220

Cys Arg Gln Lys Met Pro Ala Ser Lys Thr Leu His Val His Ile Ala
225                 230                 235                 240

Pro Lys Val Leu Met Val Val Leu Asn Arg Phe Ser Ala Phe Thr Gly
                245                 250                 255

Asn Lys Leu Asp Arg Lys Val Ser Tyr Pro Glu Phe Leu Asp Leu Lys
            260                 265                 270

Pro Tyr Leu Ser Glu Pro Thr Gly Gly Pro Leu Pro Tyr Ala Leu Tyr
        275                 280                 285
```

```
Ala Val Leu Val His Asp Gly Ala Thr Ser His Ser Gly His Tyr Phe
    290                 295                 300

Cys Cys Val Lys Ala Gly His Gly Lys Trp Tyr Lys Met Asp Asp Thr
305                 310                 315                 320

Lys Val Thr Arg Cys Asp Val Thr Ser Val Leu Asn Glu Asn Ala Tyr
            325                 330                 335

Val Leu Phe Tyr Val Gln Gln Ala Asn Leu Lys Gln Val Ser Ile Asp
            340                 345                 350

Met Pro Glu Gly Arg Ile Asn Glu Val Leu Asp Pro Glu Tyr Gln Leu
        355                 360                 365

Lys Lys Ser Arg Arg Lys Lys His Lys Lys Ser Pro Phe Thr Glu
    370                 375                 380

Asp Leu Gly Glu Pro Cys Glu Asn Arg Asp Lys Arg Ala Ile Lys Glu
385                 390                 395                 400

Thr Ser Leu Gly Lys Gly Lys Val Leu Gln Glu Val Asn His Lys Lys
                405                 410                 415

Ala Gly Gln Lys His Gly Asn Thr Lys Leu Met Pro Gln Lys Gln Asn
            420                 425                 430

His Gln Lys Ala Gly Gln Asn Leu Arg Asn Thr Glu Val Glu Leu Asp
        435                 440                 445

Leu Pro Ala Asp Ala Ile Val Ile His Gln Pro Arg Ser Thr Ala Asn
    450                 455                 460

Trp Gly Arg Asp Ser Pro Asp Lys Glu Asn Gln Pro Leu His Asn Ala
465                 470                 475                 480

Asp Arg Leu Leu Thr Ser Gln Gly Pro Val Asn Thr Trp Gln Leu Cys
                485                 490                 495

Arg Gln Glu Gly Arg Arg Ser Lys Lys Gly Gln Asn Lys Asn Lys
            500                 505                 510

Gln Gly Gln Arg Leu Leu Val Cys
    515                 520

<210> SEQ ID NO 23
<211> LENGTH: 242
<212> TYPE: PRT
<213> ORGANISM: Artificial Sequence
<220> FEATURE:
<223> OTHER INFORMATION: Consensus

<400> SEQUENCE: 23

Ser Pro Glu Pro Leu Ser Leu Asp Ala Val Leu Lys Leu Ser Pro Gly
1               5                   10                  15

Gly Leu Gln Asn Gly Asn Cys Tyr Asn Ala Leu Leu Thr Thr Pro Pro
            20                  25                  30

Leu Ala Tyr Met Leu Ser Glu His Ser Gln Thr Cys Gly Cys Leu Cys
        35                  40                  45

Met Ala Thr Leu His Gly Val Pro Ser Leu Phe His Gln Glu Asp Ala
    50                  55                  60

His Glu Phe Leu Met Phe Thr Met Cys Leu His Gln Ser Asp Ile His
65                  70                  75                  80

Ile Phe Gly Gly Trp Arg Ser Gln Ile Lys Cys Leu Cys Gly Ser Asp
                85                  90                  95

Thr Asp Leu Asp Ile Leu Asp Ile Ala Gln Ser Val Gln Ala Leu Lys
            100                 105                 110

Glu Glu Leu Gly Asn Ala Tyr Cys Gly Cys Gln Pro Ala Ser Lys Thr
        115                 120                 125
```

```
Leu His Lys Val Leu Val Leu Arg Phe Ser Thr Gly Asn Lys Val Tyr
    130                 135                 140

Pro Glu Leu Asp Pro Tyr Ser Gly Pro Leu Tyr Leu Tyr Ala Val Leu
145                 150                 155                 160

Val His Gly His Gly His Tyr Phe Val Lys Ala Gly Trp Tyr Lys Met
                165                 170                 175

Asp Asp Val Thr Thr Ser Val Leu Ala Tyr Val Leu Phe Tyr Gln Ser
                180                 185                 190

Gly Arg Leu Glu Lys Pro Glu Arg Ala Glu Leu Lys Leu Gln Glu
                195                 200                 205

Gln Asn Lys Asn Arg Val Glu Leu Pro Asp Val Ile His Gln Pro Leu
    210                 215                 220

Thr Gln Asn Thr Leu Gly Arg Arg Lys Gly Lys Asn Lys Arg Leu Leu
225                 230                 235                 240

Val Cys

<210> SEQ ID NO 24
<211> LENGTH: 494
<212> TYPE: PRT
<213> ORGANISM: Homo sapiens

<400> SEQUENCE: 24

Ser Leu Pro Glu Lys Ser Pro Leu Ser Cys Glu Thr Arg Val Asp Leu
1               5                   10                  15

Cys Asp Asp Leu Ala Pro Val Ala Arg Gln Leu Ala Pro Arg Glu Lys
                20                  25                  30

Leu Pro Leu Ser Ser Arg Arg Pro Ala Val Gly Ala Gly Leu Gln
            35                  40                  45

Asn Met Gly Asn Thr Cys Tyr Val Asn Ala Ser Leu Glu Trp Leu Thr
    50                  55                  60

Tyr Thr Pro Pro Leu Ala Asn Tyr Met Leu Ser Arg Glu His Ser Gln
65                  70                  75                  80

Thr Cys His Arg His Lys Gly Cys Met Leu Cys Thr Met Gln Ala His
                85                  90                  95

Ile Thr Arg Ala Leu His Asn Pro Gly His Val Ile Gln Pro Ser Gln
                100                 105                 110

Ala Leu Ala Ala Gly Phe His Arg Gly Lys Gln Glu Asp Ala His Glu
            115                 120                 125

Phe Leu Met Phe Thr Val Asp Ala Met Lys Lys Ala Cys Leu Pro Gly
    130                 135                 140

His Lys Gln Val Asp His His Ser Lys Asp Thr Thr Leu Ile His Gln
145                 150                 155                 160

Ile Phe Gly Gly Tyr Trp Arg Ser Gln Ile Lys Cys Leu His Cys His
                165                 170                 175

Gly Ile Ser Asp Thr Phe Asp Pro Tyr Leu Asp Ile Ala Leu Asp Ile
                180                 185                 190

Gln Ala Ala Gln Ser Val Gln Gln Ala Leu Glu Gln Leu Val Lys Pro
            195                 200                 205

Glu Glu Leu Asn Gly Glu Asn Ala Tyr His Cys Gly Val Cys Leu Gln
    210                 215                 220

Arg Ala Pro Ala Ser Lys Thr Leu Thr Leu His Thr Ser Ala Lys Val
225                 230                 235                 240

Leu Ile Leu Val Leu Lys Arg Phe Ser Asp Val Thr Gly Asn Lys Ile
                245                 250                 255
```

-continued

```
Ala Lys Asn Val Gln Tyr Pro Glu Cys Leu Asp Met Gln Pro Tyr Met
            260                 265                 270

Ser Gln Gln Asn Thr Gly Pro Leu Val Tyr Val Leu Tyr Ala Val Leu
        275                 280                 285

Val His Ala Gly Trp Ser Cys His Asn Gly His Tyr Phe Ser Tyr Val
    290                 295                 300

Lys Ala Gln Glu Gly Gln Trp Tyr Lys Met Asp Asp Ala Glu Val Thr
305                 310                 315                 320

Ala Ser Ser Ile Thr Ser Val Leu Ser Gln Gln Ala Tyr Val Leu Phe
                325                 330                 335

Tyr Ile Gln Lys Ser Glu Trp Glu Arg His Ser Glu Ser Val Ser Arg
            340                 345                 350

Gly Arg Glu Pro Arg Ala Leu Gly Ala Glu Asp Thr Asp Arg Arg Ala
        355                 360                 365

Thr Gln Gly Glu Leu Lys Arg Asp His Pro Cys Leu Gln Ala Pro Glu
    370                 375                 380

Leu Asp Glu His Leu Val Glu Arg Ala Thr Gln Glu Ser Thr Leu Asp
385                 390                 395                 400

His Trp Lys Phe Leu Gln Glu Gln Asn Lys Thr Lys Pro Glu Phe Asn
                405                 410                 415

Val Arg Lys Val Glu Gly Thr Leu Pro Pro Asp Val Leu Val Ile His
            420                 425                 430

Gln Ser Lys Tyr Lys Cys Gly Met Lys Asn His Pro Glu Gln Gln
        435                 440                 445

Ser Ser Leu Leu Asn Leu Ser Ser Thr Thr Pro Thr His Gln Glu Ser
    450                 455                 460

Met Asn Thr Gly Thr Leu Ala Ser Leu Arg Gly Arg Ala Arg Arg Ser
465                 470                 475                 480

Lys Gly Lys Asn Lys His Ser Lys Arg Ala Leu Leu Val Cys
                485                 490
```

<210> SEQ ID NO 25
<211> LENGTH: 11
<212> TYPE: DNA
<213> ORGANISM: Murine

<400> SEQUENCE: 25
tctgtgctgg g                                                    11

<210> SEQ ID NO 26
<211> LENGTH: 14
<212> TYPE: DNA
<213> ORGANISM: murine

<400> SEQUENCE: 26 ttttttttttt ttgt                                                14

<210> SEQ ID NO 27
<211> LENGTH: 31
<212> TYPE: PRT
<213> ORGANISM: murine

<400> SEQUENCE: 27

```
Lys Lys Ser Pro Phe Thr Glu Asp Leu Gly Glu Pro Cys Glu Asn Arg
 1               5                  10                  15

Asp Lys Arg Ala Ile Lys Glu Thr Ser Leu Gly Lys Gly Lys Val
            20                  25                  30
```

<210> SEQ ID NO 28
<211> LENGTH: 31
<212> TYPE: PRT
<213> ORGANISM: murine

<400> SEQUENCE: 28

Met Gln Cys His Cys Ser Phe Gly Ala Gly Glu Gly Thr Arg Glu Lys
 1               5                  10                  15

Asp Gly Arg Arg Glu Gln Arg Asn Leu Leu Arg Glu Gly Ser Ala
            20                  25                  30

<210> SEQ ID NO 29
<211> LENGTH: 143
<212> TYPE: DNA
<213> ORGANISM: Murine

<400> SEQUENCE: 29
aacaagcaga agcctctgcc cttgcttgtt cttgttcttc cccttcttcg atcttacatc      60
tccgaccctg actacagagc tgcccagggc tcatgaggcc tgagaggtag gagcctgtca     120
ccattgtgcc agggttgatt tct                                              143

<210> SEQ ID NO 30
<211> LENGTH: 228
<212> TYPE: DNA
<213> ORGANISM: Murine

<400> SEQUENCE: 30
gaagcctctg cccttgcttg gtcttgttct tccccttctt cgatcttcgt ctcccaccct      60
gacaacagag ctgcccaggg ctcgtgaggc ctgagagtcg aggagcctgt cagcattgtg     120
ccgggttgat tctccttgtc tggagcatcc ctgtcccagt ttgcagtgga tctgggctgg     180
tgaatcacaa ttgcatcagc aggcagatca agttcacctt cggatccc                  228

<210> SEQ ID NO 31
<211> LENGTH: 57
<212> TYPE: PRT
<213> ORGANISM: Yeast

<400> SEQUENCE: 31

Tyr Glu Leu Tyr Gly Val Ala Cys His Phe Gly Thr Leu Tyr Gly Gly
 1               5                  10                  15

His Tyr Thr Ala Tyr Val Lys Lys Gly Leu Lys Lys Gly Trp Leu Tyr
            20                  25                  30

Phe Asp Asp Thr Lys Tyr Lys Pro Val Lys Asn Lys Ala Asp Ala Ile
        35                  40                  45

Asn Ser Asn Ala Tyr Val Leu Phe Tyr
    50                  55

<210> SEQ ID NO 32
<211> LENGTH: 55
<212> TYPE: PRT
<213> ORGANISM: Homo sapiens

<400> SEQUENCE: 32

Tyr Asn Leu Tyr Ala Ile Ser Cys His Ser Gly Ile Leu Ser Gly Gly
 1               5                  10                  15

His Tyr Ile Thr Tyr Ala Lys Asn Pro Asn Cys Lys Trp Tyr Cys Tyr
            20                  25                  30

```
Asn Asp Ser Ser Cys Glu Glu Leu His Pro Asp Glu Ile Asp Thr Asp
         35                   40                  45

Ser Ala Tyr Ile Leu Phe Tyr
     50              55

<210> SEQ ID NO 33
<211> LENGTH: 56
<212> TYPE: PRT
<213> ORGANISM: Murine

<400> SEQUENCE: 33

Tyr Ala Leu Tyr Ala Val Leu Val His Asp Gly Ala Thr Ser His Ser
 1               5                  10                  15

Gly His Tyr Phe Cys Cys Val Lys Ala Gly His Gly Lys Trp Tyr Lys
             20                  25                  30

Met Asp Asp Thr Lys Val Thr Arg Cys Asp Val Thr Ser Val Leu Asn
         35                   40                  45

Glu Asn Ala Tyr Val Leu Phe Tyr
     50              55

<210> SEQ ID NO 34
<211> LENGTH: 28
<212> TYPE: PRT
<213> ORGANISM: Murine

<400> SEQUENCE: 34

Pro Cys Glu Asn Arg Asp Lys Arg Ala Ile Lys Glu Thr Ser Leu Gly
 1               5                  10                  15

Lys Gly Lys Val Leu Gln Glu Val Asn His Lys Lys
             20                  25

<210> SEQ ID NO 35
<211> LENGTH: 18
<212> TYPE: PRT
<213> ORGANISM: murine

<400> SEQUENCE: 35

Gly Leu Gly Asn Leu Gly Asn Thr Cys Phe Met Asn Ser Ala Leu Gln
 1               5                  10                  15

Cys Leu

<210> SEQ ID NO 36
<211> LENGTH: 56
<212> TYPE: PRT
<213> ORGANISM: murine

<400> SEQUENCE: 36

Tyr Asp Leu Ile Ala Val Ser Asn His Tyr Gly Ala Met Gly Val Gly
 1               5                  10                  15

His Tyr Thr Ala Tyr Ala Lys Asn Arg Leu Asn Gly Lys Trp Tyr Tyr
             20                  25                  30

Phe Asp Asp Ser Ser Val Ser Leu Ala Ser Glu Asp Gln Ile Val Thr
         35                   40                  45

Lys Ala Ala Tyr Val Leu Phe Tyr
     50              55

<210> SEQ ID NO 37
<211> LENGTH: 1873
<212> TYPE: DNA
<213> ORGANISM: murine
<220> FEATURE:
```

<221> NAME/KEY: CDS
<222> LOCATION: (199)...(1833)

<400> SEQUENCE: 37

```
gctttgcaga aaccacaccc aaattgggag aagcttgtct gggattggct gtccttggaa        60
gactgtaggc gtggtcacaa gactggagta taaaagactg agcatttgtc ctcacttgca       120
gagattctct ggagggaaag acttccttct gctcccttag aagactacag caagttattt      180
gaagaggtct ttggagac atg gtg gtt tct ctt tcc ttc cca gag caa gat        231
                    Met Val Val Ser Leu Ser Phe Pro Glu Gln Asp
                     1               5                  10 cca gcc cta tca tct cct ggt gcc caa cag ctg cat cag gat gaa gct        279
Pro Ala Leu Ser Ser Pro Gly Ala Gln Gln Leu His Gln Asp Glu Ala
         15                  20                  25 cag gta gtg gtg gag cta act gcc aat gac aag ccc agt ctg agt tgg        327
Gln Val Val Glu Leu Thr Ala Asn Asp Lys Pro Ser Leu Ser Trp
     30                  35                  40 gaa tgt ccc caa gga cca gga tgc ggg ctt cag aac aca ggc aac agc        375
Glu Cys Pro Gln Gly Pro Gly Cys Gly Leu Gln Asn Thr Gly Asn Ser
 45                  50                  55 tgc tac ctg aat gca gcc ctg cag tgc ttg aca cac aca cca cct cta        423
Cys Tyr Leu Asn Ala Ala Leu Gln Cys Leu Thr His Thr Pro Pro Leu
 60                  65                  70                  75 gct gac tac atg ctg tcc cag gag tac agt caa acc tgt tgt tcc cca        471
Ala Asp Tyr Met Leu Ser Gln Glu Tyr Ser Gln Thr Cys Cys Ser Pro
             80                  85                  90 gaa ggc tgt aag atg tgt gct atg gaa gcc cat gta acc cag agt ctc        519
Glu Gly Cys Lys Met Cys Ala Met Glu Ala His Val Thr Gln Ser Leu
         95                 100                 105 ctg cac tct cac tcg ggg gat gtc atg aag ccc tcc cag att ttg acc        567
Leu His Ser His Ser Gly Asp Val Met Lys Pro Ser Gln Ile Leu Thr
        110                 115                 120 tct gcc ttc cac aag cac cag cag gaa gat gcc cat gag ttt ctc atg        615
Ser Ala Phe His Lys His Gln Gln Glu Asp Ala His Glu Phe Leu Met
125                 130                 135 ttc acc ttg gaa aca atg cat gaa tcc tgc ctt caa gtg cac aga caa        663
Phe Thr Leu Glu Thr Met His Glu Ser Cys Leu Gln Val His Arg Gln
140                 145                 150                 155 tca gaa ccc acc tct gag gac agc tca ccc att cat gac ata ttt gga        711
Ser Glu Pro Thr Ser Glu Asp Ser Ser Pro Ile His Asp Ile Phe Gly
            160                 165                 170 ggc ttg tgg agg tct cag atc aag tgt ctc cat tgc cag ggt acc tca        759
Gly Leu Trp Arg Ser Gln Ile Lys Cys Leu His Cys Gln Gly Thr Ser
        175                 180                 185 gat aca tat gat cgc ttc ctg gat gtc ccc ctg gat atc agc tca gct        807
Asp Thr Tyr Asp Arg Phe Leu Asp Val Pro Leu Asp Ile Ser Ser Ala
    190                 195                 200 cag agt gta aat caa gcc ttg tgg gat aca gag aag tca gaa gag cta        855
Gln Ser Val Asn Gln Ala Leu Trp Asp Thr Glu Lys Ser Glu Glu Leu
205                 210                 215 cgt gga gag aat gcc tac tac tgt ggt agg tgt aga cag aag atg cca        903
Arg Gly Glu Asn Ala Tyr Tyr Cys Gly Arg Cys Arg Gln Lys Met Pro
220                 225                 230                 235 gct tcc aag acc ctg cat att cat agt gcc cca aag gta ctc ctg cta        951
Ala Ser Lys Thr Leu His Ile His Ser Ala Pro Lys Val Leu Leu Leu
            240                 245                 250 gtg tta aag cgc ttc tcg gcc ttc atg ggt aac aag ttg gac aga aaa        999
Val Leu Lys Arg Phe Ser Ala Phe Met Gly Asn Lys Leu Asp Arg Lys
        255                 260                 265
```

-continued

```
gta agc tac cca gag ttc ctt gac ctg aag cca tac ctg tcc cag cct      1047
Val Ser Tyr Pro Glu Phe Leu Asp Leu Lys Pro Tyr Leu Ser Gln Pro
        270                 275                 280 act gga gga cct ttg cct tat gcc ctc tat gct gtc ctg gtc cat gaa      1095
Thr Gly Gly Pro Leu Pro Tyr Ala Leu Tyr Ala Val Leu Val His Glu
285                 290                 295 ggt gcg act tgt cac agt gga cat tac ttc tct tat gtc aaa gcc aga      1143
Gly Ala Thr Cys His Ser Gly His Tyr Phe Ser Tyr Val Lys Ala Arg
300                 305                 310                 315 cat ggg gca tgg tac aag atg gat gat act aag gtc acc agc tgc gat      1191
His Gly Ala Trp Tyr Lys Met Asp Asp Thr Lys Val Thr Ser Cys Asp
                320                 325                 330 gtg act tct gtc ctg aat gag aat gcc tat gtg ctc ttc tat gtg cag      1239
Val Thr Ser Val Leu Asn Glu Asn Ala Tyr Val Leu Phe Tyr Val Gln
            335                 340                 345 cag act gac ctc aaa cag gtc agt att gac atg cca gag ggc aga gta      1287
Gln Thr Asp Leu Lys Gln Val Ser Ile Asp Met Pro Glu Gly Arg Val
        350                 355                 360 cat gag gtt ctc gac cct gaa tac cag ctg aag aaa tcc cgg aga aaa      1335
His Glu Val Leu Asp Pro Glu Tyr Gln Leu Lys Lys Ser Arg Arg Lys
365                 370                 375 aag cat aag aag aaa agc cct tgc aca gaa gat gcg gga gag ccc tgc      1383
Lys His Lys Lys Lys Ser Pro Cys Thr Glu Asp Ala Gly Glu Pro Cys
380                 385                 390                 395 aaa aac agg gag aag aga gca acc aaa gaa acc tcc tta ggg gag ggg      1431
Lys Asn Arg Glu Lys Arg Ala Thr Lys Glu Thr Ser Leu Gly Glu Gly
                400                 405                 410 aaa gtg ctt cag gaa aag aac cac aag aaa gct ggg cag aaa cat gag      1479
Lys Val Leu Gln Glu Lys Asn His Lys Lys Ala Gly Gln Lys His Glu
            415                 420                 425 aat acc aaa ctt gtg cct cag gaa cag aac cac cag aaa ctt ggg cag      1527
Asn Thr Lys Leu Val Pro Gln Glu Gln Asn His Gln Lys Leu Gly Gln
        430                 435                 440 aaa cac agg atc aat gaa atc ttg cct cag gaa cag aac cac cag aaa      1575
Lys His Arg Ile Asn Glu Ile Leu Pro Gln Glu Gln Asn His Gln Lys
445                 450                 455 gct ggg cag agc ctc agg aac acg gaa ggt gaa ctt gat ctg cct gct      1623
Ala Gly Gln Ser Leu Arg Asn Thr Glu Gly Glu Leu Asp Leu Pro Ala
460                 465                 470                 475 gat gca att gtg att cac ctg ctc aga tcc aca gaa aac tgg ggc agg      1671
Asp Ala Ile Val Ile His Leu Leu Arg Ser Thr Glu Asn Trp Gly Arg
                480                 485                 490 gat gct cca gac aag gag aat caa ccc tgg cac aat gct gac agg ctc      1719
Asp Ala Pro Asp Lys Glu Asn Gln Pro Trp His Asn Ala Asp Arg Leu
            495                 500                 505 ctc acc tct cag gac cct gtg aac act ggg cag ctc tgt aga cag gaa      1767
Leu Thr Ser Gln Asp Pro Val Asn Thr Gly Gln Leu Cys Arg Gln Glu
        510                 515                 520 gga aga cga aga tca aag aag ggg aag aac aag aac aag caa ggg cag      1815
Gly Arg Arg Arg Ser Lys Lys Gly Lys Asn Lys Asn Lys Gln Gly Gln
525                 530                 535 agg ctt ctg ctt gtt tgc tagtgttcac tcacccactc acacaggctc             1863
Arg Leu Leu Leu Val Cys
540                 545 ctgtggacac                                                           1873

<210> SEQ ID NO 38
<211> LENGTH: 545
<212> TYPE: PRT
<213> ORGANISM: murine
```

-continued

<400> SEQUENCE: 38

```
Met Val Val Ser Leu Ser Phe Pro Glu Gln Asp Pro Ala Leu Ser Ser
  1               5                  10                  15
Pro Gly Ala Gln Gln Leu His Gln Asp Glu Ala Gln Val Val Val Glu
             20                  25                  30
Leu Thr Ala Asn Asp Lys Pro Ser Leu Ser Trp Glu Cys Pro Gln Gly
         35                  40                  45
Pro Gly Cys Gly Leu Gln Asn Thr Gly Asn Ser Cys Tyr Leu Asn Ala
     50                  55                  60
Ala Leu Gln Cys Leu Thr His Thr Pro Pro Leu Ala Asp Tyr Met Leu
 65                  70                  75                  80
Ser Gln Glu Tyr Ser Gln Thr Cys Cys Ser Pro Glu Gly Cys Lys Met
                 85                  90                  95
Cys Ala Met Glu Ala His Val Thr Gln Ser Leu Leu His Ser His Ser
            100                 105                 110
Gly Asp Val Met Lys Pro Ser Gln Ile Leu Thr Ser Ala Phe His Lys
        115                 120                 125
His Gln Gln Glu Asp Ala His Glu Phe Leu Met Phe Thr Leu Glu Thr
    130                 135                 140
Met His Glu Ser Cys Leu Gln Val His Arg Gln Ser Glu Pro Thr Ser
145                 150                 155                 160
Glu Asp Ser Ser Pro Ile His Asp Ile Phe Gly Gly Leu Trp Arg Ser
                165                 170                 175
Gln Ile Lys Cys Leu His Cys Gln Gly Thr Ser Asp Thr Tyr Asp Arg
            180                 185                 190
Phe Leu Asp Val Pro Leu Asp Ile Ser Ser Ala Gln Ser Val Asn Gln
        195                 200                 205
Ala Leu Trp Asp Thr Glu Lys Ser Glu Glu Leu Arg Gly Glu Asn Ala
    210                 215                 220
Tyr Tyr Cys Gly Arg Cys Arg Gln Lys Met Pro Ala Ser Lys Thr Leu
225                 230                 235                 240
His Ile His Ser Ala Pro Lys Val Leu Leu Leu Val Leu Lys Arg Phe
                245                 250                 255
Ser Ala Phe Met Gly Asn Lys Leu Asp Arg Lys Val Ser Tyr Pro Glu
            260                 265                 270
Phe Leu Asp Leu Lys Pro Tyr Leu Ser Gln Pro Thr Gly Gly Pro Leu
        275                 280                 285
Pro Tyr Ala Leu Tyr Ala Val Leu Val His Glu Gly Ala Thr Cys His
    290                 295                 300
Ser Gly His Tyr Phe Ser Tyr Val Lys Ala Arg His Gly Ala Trp Tyr
305                 310                 315                 320
Lys Met Asp Asp Thr Lys Val Thr Ser Cys Asp Val Thr Ser Val Leu
                325                 330                 335
Asn Glu Asn Ala Tyr Val Leu Phe Tyr Val Gln Gln Thr Asp Leu Lys
            340                 345                 350
Gln Val Ser Ile Asp Met Pro Glu Gly Arg Val His Glu Val Leu Asp
        355                 360                 365
Pro Glu Tyr Gln Leu Lys Lys Ser Arg Arg Lys His Lys Lys
    370                 375                 380
Ser Pro Cys Thr Glu Asp Ala Gly Glu Pro Cys Lys Asn Arg Glu Lys
385                 390                 395                 400
Arg Ala Thr Lys Glu Thr Ser Leu Gly Glu Gly Lys Val Leu Gln Glu
```

```
                        405                 410                      415
Lys Asn His Lys Lys Ala Gly Gln Lys His Glu Asn Thr Lys Leu Val
            420                 425                 430
Pro Gln Glu Gln Asn His Gln Lys Leu Gly Gln Lys His Arg Ile Asn
            435                 440                 445
Glu Ile Leu Pro Gln Gln Asn His Gln Lys Ala Gly Gln Ser Leu
    450                 455                 460
Arg Asn Thr Glu Gly Glu Leu Asp Leu Pro Ala Asp Ala Ile Val Ile
465                 470                 475                 480
His Leu Leu Arg Ser Thr Glu Asn Trp Gly Arg Ala Pro Asp Lys
                485                 490                 495
Glu Asn Gln Pro Trp His Asn Ala Asp Arg Leu Leu Thr Ser Gln Asp
                500                 505                 510
Pro Val Asn Thr Gly Gln Leu Cys Arg Gln Glu Gly Arg Arg Ser
            515                 520                 525
Lys Lys Gly Lys Asn Lys Asn Lys Gln Gly Gln Arg Leu Leu Leu Val
        530                 535                 540
Cys
545

<210> SEQ ID NO 39
<211> LENGTH: 160
<212> TYPE: DNA
<213> ORGANISM: murine

<400> SEQUENCE: 39
cagatccagc cctatcatct cctgatgccc cagagctgca tcaggatgaa gctcaggtgg      60
tggaggagct aactgtcaat ggaaagcaca gtctgagttg ggagagtccc caaggaccag     120
gatgcgggct ccagaacaca ggcaacagct gctacctgaa                           160

<210> SEQ ID NO 40
<211> LENGTH: 158
<212> TYPE: DNA
<213> ORGANISM: Murine

<400> SEQUENCE: 40
gatccagccc tatcatctcc tggtgcccaa cacctgcatc aggatgaagc tcaggtagtg      60
gtggagctaa ctgccaatga caagcccagt ctgagttggg aatgtcccca aggaccagga     120
tgcgggcttc agaacacagg caacagctgc tacctgaa                             158

<210> SEQ ID NO 41
<211> LENGTH: 156
<212> TYPE: DNA
<213> ORGANISM: Murine

<400> SEQUENCE: 41
tccagcacta tcatctcctg atgccccaga gctgcatcag tttgaagctc aggtggtgga      60
ggtgctaact accaatggaa agttcagtct gagttgggag agtccctaag gaccaggatg     120
cgggctccag aacacaggca acagctgcta cctgaa                               156

<210> SEQ ID NO 42
<211> LENGTH: 159
<212> TYPE: DNA
<213> ORGANISM: murine

<400> SEQUENCE: 42
```

```
cagatccagc actatcatct cctgatgccc cagagctgca tcaggatgaa gctcaggtgg        60
tggaggagct aacatccaat ggaaagcaca gtctgagttg ggagagtccc caaggaccag       120
gatgcgggct ccagaacaca ggcaacagct gctacctga                              159
```

<210> SEQ ID NO 43
<211> LENGTH: 160
<212> TYPE: DNA
<213> ORGANISM: Artificial Sequence
<220> FEATURE:
<223> OTHER INFORMATION: consensus

<400> SEQUENCE: 43

```
cagatccagc cctatcatct cctgatgccc cagagctgca tcaggatgaa gctcaggtgg        60
tggaggagct aactgccaat ggaaagcaca gtctgagttg ggagagtccc caaggaccag       120
gatgcgggct ccagaacaca ggcaacagct gctacctgaa                             160
```

<210> SEQ ID NO 44
<211> LENGTH: 21
<212> TYPE: PRT
<213> ORGANISM: Artificial Sequence
<220> FEATURE:
<223> OTHER INFORMATION: consensus

<400> SEQUENCE: 44

```
Gln Cys Leu Thr His Thr Pro Pro Leu Ala Asp Tyr Met Leu Ser Gln
 1               5                  10                  15

Glu Tyr Ser Gln Thr
            20
```

<210> SEQ ID NO 45
<211> LENGTH: 20
<212> TYPE: DNA
<213> ORGANISM: Murine

<400> SEQUENCE: 45

```
tttgaagagg tctttggaga                                                    20
```

<210> SEQ ID NO 46
<211> LENGTH: 20
<212> TYPE: DNA
<213> ORGANISM: Murine

<400> SEQUENCE: 46

```
gtgtccacag gagcctgtgt                                                    20
```

<210> SEQ ID NO 47
<211> LENGTH: 29
<212> TYPE: DNA
<213> ORGANISM: Murine

<400> SEQUENCE: 47

```
gcgaattctt tgaagagggt ctttggaga                                          29
```

<210> SEQ ID NO 48
<211> LENGTH: 28
<212> TYPE: DNA
<213> ORGANISM: Murine

<400> SEQUENCE: 48

```
atctcgaggt gtccacagga gcctgtgt                                           28
```

```
<210> SEQ ID NO 49
<211> LENGTH: 20
<212> TYPE: DNA
<213> ORGANISM: murine

<400> SEQUENCE: 49
tttgaagagg tctttggaga                                                    20

<210> SEQ ID NO 50
<211> LENGTH: 20
<212> TYPE: DNA
<213> ORGANISM: murine

<400> SEQUENCE: 50
gtgtccacag gagcctgtgt                                                    20

<210> SEQ ID NO 51
<211> LENGTH: 8
<212> TYPE: PRT
<213> ORGANISM: Murine

<400> SEQUENCE: 51

Pro Gln Glu Gln Asn His Gln Lys
1               5
```